United States Patent
Fuji et al.

(10) Patent No.: US 10,234,343 B2
(45) Date of Patent: *Mar. 19, 2019

(54) PRESSURE SENSOR, ACOUSTIC MICROPHONE, BLOOD PRESSURE SENSOR, AND TOUCH PANEL

(71) Applicant: Kabushiki Kaisha Toshiba, Minato-ku (JP)

(72) Inventors: Yoshihiko Fuji, Kanagawa-ken (JP); Kei Masunishi, Kanagawa-ken (JP); Hideaki Fukuzawa, Kanagawa-ken (JP); Yoshihiro Higashi, Ishikawa-ken (JP); Michiko Hara, Kanagawa-ken (JP); Akio Hori, Kanagawa-ken (JP); Tomohiko Nagata, Kanagawa-ken (JP); Shiori Kaji, Kanagawa-ken (JP); Akiko Yuzawa, Kanagawa-ken (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/807,020

(22) Filed: Nov. 8, 2017

(65) Prior Publication Data
US 2018/0067005 A1   Mar. 8, 2018

Related U.S. Application Data

(63) Continuation of application No. 15/388,629, filed on Dec. 22, 2016, now Pat. No. 9,921,114, which is a (Continued)

(30) Foreign Application Priority Data
Jun. 12, 2013   (JP) .................................. 2013-124111

(51) Int. Cl.
*G01L 9/00* (2006.01)
*G01L 1/22* (2006.01)
(Continued)

(52) U.S. Cl.
CPC ........ *G01L 1/2287* (2013.01); *A61B 5/02141* (2013.01); *A61B 5/02438* (2013.01); (Continued)

(58) Field of Classification Search
CPC ......... G01L 1/2287; G01L 1/12; G01L 1/205; G01L 1/2262; G01L 1/2293; G01L 5/161; (Continued)

(56) References Cited

U.S. PATENT DOCUMENTS 3,915,015 A   10/1975 Crane
5,898,548 A   4/1999 Dill et al.
(Continued)

FOREIGN PATENT DOCUMENTS

JP   H01-211986 A   8/1989
JP   2002-304711 A   10/2002
(Continued)

OTHER PUBLICATIONS

Fletcher, Rich. "Force transduction materials for human-technology interfaces." IBM systems journal 35.3.4 (1996): 630-638.*
(Continued)

*Primary Examiner* — Max H Noori
(74) *Attorney, Agent, or Firm* — Oblon, McClelland, Maier & Neustadt, L.L.P.

(57) ABSTRACT

According to one embodiment, a pressure sensor includes a film part, and a sensing unit. A circumscribing rectangle circumscribing a configuration of a film surface of the film part has a first side, a second side, a third side connected to one end of the first side and one end of the second side, a fourth side connected to one other end of the first side and (Continued)

one other end of the second side, and a centroid of the circumscribing rectangle. The circumscribing rectangle includes a first region enclosed by the first side, line segments connecting the centroid to the one end of the first side, and to the one other end of the first side. The sensing unit includes sensing elements provided on a portion of the film surface overlapping the first region. Each sensing element includes a first, second magnetic layers, and a spacer layer.

7 Claims, 38 Drawing Sheets

Related U.S. Application Data continuation of application No. 14/197,448, filed on Mar. 5, 2014, now Pat. No. 9,596,995.

(51) Int. Cl.
| | |
|---|---|
| *A61B 5/021* | (2006.01) |
| *G01L 1/12* | (2006.01) |
| *A61B 5/024* | (2006.01) |
| *H04R 1/02* | (2006.01) |
| *H04R 19/00* | (2006.01) |
| *G01L 1/20* | (2006.01) |
| *G01L 5/16* | (2006.01) |
| *G06F 3/041* | (2006.01) |
| *A61B 5/00* | (2006.01) |
| *H04R 1/04* | (2006.01) |
| *H04R 7/00* | (2006.01) |
| *H04R 19/04* | (2006.01) |

(52) U.S. Cl.
CPC ............. *A61B 5/7475* (2013.01); *G01L 1/12* (2013.01); *G01L 1/205* (2013.01); *G01L 1/2262* (2013.01); *G01L 1/2293* (2013.01); *G01L 5/161* (2013.01); *G01L 9/0051* (2013.01); *G06F 3/041* (2013.01); *G06F 3/0414* (2013.01); *H04R 1/028* (2013.01); *H04R 1/04* (2013.01); *H04R 7/00* (2013.01); *H04R 19/005* (2013.01); *G06F 2203/04105* (2013.01); *H04R 19/04* (2013.01); *H04R 2499/11* (2013.01)

(58) Field of Classification Search
CPC ............... G01L 9/0051; A61B 5/02141; A61B 5/02438; A61B 5/7475; H04R 1/028; H04R 1/04; H04R 7/00; H04R 19/005; H04R 19/04; H04R 2499/11; G06F 3/041; G06F 3/0414; G06F 2203/04105
USPC ................................................... 73/862.628
See application file for complete search history.

(56) References Cited

U.S. PATENT DOCUMENTS

| | | |
|---|---|---|
| 6,098,464 A | 8/2000 | Avisse |
| 7,490,522 B2 | 2/2009 | Ruehrig |
| 7,500,406 B2 | 3/2009 | Morimoto |
| 7,705,591 B2 | 4/2010 | Geren |
| 2002/0073785 A1 | 6/2002 | Prakash |
| 2006/0246271 A1 | 11/2006 | Quandt et al. |
| 2007/0099031 A1 | 5/2007 | Chung |
| 2009/0211362 A1 | 8/2009 | Krog |
| 2011/0295128 A1 | 12/2011 | Yuasa et al. |
| 2012/0079887 A1 | 4/2012 | Giddings |
| 2012/0241619 A1 | 9/2012 | Fukuzawa et al. |
| 2012/0245477 A1 | 9/2012 | Giddings |
| 2013/0079648 A1 | 3/2013 | Fukuzawa |
| 2013/0170669 A1 | 7/2013 | Fukuzawa et al. |
| 2013/0255069 A1 | 10/2013 | Higashi |
| 2013/0255393 A1 | 10/2013 | Fukuzawa et al. |
| 2014/0207007 A1 | 7/2014 | Miyasaka et al. ....... 359/489.07 |
| 2014/0369530 A1 | 12/2014 | Fuji et al. |
| 2015/0082919 A1 | 3/2015 | Higashi |
| 2015/0266717 A1 | 9/2015 | Okamoto |
| 2016/0009545 A1 | 1/2016 | Fuji |

FOREIGN PATENT DOCUMENTS

| | | |
|---|---|---|
| JP | 2012-78186 A | 4/2012 |
| JP | 2013-72712 A | 4/2013 |
| JP | 5214806 B2 | 6/2013 |
| JP | 2014-240824 A | 12/2014 |
| JP | 2015-92174 | 5/2015 |
| JP | 2017-138321 A | 8/2017 |

OTHER PUBLICATIONS

D. Meyners et al. "Pressure sensor based on magnetic tunnel junctions", Journal of Applied Physics 105, 2009, 3 pages.
M. Loehndorf et al. "Characterization of magnetostrictive TMR pressure sensors by MOKE", Journal of Magnetism and Magnetic Materials 316, 2007, 3 pages.
M. Loehndorf et al. "Highly sensitive strain sensors based on magnetic tunneling junctions", Applied Physics Letters, vol. 81, No. 2, 2002, 3 pages.
Chang, et al., "A novel inverse-magnetostrictive type pressure sensor with planar sensing inductor." Micro Electro Mechanical Systems (MEMS), 2013 IEEE 26$^{th}$ International Conference on. IEEE, Jan. 2013.
Kim, S.W., et al., "Improvement of pulse diagnostic apparatus with array sensor of magnetic tunneling junctions," Journal of Applied Physics 99.8 (2006): 08R908.
Biomedical Sensors. Michael R. Neuman. The Electrical Engineering Handbook, Second Edition. Sep. 1997.
Filanovsky, I.M. 1999. Bridge Circuits. Wiley Encyclopedia of Electrical and Electronics Engineering.

* cited by examiner

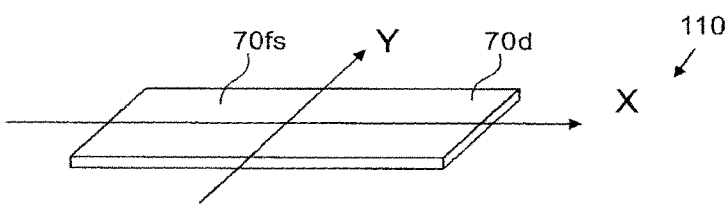
FIG. 3A
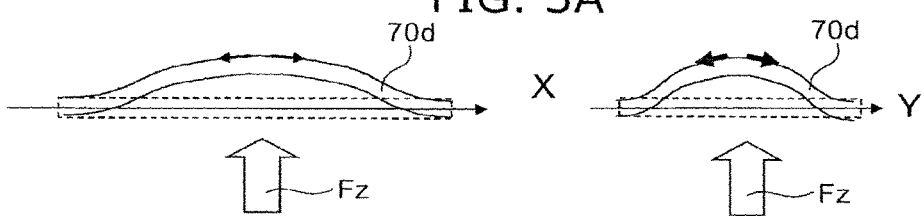
FIG. 3B
FIG. 3C
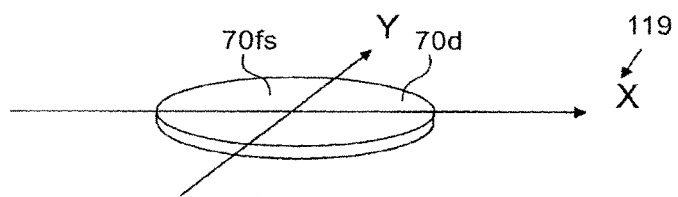
FIG. 4A
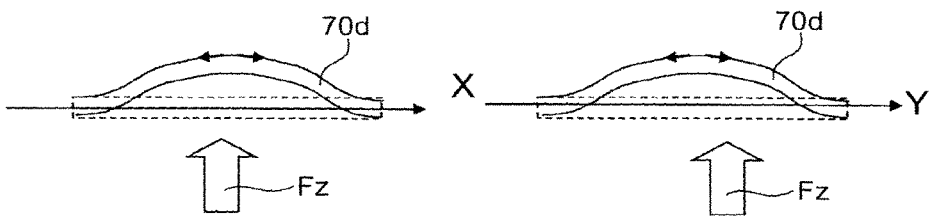
FIG. 4B
FIG. 4C

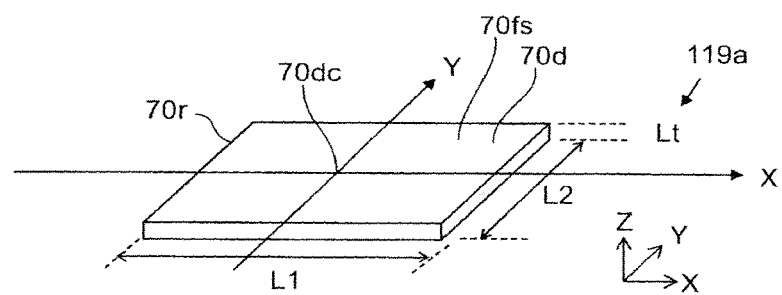
FIG. 6A
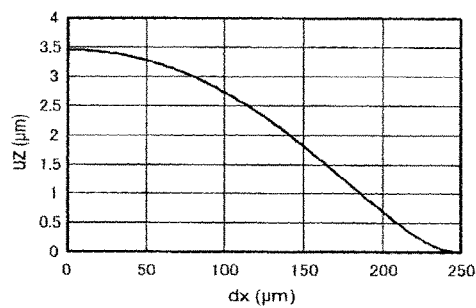
FIG. 6B
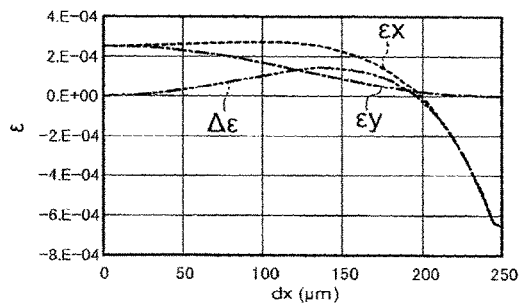
FIG. 6C
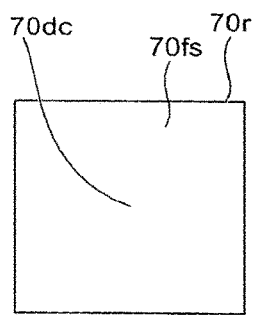
FIG. 6D
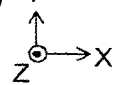

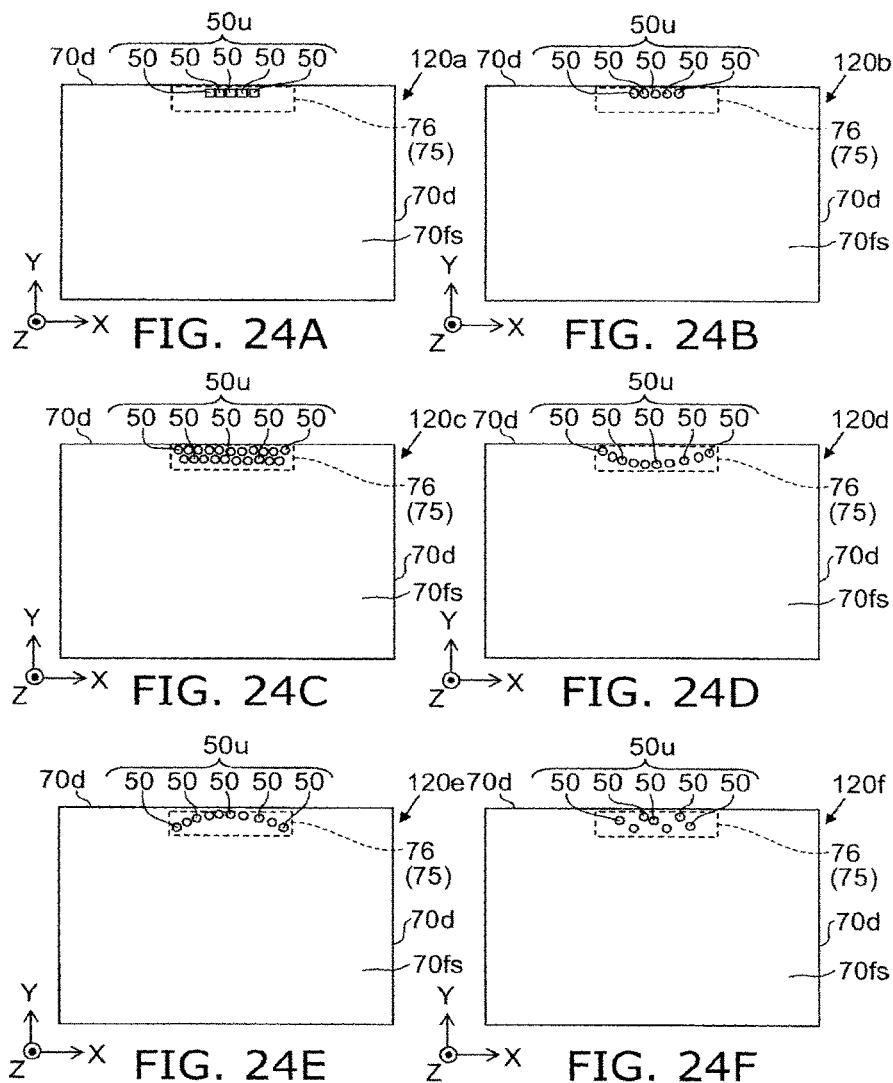

PRESSURE SENSOR, ACOUSTIC MICROPHONE, BLOOD PRESSURE SENSOR, AND TOUCH PANEL

CROSS-REFERENCE TO RELATED APPLICATIONS

This application is a continuation of U.S. patent application Ser. No. 15/388,629, filed on Dec. 22, 2016, which is a continuation of U.S. patent application Ser. No. 14/197,448, filed on Mar. 5, 2014, and is based upon and claims the benefit of priority from Japanese Patent Application No. 2013-124111, filed on Jun. 12, 2013; the entire contents of each of the above applications are incorporated herein by reference.

FIELD

Embodiments described herein relate generally to a pressure sensor, an acoustic microphone, a blood pressure sensor, and a touch panels.

BACKGROUND

Pressure sensors that use MEMS (Micro Electro Mechanical Systems) technology include, for example, a piezo resistance-change type and an electrostatic-capacitance type. On the other hand, a pressure sensor that uses spin technology has been proposed. In the pressure sensor using spin technology, a resistance change corresponding to the strain is sensed. For the pressure sensor using spin technology, a highly-sensitive pressure sensor is desired.

BRIEF DESCRIPTION OF THE DRAWINGS

FIG. 3A to FIG. 3C are schematic views illustrating the operation of the pressure sensor according to the first embodiment;

FIG. 4A to FIG. 4C are schematic views illustrating the operation of a pressure sensor of a reference example;

FIG. 6A to FIG. 6D are schematic views illustrating the configuration and characteristics of a pressure sensor of a reference example;

FIG. 24A to FIG. 24F are schematic plan views illustrating other pressure sensors according to the second embodiment;

DETAILED DESCRIPTION

Figure 1A:
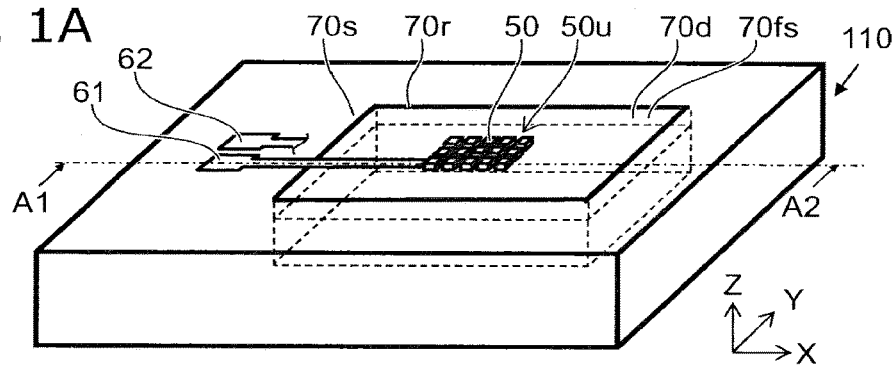
FIG. 1A to FIG. 1D are schematic views illustrating a pressure sensor according to the first embodiment.

According to one embodiment, a pressure sensor includes a film part, and a sensing unit. The film part is supported by a support unit, and is flexible. A first length of the film part in a first direction in a film surface of the film part is longer than a second length of the film part in a second direction perpendicular to the first direction in the film surface. A circumscribing rectangle is configured to circumscribe a configuration of the film surface. The circumscribing rectangle has a first side extending in the first direction to have the first length, a second side extending in the first direction to be separated from the first side, a third side extending in the second direction to be connected to one end of the first side and one end of the second side, the third side having the second length shorter than the first length, a fourth side extending in the second direction to be separated from the third side and connected to one other end of the first side and one other end of the second side, the fourth side having the second length, and a centroid of the circumscribing rectangle. The circumscribing rectangle includes a first region enclosed by the first side, a first line segment and a second line segment. The first line segment connects the centroid to the one end of the first side. The second line segment connects the centroid to the one other end of the first side. The sensing unit includes a plurality of sensing elements provided on a portion of the film surface overlapping the first region. Each of the plurality of sensing elements includes a first magnetic layer, a second magnetic layer provided between the first magnetic layer and the film part, and a spacer layer provided between the first magnetic layer and the second magnetic layer, the spacer layer being nonmagnetic. Positions of at least two of the plurality of sensing elements along the first direction are different from each other.

According to one embodiment, a pressure sensor includes a film part, and a sensing unit. The film part is supported by a support unit, and is flexible. A first length of the film part in a first direction in a film surface of the film part is longer than a second length of the film part in a second direction perpendicular to the first direction in the film surface. A configuration of the film surface has a first side extending in the first direction, a second side extending in the first direction to be separated from the first side, a distance between the first side and the second side being the second length, a third side extending in the second direction, and a fourth side extending in the second direction to be separated from the third side, a distance between the third side and the fourth side being the first length. The film surface has a central portion, and a peripheral portion provided around the central portion, the peripheral portion having a first element disposition region provided along the first side. The sensing unit includes a plurality of sensing elements provided on the first element disposition region of the film surface. Each of the plurality of sensing elements includes a first magnetic layer, a second magnetic layer provided between the first magnetic layer and the film part, and a spacer layer provided between the first magnetic layer and the second magnetic layer, the spacer layer being nonmagnetic. Positions of at least two of the plurality of sensing elements along the first direction are different from each other.

According to one embodiment, a pressure sensor includes a film part, and a sensing unit. The film part is supported by a support unit, and is flexible. A first length of the film part in a first direction in a film surface of the film part is longer than a second length of the film part in a second direction perpendicular to the first direction in the film surface. A configuration of the film surface is a flattened circle having the first direction as a major axis and the second direction as a minor axis. The film surface has a central portion, and a peripheral portion provided around the central portion. The peripheral portion has a first element disposition region provided along an arc along the major axis. The sensing unit includes a plurality of sensing elements provided on the first element disposition region of the film surface. Each of the plurality of sensing elements includes a first magnetic layer, a second magnetic layer provided between the first magnetic layer and the film part, and a spacer layer provided between the first magnetic layer and the second magnetic layer, the spacer layer being nonmagnetic. Positions of at least two of the plurality of sensing elements along the first direction are different from each other.

According to one embodiment, a pressure sensor includes a film part, and a sensing unit. The film part is supported by a support unit, and is flexible. A first length of a film surface of the film part in a first direction in the film surface is longer than a second length of the film surface in a second direction perpendicular to the first direction in the film surface. The film surface has a central portion, and a peripheral portion provided around the central portion. The sensing unit includes a sensing element provided on the central portion. The sensing element includes a first magnetic layer, a second magnetic layer provided between the first magnetic layer and the film part, and a spacer layer provided between the first magnetic layer and the second magnetic layer.

According to one embodiment, an acoustic microphone including the pressure sensor is provided, According to one embodiment, a blood pressure sensor including the pressure sensor 1 is provided, According to one embodiment, a touch panel including the pressure sensor is provided, Various embodiments will be described hereinafter with reference to the accompanying drawings.

The drawings are schematic or conceptual; and the relationships between the thicknesses and widths of portions, the proportions of sizes between portions, etc., are not necessarily the same as the actual values thereof. Further, the dimensions and/or the proportions may be illustrated differently between the drawings, even for identical portions.

In the drawings and the specification of the application, components similar to those described in regard to a drawing thereinabove are marked with like reference numerals, and a detailed description is omitted as appropriate.

First Embodiment

FIG. 1A to FIG. 1D are schematic views illustrating a pressure sensor according to the first embodiment.

Figure 1B:
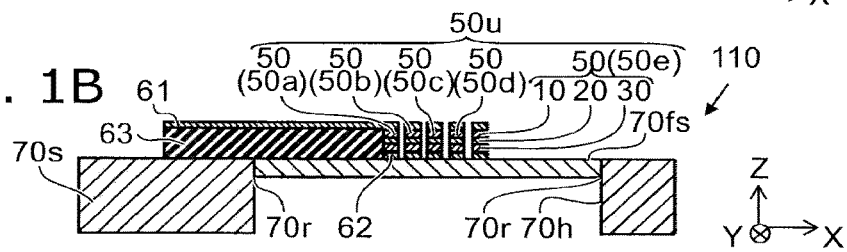
Figure 1C:
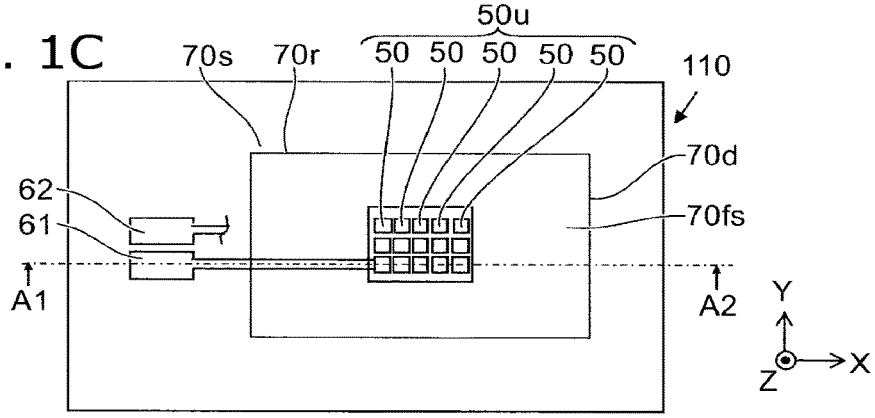
Figure 1D:
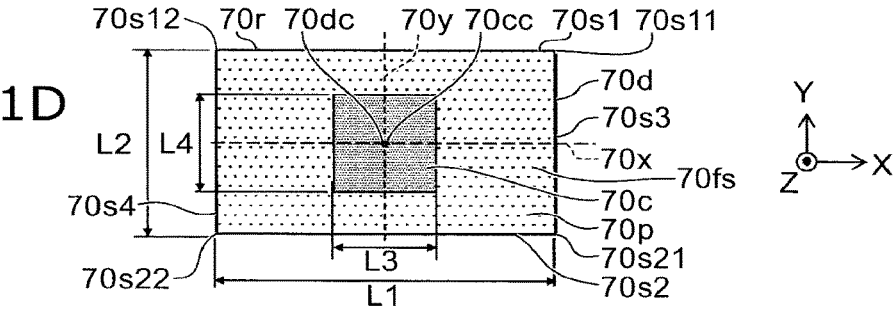

FIG. 1A is a schematic perspective view. FIG. 1B is a cross-sectional view along line A1-A2 of FIG. 1A and FIG. 1C. FIG. 1C is a schematic plan view. FIG. 1D is a schematic plan view of a film part included in the pressure sensor.

As shown in FIG. 1A to FIG. 1C, the pressure sensor 110 according to the embodiment includes the film part 70d and a sensing unit 50u. In the example, a support unit 70s is provided.

The support unit 70s is, for example, a substrate. The film part 70d is supported by the support unit 70s. The film part 70d is flexible. The film part 70d is, for example, a diaphragm. The film part 70d may be integral with the support unit 70s or may be a separate entity. The film part 70d may include the same material as the support unit 70s or a material that is different from that of the support unit 70s. A portion of the substrate that is used to form the support unit 70s may be removed; and the film part 70d may be the thin portion of the substrate.

The thickness of the film part 70d is thinner than the thickness of the support unit 70s. The film part 70d and the support unit 70s may include the same material; and in the case where the film part 70d and the support unit 70s are integral, the thin portion is used to form the film part 70d; and the thick portion is used to form the support unit 70s.

The support unit 70s may have a through-hole piercing the support unit 70s in the thickness direction; and the film part 70d may be provided to cover the through-hole. In such a case, for example, the film of the material used to form the film part 70d may extend onto a portion of the support unit 70s other than the through-hole. In such a case, the portion of the film of the material used to form the film part 70d that overlaps the through-hole is used to form the film part 70d.

The film part 70d has an outer edge 70r. In the case where the film part 70d and the support unit 70s include the same material and are integral, the outer edge of the thin portion is used to form the outer edge 70r of the film part 70d. In the case where the support unit 70s has a through-hole piercing the support unit 70s in the thickness direction and the film part 70d is provided to cover the through-hole, the outer edge of the portion of the film of the material used to form the film part 70d that overlaps the through-hole is used to form the outer edge 70r of the film part 70d.

The support unit 70s may continuously support the outer edge 70r of the film part 70d or may support a portion of the outer edge 70r of the film part 70d.

A direction perpendicular to a plane including the outer edge 70r is taken as a Z-axis direction. One direction perpendicular to the Z-axis direction is taken as an X-axis direction. A direction perpendicular to the Z-axis direction and the X-axis direction is taken as a Y-axis direction.

One direction in a film surface 70fs of the film part 70d is taken as a first direction. The first direction is, for example, the X-axis direction. A direction perpendicular to the first direction in the film surface 70fs is taken as a second direction. The second direction is, for example, the Y-axis direction.

In the embodiment, the planar configuration of the film part 70d is an anisotropic configuration.

For example, as illustrated in FIG. 1D, the film part 70d has a first length L1 in the first direction (the X-axis direction) and a second length L2 in the second direction (the Y-axis direction). The first length L1 is longer than the second length L2. The first length L1 is the maximum length of the film part 70d in the first direction. The second length L2 is the maximum length of the film part 70d in the second direction.

In the example, the planar configuration of the film part 70d is substantially rectangular. In other words, the film surface 70fs has first to fourth sides 70s1 to 70s4. The first side 70s1 is provided along the first direction. The second side 70s2 is provided along the first direction to be separated from the first side 70s1. The distance between the first side 70s1 and the second side 70s2 is, for example, the second length L2. The third side 70s3 is provided along the second direction to be connected to one end 70s11 of the first side 70s1 and one end 70s21 of the second side 70s2. The fourth side 70s4 is provided along the second direction to be separated from the third side 70s3 and connected to the other end 70s12 of the first side 70s1 and the other end 70s22 of the second side 70s2. The distance between the third side 70s3 and the fourth side 70s4 is, for example, the first length. As described below, these sides may be connected to each other by corner portions having linear configurations or curved configurations.

As shown in FIG. 1D, the film surface 70fs of the film part 70d has a central portion 70c and a peripheral portion 70p. The peripheral portion 70p is provided around the central portion 70c. The peripheral portion 70p is provided around the central portion 70c when the film part 70d is projected onto a plane (e.g., the X-Y plane) parallel to the film surface 70fs.

The sensing unit 50u is provided on the central portion 70c of the film part 70d.

In the specification of the application, the state of being "provided on" includes not only the state of being provided in direct contact but also the state of being provided with another component inserted therebetween.

The sensing unit 50u includes a sensing element 50. In the example, the sensing unit 50u includes multiple sensing elements 50 (e.g., first to fifth sensing elements 50a to 50e, etc.). The number of the sensing elements 50 provided in the sensing unit 50u may be 1.

As shown in FIG. 1B, the sensing element 50 includes a first magnetic layer 10, a second magnetic layer 20, and a spacer layer 30. The second magnetic layer 20 is provided between the first magnetic layer 10 and the film part 70d. The spacer layer 30 is provided between the first magnetic layer 10 and the second magnetic layer 20. The spacer layer 30 may include, for example, a nonmagnetic material.

A first interconnect 61 and a second interconnect 62 are provided in the pressure sensor 110. The first interconnect 61 is connected to one selected from the sensing elements 50. The second interconnect 62 is connected to one selected from the sensing elements 50. For example, an inter-layer insulating film 63 is provided between the first interconnect 61 and the second interconnect 62 to electrically insulate the first interconnect 61 from the second interconnect 62. A voltage is applied between the first interconnect 61 and the second interconnect 62; and the voltage is applied to the sensing elements 50 via the first interconnect 61 and the second interconnect 62. The film part 70d deforms when pressure is applied to the pressure sensor 110. The electrical resistance of the sensing elements 50 changes as the film part 70d deforms. The pressure can be sensed by sensing the change of the electrical resistance via the first interconnect 61 and the second interconnect 62.

For example, as shown in FIG. 1D, a centroid 70dc of the film surface 70fs substantially overlaps the centroid of the central portion 70c. The centroid of the film part 70d substantially overlaps the centroid of the central portion 70c when projected onto the X-Y plane. For example, a centroid 70cc of the central portion 70c is aligned with or proximal to the centroid 70dc of the film surface 70fs. The distance between the centroid 70cc of the central portion 70c and the centroid 70dc of the film surface 70fs is, for example, not more than 1/10 of the second length L2.

The central portion 70c where the sensing unit 50u is provided is disposed at the central portion of the film surface 70fs. As shown in FIG. 1D, for example, a third length L3 of the central portion 70c in the first direction is not more than 0.3 times the first length L1. A fourth length L4 of the central portion 70c in the second direction is not more than 0.3 times the second length L2. The region other than the central portion 70c is used as the peripheral portion 70p.

In the pressure sensor 110 according to the embodiment, the planar configuration of the film part 70d (the configuration of the film surface 70fs) is an anisotropic configuration; and the sensing unit 50u is provided on the central portion 70c of such a film part 70d. Thereby, a highly-sensitive pressure sensor can be provided.

An example of the pressure sensor 110 will now be described.

The support unit 70s may include, for example, a substrate having a plate configuration. For example, a hollow portion 70h is provided in the interior of the substrate.

The support unit 70s may include, for example, a semiconductor material such as silicon, etc., a conductive material such as a metal, etc., or an insulating material. The support unit 70s may include, for example, silicon oxide, silicon nitride, etc. For example, the interior of the hollow portion 70h is in a reduced-pressure state (a vacuum state). A gas such as air, etc., or a liquid may be filled into the interior of the hollow portion 70h. The interior of the hollow portion 70h is designed such that the film part can deflect. The interior of the hollow portion 70h may communicate with external ambient air.

The film part 70d is provided on the hollow portion 70h. For example, a portion of the substrate used to form the support unit 70s that is patterned to be thin may be used as the film part 70d. The thickness (the length in the Z-axis direction) of the film part 70d is thinner than the thickness (the length in the Z-axis direction) of the substrate.

The film part 70d deflects when pressure is applied to the film part 70d. The pressure corresponds to the pressure to be sensed by the pressure sensor 110. The pressure that is applied also includes pressure due to sound waves, ultrasonic waves, etc. In the case where pressure due to sound waves, ultrasonic waves, etc., is sensed, the pressure sensor 110 functions as a microphone.

The film part 70d includes, for example, an insulating material. The film part 70d includes, for example, at least one selected from silicon oxide, silicon nitride, and silicon oxynitride. The film part 70d may include, for example, a semiconductor material such as silicon, etc. The film part 70d may include, for example, a metal material.

The thickness of the film part 70d is, for example, not less than 0.1 micrometer (μm) and not more than 3 μm. It is favorable for the thickness to be not less than 0.2 μm and not more than 1.5 μm. The film part 70d may include, for example, a stacked body of a silicon oxide film having a thickness of 0.2 μm and a silicon film having a thickness of 0.4 μm.

The first magnetic layer 10 and the second magnetic layer 20 include, for example, ferromagnetic layers. The first magnetic layer 10 is, for example, a magnetization free layer. The second magnetic layer 20 is, for example, a reference layer. A magnetization fixed layer or a magnetization free layer is used as the reference layer. For example, the change of the magnetization of the first magnetic layer 10 may be set to be easier than the change of the magnetization of the second magnetic layer 20. Thus, for example, as described below, the relative angle between the magnetization of the first magnetic layer 10 and the magnetization of the second magnetic layer 20 can be caused to change easily when the pressure is applied.

An example of the operations of the sensing element 50 will now be described. In the following example, the second magnetic layer 20 is a magnetization fixed layer.

In the pressure sensor 110 of the embodiment, strain occurs in the sensing element 50 when the film part 70d deflects due to the pressure from outside. The sensing element 50 functions to convert the change of the strain into a change of the electrical resistance.

The operation of the sensing element 50 functioning as a strain sensor is based on, for example, the application of an "inverse-magnetostriction effect" and a "magnetoresistance effect". The "inverse-magnetostriction effect" is obtained in the ferromagnetic layer included in the magnetization free layer. The "magnetoresistance effect" occurs in the stacked film of the reference layer, the spacer layer, and the magnetization free layer.

The "inverse-magnetostriction effect" is a phenomenon in which the magnetization of a ferromagnet is changed by the strain applied to the ferromagnet. In other words, the magnetization direction of the magnetization free layer changes when an external strain is applied to the stacked film of the sensing element 50. As a result, the relative angle between the magnetization of the reference layer and the magnetization of the magnetization free layer changes. In such a case, the change of the electrical resistance is caused by a "magnetoresistance effect (MR effect)". The MR effect includes, for example, a GMR (Giant magnetoresistance) effect, a TMR (Tunneling magnetoresistance) effect, etc. The MR effect occurs by causing a current to flow in the stacked film and by reading the change of the relative angle of the orientation of the magnetization as the electrical resistance change. For example, strain is applied to the sensing element 50 by strain being applied to the stacked film. Due to the strain, the orientation of the magnetization of the magnetization free layer changes; and the relative angle between the orientation of the magnetization of the magnetization free layer and the orientation of the magnetization of the reference layer changes. In other words, the MR effect occurs due to the inverse-magnetostriction effect.

In the case where the ferromagnetic material of the magnetization free layer has a positive magnetostriction constant, the direction of the magnetization changes such that the angle between the direction of the magnetization and the direction of the tensile strain becomes small and the angle between the direction of the magnetization and the direction of the compressive strain becomes large. In the case where the ferromagnetic material of the magnetization free layer has a negative magnetostriction constant, the direction of the magnetization changes such that the angle between the direction of the magnetization and the direction of the tensile strain becomes large and the angle between the direction of the magnetization and the direction of the compressive strain becomes small.

An example of the change of the magnetization will now be described for the case where the ferromagnetic material of the magnetization free layer has a positive magnetostriction constant.

FIG. 2A to FIG. 2I are schematic perspective views illustrating operations of the pressure sensor.

Figures 2A, 2B, 2C:
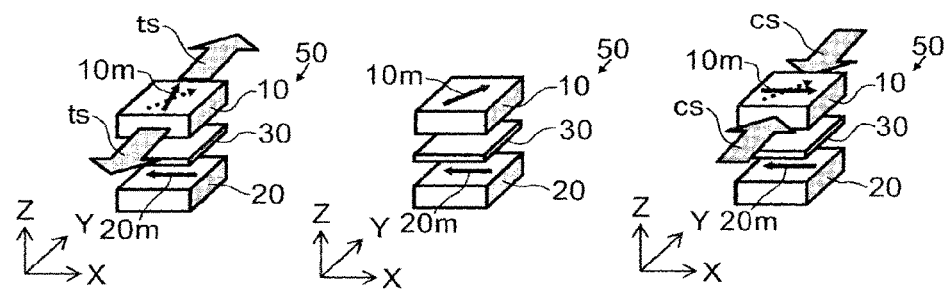
FIG. 2A to FIG. 2I are schematic perspective views illustrating operations of the pressure sensor.

FIG. 2A to FIG. 2C illustrate states in which a "strain in the perpendicular direction" is applied to the sensing element 50. The "strain in the perpendicular direction" is a strain that is anisotropic (hereinbelow, called anisotropic strain) in a direction perpendicular to the stacking direction (e.g., the direction from the second magnetic layer 20 toward the first magnetic layer 10) and perpendicular to the direction of the magnetization of the magnetization fixed layer.

Figures 2D, 2E, 2F:
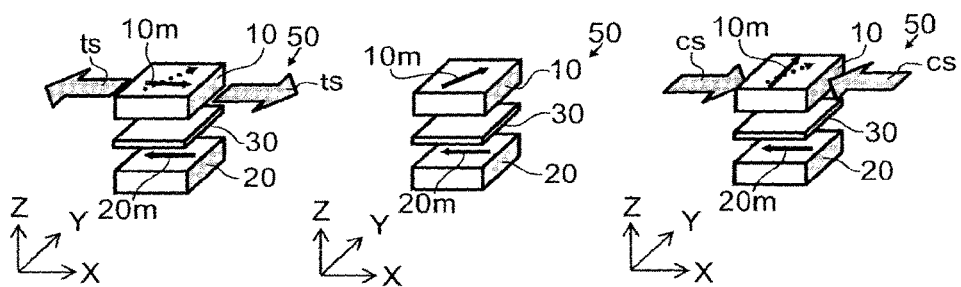

FIG. 2D to FIG. 2F illustrate states in which a "strain in the parallel direction" is applied to the sensing element 50. The "strain in the parallel direction" is strain that is anisotropic (anisotropic strain) in a direction perpendicular to the stacking direction and parallel to the direction of the magnetization of the magnetization fixed layer.

Figures 2G, 2H, 2I:
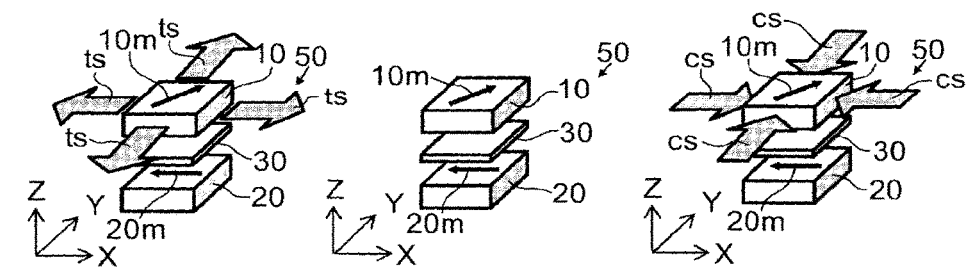

FIG. 2G to FIG. 2I illustrate states in which an "isotropic strain" is applied to the sensing element 50. The "isotropic strain" is an isotropic strain in a plane perpendicular to the stacking direction.

FIG. 2B, FIG. 2E, and FIG. 2H correspond to states in which the strain is not applied. FIG. 2A, FIG. 2D, and FIG. 2G correspond to states in which a tensile strain ts is applied. FIG. 2C, FIG. 2F, and FIG. 2I correspond to states in which a compressive strain cs is applied.

In the case where the tensile strain ts is applied as "strain in the perpendicular direction" as illustrated in FIG. 2A, the angle (the relative angle of the magnetizations) between the direction of a magnetization 10m of the magnetization free layer (the first magnetic layer 10) and the direction of a magnetization 20m of the magnetization fixed layer (the second magnetic layer 20) becomes smaller than that in the state in which the strain is not applied (the state of FIG. 2B). As a result, the electrical resistance of the sensing element 50 decreases.

In the case where the compressive strain cs is applied as "strain in the perpendicular direction" as illustrated in FIG. 2C, the relative angle of the magnetization becomes larger than that in the state in which the strain is not applied (the state of FIG. 2B). As a result, the electrical resistance increases.

In the case where the tensile strain ts is applied as "strain in the parallel direction" as illustrated in FIG. 2D, the relative angle of the magnetization becomes larger than that in the state in which the strain is not applied (the state of FIG. 2E). As a result, the electrical resistance of the sensing element 50 increases.

In the case where the compressive strain cs is applied as "strain in the parallel direction" as illustrated in FIG. 2F, the relative angle of the magnetization becomes smaller than that in the state in which the strain is not applied (the state of FIG. 2E). As a result, the electrical resistance of the sensing element 50 decreases.

Thus, the relationship of the increase or decrease of the relative angle of the magnetization with respect to the strain for the "strain in the parallel direction" is the reverse of the relationship for the strain in the perpendicular direction. The change of the electrical resistance with respect to the polarity of the strain has the reverse polarity between the "strain in the parallel direction" and the "strain in the perpendicular direction".

In the case where the "isotropic strain" is applied as illustrated in FIG. 2G to FIG. 2I, the direction of the magnetization 10m of the magnetization free layer does not change. Therefore, the electrical resistance does not change for the strain of the two polarities of the tensile strain ts and the compressive strain cs.

Thus, in the sensing element 50, the change of the electrical resistance that is obtained is different according to the orientation of the strain that is applied.

In the pressure sensor 110 according to the embodiment, the planar configuration of the film part 70d is an anisotropic configuration. For example, the length (the first length L1) of the film part 70d along a first axis 70x (an axis in the film surface 70fs) passing through the centroid 70dc of the film surface 70fs is longer than the length (the second length L2) of the film part 70d along a second axis 70y orthogonal to the first axis 70x and passing through the centroid 70dc of the film surface 70fs. The sensing unit 50u is disposed in the central portion 70c (proximal to the centroid 70dc). For example, the multiple sensing elements 50 are provided together proximally to the centroid 70dc of the film surface 70fs.

FIG. 3A to FIG. 3C are schematic views illustrating the operation of the pressure sensor according to the first embodiment.

FIG. 3A is a schematic perspective view of the film part 70d of the pressure sensor 110 according to the embodiment. FIG. 3B is a cross-sectional view along line A1-A2 of FIG. 3A. FIG. 3C is a cross-sectional view along line B1-B2 of FIG. 3A. FIG. 3B and FIG. 3C illustrate the state in which the pressure is applied to the film part 70d and the film part 70d deforms and deflects.

As shown in FIG. 3A, the planar configuration of the film part 70d is, for example, an anisotropic configuration such as a rectangle, etc. The dotted lines in FIG. 3B and FIG. 3C schematically illustrate the state of the film part 70d when the pressure is not applied. For example, the film part 70d is parallel to the X-Y plane when the pressure is not applied. The solid lines in FIG. 3B and FIG. 3C schematically illustrate the state of the film part 70d when pressure Fz is applied to the film part 70d. As illustrated in these drawings, the film part 70d deflects when the pressure Fz is applied to one surface of the film part 70d. At this time, the strain occurring in the surface of the film part 70d is different between the major-axis direction and the minor-axis direction. The strain occurring in the minor-axis direction is larger than the strain occurring in the major-axis direction. This is because the curvature radius in the minor-axis direction is smaller than the curvature radius in the major-axis direction for the surface of the film part 70d that is deformed.

Thus, in the case where the planar configuration of the film part 70d is the anisotropic configuration, the strain occurring in the film part 70d is different between the major-axis direction (the first direction) and the minor-axis direction (the second direction). Therefore, in the pressure sensor 110, an anisotropic strain is obtained also in the central portion 70c (the vicinity of the centroid 70dc) of the film surface 70fs. In the embodiment, the anisotropic strain is obtained in a wide region on the film part 70d.

FIG. 4A to FIG. 4C are schematic views illustrating the operation of a pressure sensor of a reference example.

FIG. 4A is a schematic perspective view of the film part 70d of the pressure sensor 119 of the reference example. FIG. 4B is a cross-sectional view along line A1-A2 of FIG. 4A. FIG. 4C is a cross-sectional view along line B1-B2 of FIG. 4A. FIG. 4B and FIG. 4C illustrate the state in which the pressure is applied to the film part 70d and the film part 70d deforms and deflects.

In the pressure sensor 119 of the reference example as shown in FIG. 4A, the planar configuration of the film part 70d is isotropic, e.g., in the example, a circle. In such a case, as illustrated in FIG. 4B and FIG. 4C, the strain occurring in the surface of the film part 70*d* is isotropic when the pressure Fz is applied and the film part 70*d* deforms. Accordingly, in the pressure sensor 119 of the reference example, the strain occurring in the surface is isotropic at the centroid 70*dc* vicinity of the film surface 70*fs*.

In other words, the region where the anisotropic strain occurs on the film part 70*d* is wider for the film part 70*d* (the pressure sensor 110) having the anisotropic configuration than for the film part 70*d* (the pressure sensor 119) having the isotropic configuration.

The sensing element 50 is disposed on the film part 70*d*. When the film part 70*d* deflects due to the external pressure, the strain is applied to the sensing element 50; and as a result, in the sensing element 50, the external pressure is sensed as the change of the electrical resistance. As described above, in the sensing element 50, the change of the electrical resistance with respect to the strain is different according to the direction of the strain applied to the sensing element 50. By providing the sensing element 50 on the film part 70*d* having the anisotropic configuration, the surface area of the region where the anisotropic strain is applied to the sensing element 50 can be increased. For example, the anisotropic strain can be large by using the film part 70*d* having the anisotropic configuration. Further, the degrees of freedom of the disposition of the sensing element 50 increase because the surface area of the region of the film part 70*d* where the anisotropic strain is applied can be increased. Further, because the surface area can be increased, the number of the sensing elements 50 that can be disposed in the region can be increased. For example, the number of the sensing elements having a similar change of electrical resistance (e.g., having the same polarity) due to the pressure can be increased. According to the embodiment, the sensing sensitivity of the pressure can be increased.

FIG. 5A to FIG. 5F are schematic views illustrating the configuration and characteristics of the pressure sensor according to the first embodiment.

Figure 5A:
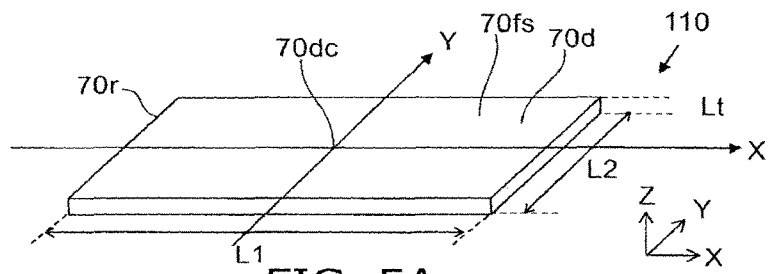
FIG. 5A to FIG. 5F are schematic views illustrating the configuration and characteristics of the pressure sensor according to the first embodiment.
Figure 5B:
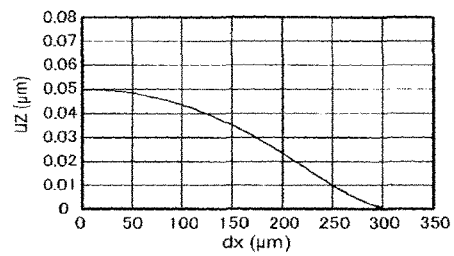
Figure 5C:
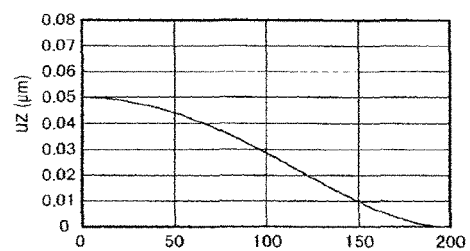

These drawings illustrate simulation results of characteristics of the pressure sensor 110. FIG. 5A is a schematic perspective view of the film part 70*d*. FIG. 5B and FIG. 5C illustrate the deflection amount uz of the film part 70*d* when the pressure is applied to the film part 70*d*. In FIG. 5B and FIG. 5C, the vertical axis is the deflection amount uz (μm). The horizontal axis of FIG. 5B is a position dx (μm) in the X-axis direction. The horizontal axis of FIG. 5C is a position dy (μm) in the Y-axis direction. The references of the position dx and the position dy are the centroid 70*dc* of the film surface 70*fs*.

Figure 5D:
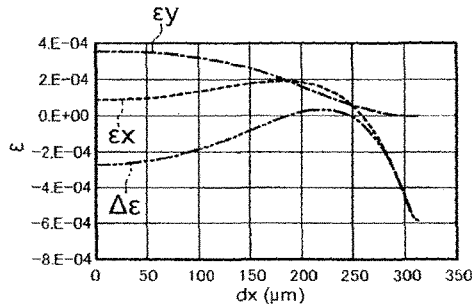
Figure 5E:
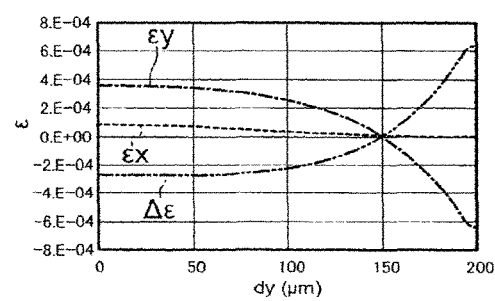

FIG. 5D and FIG. 5E illustrate strain ε occurring in the film part 70*d* to which the pressure is applied. In FIG. 5D and FIG. 5E, the vertical axis is the strain ε (no units). The horizontal axis of FIG. 5D is the position dx; and the horizontal axis of FIG. 5E is the position dy. In these drawings, the strain ε is positive for tensile strain; and the strain ε is negative for compressive strain. These drawings show a first strain εx which is the strain in the X-axis direction, a second strain εy which is the strain in the Y-axis direction, and the difference (an anisotropic strain Δε) between the first strain εx and the second strain εy. The anisotropic strain Δε is the difference (i.e., εx−εy) between the first strain εx and the second strain εy. The anisotropic strain Δε contributes to the change of the direction of the magnetization of the magnetization free layer of the sensing element 50.

Figure 5F:
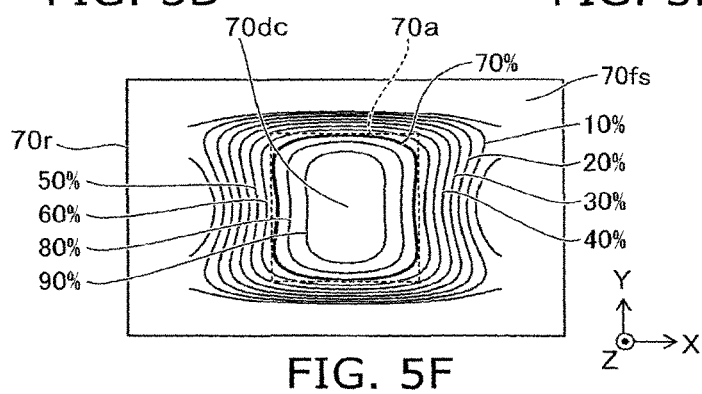

FIG. 5F illustrates the distribution in the X-Y plane of the anisotropic strain Δε occurring in the film part 70*d*.

In the example as shown in FIG. 5A, the planar configuration of the film part 70*d* is a rectangle. The sensing elements 50 (not-shown in the drawing) are disposed at the centroid 70*dc* vicinity of the film surface 70*fs*. In the example, the length (the first length L1) of the long side of the film part 70*d* is 625 μm. The length (the second length L2) of the short side is 400 μm. A thickness Lt of the film part 70*d* is 2 μm.

In the example, the outer edge 70*r* of the film part 70*d* is set to be a fixed end that is completely constrained. In the example, analysis of the strain occurring in the front surface of the film part 70*d* is performed by finite element analysis. The analysis is performed by applying Hooke's law to each of the components subdivided by the finite element method.

In the simulation, the material of the film part 70*d* is assumed to be silicon. The Young's modulus of the film part 70*d* is 165 GPa; and the Poisson's ratio of the film part 70*d* is 0.22. The simulation determines the strain ε of the front surface of the film part 70*d* when a uniform pressure of 13.33 kPa is applied from the back surface of the film part 70*d*. In the finite element method, the planar mesh size in the X-Y plane is 5 μm; and the mesh size in the thickness direction is 2 μm.

In the major-axis direction and the minor-axis direction as shown in FIG. 5B and FIG. 5C, the film part 70*d* at the centroid 70*dc* vicinity of the film surface 70*fs* has a convex configuration (an upward protrusion). At the outer edge 70*r* vicinity of the film part 70*d*, the film part 70*d* has a concave configuration (a downward protrusion). The concave configuration at the outer edge 70*r* vicinity is due to the warp at the fixed end vicinity. Tensile strain occurs in the front surface of the film part 70*d* (the diaphragm) in the region where the film part 70*d* is warped in the convex configuration. Conversely, compressive strain occurs in the front surface of the film part 70*d* in the region where the warped is in the concave configuration.

As shown in FIG. 5D and FIG. 5E, the first strain εx and the second strain εy are tensile strains at the centroid 70*dc* where the warp is in the convex configuration. The first strain εx and the second strain εy are compressive strains at the outer edge 70*r* vicinity where the warp is in the concave configuration. The anisotropic strain Δε at the centroid 70*dc* is in compression; and compressive strain in the major-axis direction (the X-axis direction) exists. In other words, tensile anisotropic strain exists in the minor-axis direction (the Y-axis direction). Anisotropic strain that is similar to the anisotropic strain obtained at the centroid 70*dc* exists in a wide area from the centroid 70*dc* to the outer edge 70*r* of the film surface 70*fs*.

FIG. 5F illustrates the results of the analysis of the anisotropic strain Δε shown in FIG. 5D and FIG. 5E for the entire surface of the film part 70*d*. In the contour diagram shown in FIG. 5F, the lines labeled with the characters "10%" to "90%" respectively illustrate the positions where the anisotropic strain Δε is 10% to 90% of the value (the absolute value) of the anisotropic strain Δε at the centroid 70*dc*. It can be seen from FIG. 5F that an anisotropic strain Δε that is equivalent to that of the centroid 70*dc* (not less than 70% of the value at the centroid 70*dc*) can be obtained in a wide region at the centroid 70*dc* vicinity by using the film part 70*d* having the anisotropic configuration. In the embodiment, the sensing element 50 (the multiple sensing elements 50) can be disposed in the area where the equivalent anisotropic strain Δε is obtained. Thereby, a highly-sensitive pressure sensor is obtained.

An anisotropic strain occurrence region 70*a* is the region where the anisotropic strain is substantially 0.7 times (70% of) the value of the maximum anisotropic strain Δε obtained in the film part 70d. In the example shown in FIG. 5D, the maximum anisotropic strain Δε is obtained at the centroid 70dc. The anisotropic strain occurrence region 70a is the region on the inner side of the line labeled with the characters "70%" illustrated in FIG. 5F.

In the case where the planar configuration of the film part 70d is a rectangle as shown in FIG. 5F, the configuration of the anisotropic strain occurrence region 70a also substantially is a rectangle. The anisotropic strain occurrence region 70a is caused to correspond to the central portion 70c of the embodiment.

It can be seen from FIG. 5F that the centroid 70dc of the film surface 70fs substantially overlaps the centroid of the anisotropic strain occurrence region 70a. For example, the distance between the centroid 70dc of the film surface 70fs and the centroid of the anisotropic strain occurrence region 70a is, for example, not more than 1/10 of the second length L2.

Then, for example, the length of the anisotropic strain occurrence region 70a in the X-axis direction (corresponding to the third length L3 of the central portion 70c in the first direction) is not more than 0.3 times the first length L1. The length of the anisotropic strain occurrence region 70a in the Y-axis direction (corresponding to the fourth length L4 of the central portion 70c in the second direction) is not more than 0.3 times the second length L2.

In the embodiment, the sensing element 50 is disposed in such an anisotropic strain occurrence region 70a. For example, the centroid of the sensing element 50 overlaps the anisotropic strain occurrence region 70a when the sensing element 50 is projected onto the X-Y plane. In the case where multiple sensing elements 50 are provided, the centroids of the multiple sensing elements 50 overlap the anisotropic strain occurrence region 70a when projected onto the X-Y plane. Thereby, a highly-sensitive pressure sensor can be provided.

FIG. 6A to FIG. 6D are schematic views illustrating the configuration and characteristics of a pressure sensor of a reference example.

These drawings illustrate simulation results of characteristics of the pressure sensor 119a of the reference example. In the pressure sensor 119a, the first length L1 of the film part 70d is 500 μm; and the second length L2 also is 500 μm. In other words, the planar configuration of the film part 70d is a square. Otherwise, the pressure sensor 119a is similar to the pressure sensor 110. The conditions of the simulation also are similar to those of the pressure sensor 110.

FIG. 6A is a schematic perspective view of the film part 70d. In FIG. 6B, the vertical axis is the deflection amount uz; and the horizontal axis is the position dx (μm). In FIG. 6C, the vertical axis is the strain ε (no units); and the horizontal axis is the position dx. In the example, the planar configuration of the film part 70d is a square; and the characteristics in the Y-axis direction are the same as the characteristics in the X-axis direction. FIG. 6D shows the anisotropic strain Δε. In the example, there are no contours illustrated in the contour diagram of FIG. 6D because anisotropic strain is not obtained at the centroid 70dc vicinity.

As shown in FIG. 6B, the film part 70d has a convex configuration at the centroid 70dc vicinity of the film surface 70fs; and the film part 70d has a concave configuration at the outer edge 70r vicinity.

As shown in FIG. 6C, the first strain εx and the second strain εy are tensile strains at the centroid 70dc where the warp is in the convex configuration and compressive strains at the outer edge 70r vicinity where the warp is in the concave configuration. The anisotropic strain Δε at the centroid 70dc is zero. This is because the square film part 70d is isotropic in the X-Y plane.

Therefore, as shown in FIG. 6D, the region where the anisotropic strain is obtained does not exist at the centroid 70dc vicinity. Accordingly, in the pressure sensor 119a, the change of the electrical resistance cannot be obtained even in the case where the sensing element 50 is disposed at the centroid 70dc vicinity of the film surface 70fs.

As described above, the anisotropic strain cannot be obtained at the centroid 70dc vicinity in the square film part 70d (the pressure sensor 119a) that is isotropic in the X-Y plane. Conversely, the anisotropic strain Δε can be obtained in a wide region at the centroid 70dc vicinity in the rectangular film part 70d (the pressure sensor 110) having the anisotropic configuration in the X-Y plane. Thus, the configuration to obtain the anisotropic strain in a large surface area of the central portion 70c including the centroid 70dc was discovered. In the embodiment, the film part 70d having the anisotropic configuration is used. Then, stress can be sensed with high sensitivity by disposing the sensing element 50 in the central portion 70c of the film part 70d.

For example, similar anisotropic strains are applied to the multiple sensing elements 50 by disposing the multiple sensing elements 50 at the centroid 70dc vicinity of the rectangular film part 70d having the anisotropic configuration. Therefore, multiple sensing elements 50 having a similar change of electrical resistance (e.g., having the same polarity) due to the pressure can be obtained. For example, the S/N ratio can be increased by connecting the sensing elements 50 electrically in series. Further, a highly-sensitive pressure sensor can be provided by setting the bias voltage to be an appropriate value.

An example of the characteristics of the pressure sensor will now be described in more detail.

Figure 7:
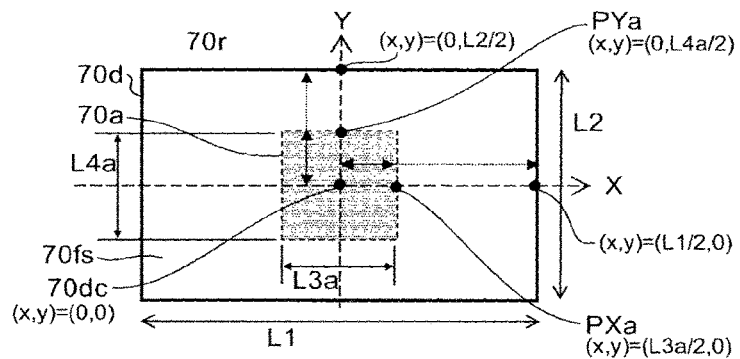
FIG. 7 is a schematic plan view illustrating the pressure sensor.

FIG. 7 is a schematic plan view illustrating the pressure sensor.

FIG. 7 illustrates a coordinate system of the film part 70d of the pressure sensor 110. In the example, the planar configuration of the film part 70d is a rectangle. In other words, the first length L1 (the length in the X-axis direction) is longer than the second length L2 (the length in the Y-axis direction). The coordinates (x, y) of the centroid of the film surface 70fs are taken to be (0, 0). The coordinates of one point of the outer edge 70r of the film part 70d in the X-axis direction are (L1/2, 0). The coordinates of one point of the outer edge 70r of the film part 70d in the Y-axis direction are (0, L2/2).

In the case where the planar configuration of the film part 70d is a rectangle, the planar configuration of the anisotropic strain occurrence region 70a also is a rectangle. The length in the first direction (the length in the X-axis direction) of the anisotropic strain occurrence region 70a is a length L3a; and the length in the second direction (the length in the Y-axis direction) of the anisotropic strain occurrence region 70a is a length L4a. The coordinates of one point PXa in the X-axis direction of the outer edge of the anisotropic strain occurrence region 70a are (L3a/2, 0). The coordinates of one point PYa in the Y-axis direction of the outer edge of the anisotropic strain occurrence region 70a are (0, L4a/2).

An example of the characteristics for different aspect ratios AR of the film part 70d for the case where the planar configuration of the film part 70d is such a rectangle will now be described. The aspect ratio AR is the ratio of the second length L2 to the first length L1 (i.e., AR=L2/L1).

FIG. 8A to FIG. 8D are graphs illustrating characteristics of the pressure sensors.

These drawings show the characteristics for the pressure sensors having the first to sixth configurations recited below.

In the first configuration, the first length L1 is 2500 μm; the second length L2 is 100 μm; and the aspect ratio AR is 0.04.

In the second configuration, the first length L1 is 1580 μm; the second length L2 is 158 μm; and the aspect ratio AR is 0.1.

In the third configuration, the first length L1 is 1000 μm; the second length L2 is 250 μm; and the aspect ratio AR is 0.25.

In the fourth configuration, the first length L1 is 625 μm; the second length L2 is 400 μm; and the aspect ratio AR is 0.64. The fourth configuration corresponds to the configuration described in regard to FIG. 5A to FIG. 5F.

In the fifth configuration, the first length L1 is 560 μm; the second length L2 is 448 μm; and the aspect ratio AR is 0.8.

In the sixth configuration, the first length L1 is 500 μm; the second length L2 is 500 μm; and the aspect ratio AR is 1. The sixth configuration corresponds to the configuration described in regard to FIG. 6A to FIG. 6D.

The surface area of the film part 70d is constant at 250,000 μm² for each of these configurations.

For these configurations, analysis of the strain occurring in the front surface of the film part 70d is performed by finite element analysis. The conditions of the finite element method are the same as the conditions described in regard to FIG. 5A to FIG. 5F.

Figure 8A:
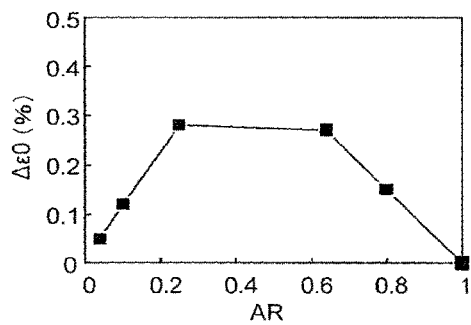
FIG. 8A to FIG. 8D are graphs illustrating characteristics of the pressure sensors.

The vertical axis of FIG. 8A is an anisotropic strain Δε0 (the absolute value of the anisotropic strain) at the centroid 70dc of the film surface 70fs. The horizontal axis is the aspect ratio AR of the planar configuration of the film part 70d (the configuration of the film surface 70fs). FIG. 8A shows the characteristics of the first to sixth configurations.

As shown in FIG. 8A, for the sixth configuration for which the aspect ratio AR is 1, the anisotropic strain Δε0 at the centroid 70dc is zero; and the anisotropic strain does not occur.

Conversely, for the first to fifth configurations for which the aspect ratio AR is less than 1, the absolute value of the anisotropic strain Δε0 is greater than 0. In other words, the anisotropic strain is obtained at the centroid 70dc. From this result, it can be seen that a highly-sensitive pressure sensor is obtained by providing the sensing element 50 at the centroid 70dc vicinity in the case where the aspect ratio AR is less than 1 and the film part 70d has an anisotropic configuration.

It can be seen from FIG. 8A that the anisotropic strain Δε0 having a large absolute value is obtained when the aspect ratio AR is not less than 0.1 and not more than 0.8. The anisotropic strain Δε0 having an even larger absolute value is obtained when the aspect ratio AR is not less than 0.25 and not more than 0.64. From the aspect of obtaining the anisotropic strain Δε0 having a large absolute value at the centroid 70dc, it is favorable for the aspect ratio AR to be not less than 0.1 and not more than 0.8, and more favorable to be not less than 0.25 and not more than 0.64.

In the first to fifth configurations as well, it was found that the configuration of the region (the anisotropic strain occurrence region 70a) where the anisotropic strain is equivalent to the centroid 70dc is a rectangle similarly to the description regarding FIG. 5D.

The ratio of the surface area of the anisotropic strain occurrence region 70a to the surface area of the film part 70d is a surface area ratio Ra. In the example, the surface area of the anisotropic strain occurrence region 70a is the product of the length L3a and the length L4a. The surface area of the film part 70d is the product of the first length L1 and the second length L2.

Figure 8B:
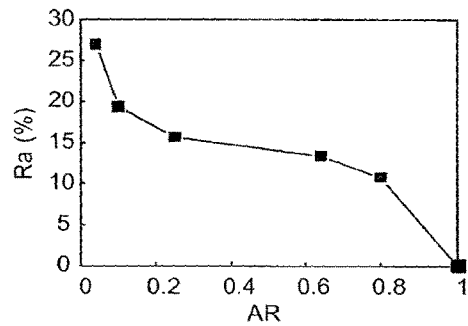

In FIG. 8B, the vertical axis is the surface area ratio Ra; and the horizontal axis is the aspect ratio AR.

It can be seen from FIG. 8B that for the square film part 70d (the sixth configuration) for which the aspect ratio is 1, the surface area ratio Ra is zero; and there is no region at the centroid 70dc vicinity where the anisotropic strain is obtained. Conversely, for the rectangular film parts 70d for which the aspect ratio AR is less than 1, the surface area ratio Ra is greater than zero. In other words, a region exists at the centroid 70dc vicinity where the anisotropic strain is obtained. The surface area ratio Ra increases as the aspect ratio AR decreases (the difference between the first length L1 and the second length L2 increases). From the aspect of widening the region on the film part 70d where the anisotropic strain is obtained, it is favorable for the aspect ratio AR to be not more than 0.64, and more favorable to be not more than 0.25.

The position of the outer edge of the anisotropic strain occurrence region 70a (the coordinates referring to FIG. 7) will now be described.

Figure 8C:
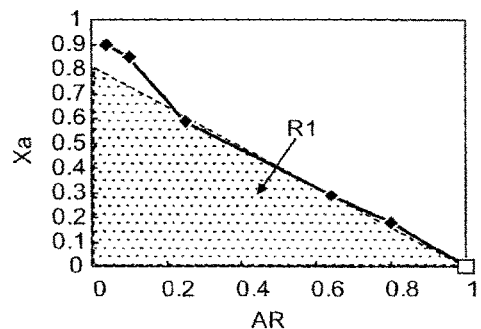

The vertical axis of FIG. 8C is the normalized coordinate (a distance Xa) of the one point PXa of the outer edge of the anisotropic strain occurrence region 70a in the X-axis direction. The distance Xa corresponds to (L3a)/(L1).

Figure 8D:
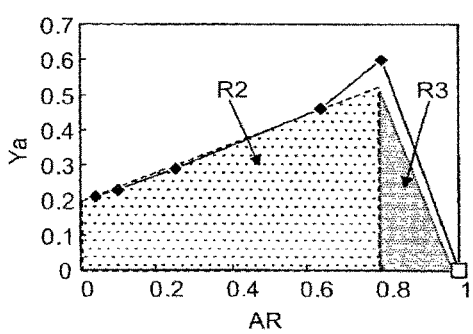

The vertical axis of FIG. 8D is the normalized coordinate (a distance Ya) of the one point PYa of the outer edge of the anisotropic strain occurrence region 70a in the Y-axis direction. The distance Ya corresponds to (L4a)/(L2).

In these drawings, the horizontal axis is the aspect ratio AR.

When the aspect ratio AR is 1 (the sixth configuration), the anisotropic strain occurrence region 70a does not exist. The distance Xa and the distance Ya are zero for this case for convenience in FIG. 8C and FIG. 8D.

In the case where the aspect ratio AR is less than 1 as shown in FIG. 8C and FIG. 8D, the distance Xa and the distance Ya are larger than zero; and the anisotropic strain occurrence region 70a is obtained.

It can be seen from these drawings that in the case where the aspect ratio AR is not less than 0.8 but less than 1, it is favorable to have the ranges $$|Xa| \le (L1/2) \times \{-0.8 \times (L2/L1) + 0.8\}, \text{ and}$$

$$|Ya| \le (L2/2) \times \{-2.5 \times (L2/L1) + 2.5\}.$$

On the other hand, in the case where the aspect ratio AR is less than 0.8, it is favorable to have the ranges $$|Xa| \le (L1/2) \times \{-0.8 \times (L2/L1) + 0.8\}, \text{ and}$$

$$|Ya| \le (L2/2) \times \{0.375 \times (L2/L1) + 0.2\}.$$

Namely, a first hatching region R1 that is illustrated by the light hatching in FIG. 8C corresponds to the conditions of the anisotropic strain occurrence region 70a. The first hatching region R1 is represented by first formula recited below.

$$Xa \le -0.8 AR + 0.8 \tag{1}$$

Because the distance Xa is L3a/L1 and AR is L2/L1, the second formula recited below is obtained.

$$L3a \le L1\{-0.8 \times (L2/L1) + 0.8\} \tag{2}$$

On the other hand, in FIG. 8D, a second hatching region R2 that is illustrated by the light hatching or a third hatching region R3 that is illustrated by the dark hatching corresponds to the conditions of the anisotropic strain occurrence region 70a. The second hatching region R2 is represented by third formula recited below.

$$Ya \leq 0.375 AR + 0.2 \quad (3)$$

Because the distance Ya is L4a/L2 and AR is L2/L1, the fourth formula recited below is obtained.

$$L4a \leq L2\{0.375AR + 0.2\} \quad (4)$$

The third hatching region R3 is represented by fifth formula recited below.

$$Ya \leq -2.5AR + 2.5 \quad (5)$$

Accordingly, the sixth formula recited below is obtained.

$$L4a \leq L2\{-2.5AR + 2.5\} \quad (6)$$

In other words, in the case where the aspect ratio AR is not less than 0.8 but less than 1, the conditions of the first formula, the second formula, the fifth formula, and the sixth formula are favorable.

On the other hand, in the case where the aspect ratio AR is less than 0.8, the conditions of the first formula, the second formula, the third formula, and the fourth formula are favorable.

In the embodiment, for example, the central portion 70c is set to correspond to the anisotropic strain occurrence region 70a. In other words, the third length L3 of the central portion 70c is set to correspond to the length L3a of the anisotropic strain occurrence region 70a; and the fourth length L4 of the central portion 70c is set to correspond to the length L4a of the anisotropic strain occurrence region 70a. The outer edge 70r of the central portion 70c is set to be the outer edge of the anisotropic strain occurrence region 70a.

Accordingly, in the case where the aspect ratio AR (L2/L1) is not less than 0.8 but less than 1, the central portion 70c is set to satisfy the seventh formula recited below.

$$L3 = L1 \times \{-0.8 \times (L2/L1) + 0.8\} \quad (7)$$

In such a case, the third length L3 may be set to be substantially equal to the right side of the seventh formula. In other words, the third length L3 is set to be not less than 0.8 times and not more than 1.2 times the right side of the seventh formula.

In other words, in the case where the aspect ratio AR (L2/L1) is not less than 0.8 but less than 1, it is favorable for the third length L3 to be not less than 0.8 times and not more than 1.2 times $L1 \times \{-0.8 \times (L2/L1) + 0.8\}$.

Similarly, in the case where the aspect ratio AR (L2/L1) is not less than 0.8 but less than 1, the central portion 70c is set to satisfy the eighth formula recited below.

$$L4 = L2 \times \{-2.5 \times (L2/L1) + 2.5\} \quad (8)$$

In such a case as well, the fourth length L4 may be set to be substantially equal to the right side of the eighth formula. In other words, the fourth length L4 is set to be not less than 0.8 times and not more than 1.2 times the right side of the eighth formula.

In other words, in the case where the aspect ratio AR (L2/L1) is not less than 0.8 but less than 1, it is favorable for the fourth length L4 to be not less than 0.8 times and not more than 1.2 times $L2 \times \{-2.5 \times (L2/L1) + 2.5\}$.

On the other hand, in the case where the aspect ratio AR (L2/L1) is less than 0.8, the ninth formula and the tenth formula recited below are obtained.

$$L3 = L1 \times \{-0.8 \times (L2/L1) + 0.8\} \quad (9)$$

$$L4 = L2 \times \{0.375 \times (L2/L1) + 0.2\} \quad (10)$$

Accordingly, in the case where the aspect ratio AR (L2/L1) is less than 0.8, it is favorable for the third length to be not less than 0.8 times and not more than 1.2 times $L1 \times \{-0.8 \times (L2/L1) + 0.8\}$. Also, it is favorable for the fourth length L4 to be not less than 0.8 times and not more than 1.2 times $L2 \times \{0.375 \times (L2/L1) + 0.2\}$.

By satisfying such conditions, a larger anisotropic strain is obtained; and a highly-sensitive pressure sensor is obtained more reliably.

Even when the thickness Lt of the film part 70d is changed in the case where the planar configuration of the film part 70d is a rectangle, the characteristics of the anisotropic strain occurrence region 70a are similar to the characteristics described in regard to FIG. 8A to FIG. 8D. For example, at least in the case where the thickness Lt of the film part 70d is not less than 0.01 μm and not more than 20 μm, it is favorable for the settings to substantially satisfy the seventh to tenth formulas. In the embodiments described below as well, similar results are obtained in the case where the thickness Lt of the film part 70d is changed.

An example of the characteristics for different materials of the film part 70d in the case where the planar configuration of the film part 70d is a rectangle will now be described. The Young's modulus is different for different materials. In the example, the characteristics are simulated by changing the Young's modulus of the film part 70d.

Figure 9A:
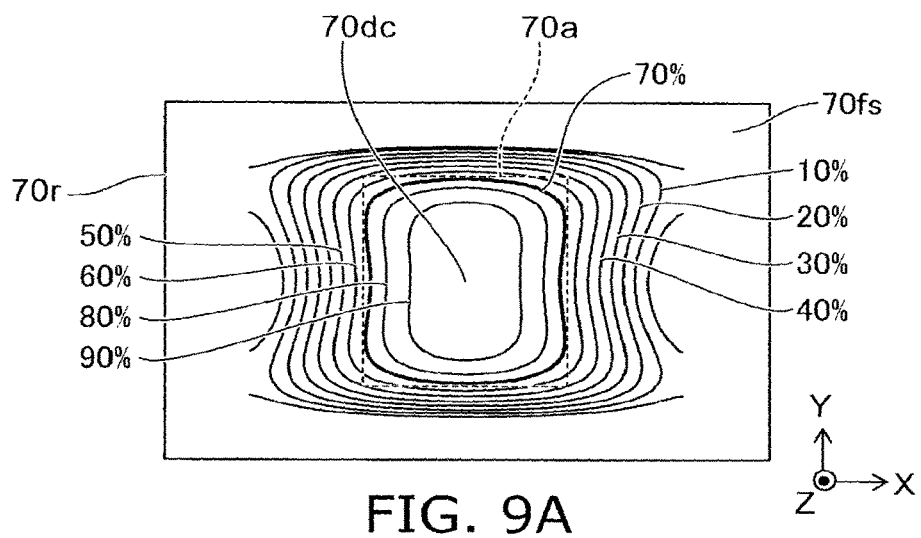
FIG. 9A and FIG. 9B are graphs illustrating characteristics of the pressure sensor.
Figure 9B:
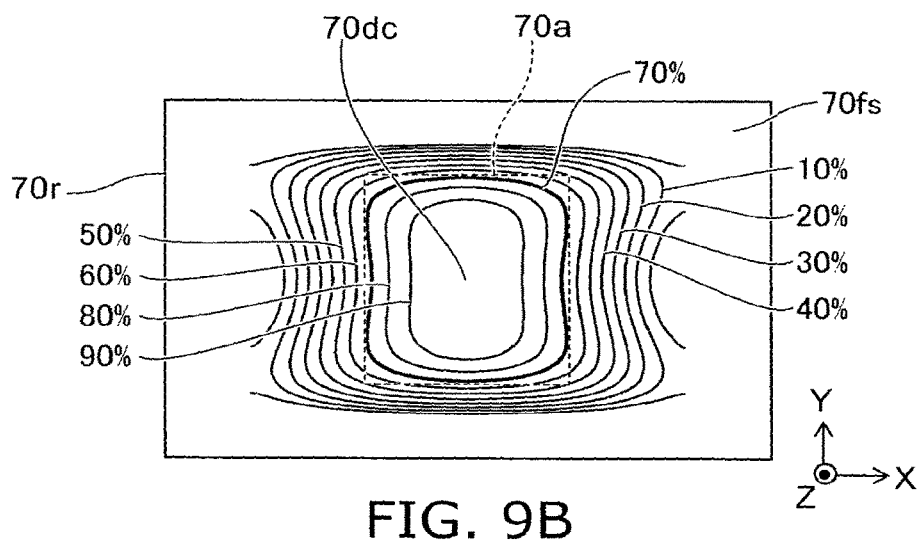

FIG. 9A and FIG. 9B are graphs illustrating characteristics of the pressure sensor. In the contour diagram of FIG. 9A and FIG. 9B, the lines labeled with the characters of "10%" to "90%" respectively illustrate the positions where the anisotropic strain Δε is 10% to 90% of the value (the absolute value) of the anisotropic strain Δε at the centroid 70dc. These illustrations also are similar for the contour diagrams described below.

FIG. 9A illustrates the results calculated for the anisotropic strain occurrence region 70a for the case where the Young's modulus of the film part 70d is 0.01 GPa. The value of the Young's modulus corresponds to the case where the material of the film part 70d is rubber. FIG. 9B illustrates the results calculated for the anisotropic strain occurrence region 70a for the case where the Young's modulus of the film part 70d is 1200 GPa. The value corresponds to the case where the material of the film part 70d is diamond. Other than the Young's modulus, the calculation conditions are similar to the conditions of the results of FIG. 5A to FIG. 5F.

Even in the case of the calculation using the Young's modulus of 0.01 GPa or 1200 GPa as shown in FIG. 9A and FIG. 9B, it can be seen that the calculation results for the anisotropic strain occurrence region 70a of the film part 70d are equivalent to the calculation results for 165 GPa shown in FIG. 5F.

Thus, even in the case where the material of the film part 70d is changed, the characteristics of the anisotropic strain occurrence region 70a are similar to the characteristics described in regard to FIG. 8A to FIG. 8D. Accordingly, at least in the case where the Young's modulus of the film part 70d is not less than 0.01 GPa and not more than 1200 GPa, it is favorable for the settings to substantially satisfy the seventh to tenth formulas.

As described above, FIG. 9A and FIG. 9B show examples in which the film parts 70d have different Young's moduli. In the case where the film parts 70d have different Poisson's ratios as well, similar anisotropic strain occurrence regions 70a can be obtained. In the embodiments described below as well, a similar anisotropic strain occurrence region 70a can be obtained even in the case where at least one selected from the Young's modulus and the Poisson's ratio of the film part 70d is changed.

In the embodiment, the planar configuration of the film part 70d is not limited to a rectangle if the planar configuration of the film part 70d is an anisotropic configuration; and various modifications are possible. An example of the case where the planar configuration of the film part 70d is a flattened circle (e.g., an ellipse) will now be described.

FIG. 10A to FIG. 10D are schematic views illustrating the configuration and characteristics of another pressure sensor according to the first embodiment.

Figure 10A:
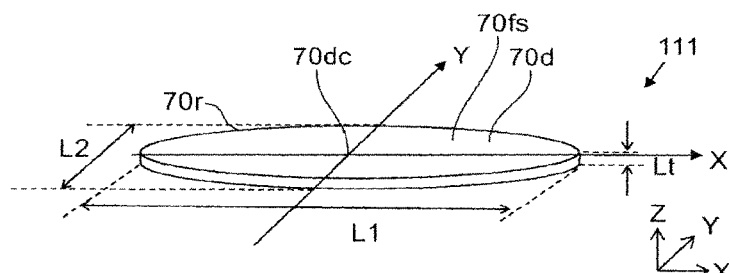
FIG. 10A to FIG. 10D are schematic views illustrating the configuration and characteristics of another pressure sensor according to the first embodiment.
Figure 10B:
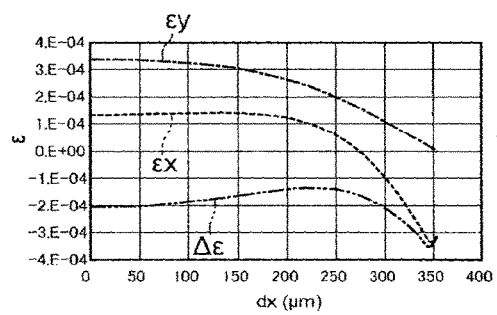
Figure 10C:
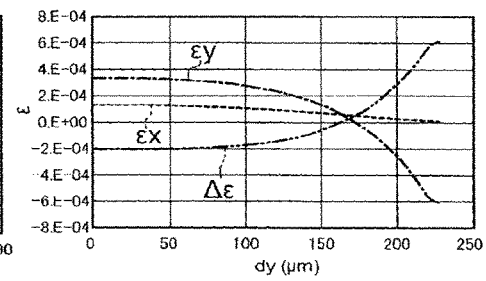
Figure 10D:
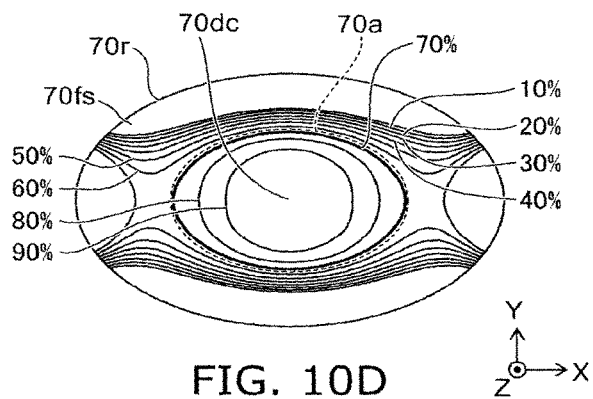

These drawings illustrate simulation results of characteristics of the pressure sensor 111 according to the embodiment. FIG. 10A is a schematic perspective view of the film part 70d. FIG. 10B and FIG. 10C illustrate the strain ε occurring in the film part 70d to which the pressure is applied. In FIG. 10B and FIG. 10C, the vertical axis is the strain ε. The horizontal axis of FIG. 10B is the position dx; and the horizontal axis of FIG. 10C is the position dy. FIG. 10D illustrates the distribution in the X-Y plane of the anisotropic strain Δε occurring in the film part 70d.

As shown in FIG. 10A, the planar configuration of the film part 70d (the configuration of the film surface 70fs) is a flattened circle (also including an ellipse). In other words, the configuration of the film part 70d projected onto the X-Y plane is a flattened circle having the first direction (in the example, the X-axis direction) as the major axis and the second direction (in the example, the Y-axis direction) as the minor axis. The configuration of the film surface 70fs is a flattened circle having the first direction as the major axis and the second direction as the minor axis.

In the example, the sensing element 50 (not-shown in the drawing) is disposed at the centroid 70dc vicinity of the film surface 70fs which is the ellipse. In the example, the length (the first length L1) of the major axis of the film part 70d is 704 μm; and the length (the second length L2) of the minor axis is 452 μm. The thickness Lt of the film part 70d is 2 μm. The conditions of the simulation are the same as the conditions described above.

In the pressure sensor 111 as well, the film part 70d has a convex configuration at the centroid 70dc vicinity of the film surface 70fs in the major-axis direction and the minor-axis direction. The outer edge 70r vicinity has a concave configuration due to the warp at the fixed end vicinity. Tensile strain occurs in the front surface of the film part 70d in the region of the warp in the convex configuration; and compressive strain occurs in the front surface of the film part 70d in the region of the warp in the concave configuration.

In such a case as well, it can be seen from FIG. 10B and FIG. 10C that the first strain εx and the second strain εy are tensile strains at the centroid 70dc where the warp is in the convex configuration. The anisotropic strain Δε is a compressive strain at the centroid 70dc. A compressive strain in the major-axis direction (the X-axis direction) exists at the centroid 70dc. In other words, a tensile anisotropic strain exists in the minor-axis direction (the Y-axis direction). In such a case as well, an anisotropic strain that is similar to the anisotropic strain obtained at the centroid 70dc exists in a wide area from the centroid 70dc to the outer edge 70r.

FIG. 10D shows the anisotropic strain occurrence region 70a. As described above, the anisotropic strain occurrence region 70a is the region where the anisotropic strain is 0.7 times the value (the absolute value) of the maximum anisotropic strain Δε obtained in the film part 70d (the anisotropic strain Δε0 at the centroid 70dc). As shown in FIG. 10D, an anisotropic strain Δε that is equivalent to that at the centroid 70dc can be obtained in a wide area (the anisotropic strain occurrence region 70a) at the centroid 70dc vicinity by using the film part 70d having the anisotropic configuration. The sensing element 50 (the multiple sensing elements 50) is disposed in the anisotropic strain occurrence region 70a. Thereby, a highly-sensitive pressure sensor is obtained.

The aspect ratio AR of the pressure sensor 111 illustrated in FIG. 10A is the same as the aspect ratio AR of the pressure sensor 110 illustrated in FIG. 5A. Comparing these pressure sensors, the surface area of the anisotropic strain occurrence region 70a is greater for the pressure sensor 111 (the elliptical film part 70d) than for the pressure sensor 110 (the rectangular film part 70d).

In the case where the planar configuration of the film part 70d is a flattened circle (including an ellipse) as shown in FIG. 10D, the configuration of the anisotropic strain occurrence region 70a also is a flattened circle (or substantially a circle). In such a case as well, the anisotropic strain occurrence region 70a is set to correspond to the central portion 70c of the embodiment.

In such a case as well, the centroid 70dc of the film surface 70fs substantially overlaps the centroid of the anisotropic strain occurrence region 70a. For example, the distance between the centroid 70dc of the film surface 70fs and the centroid of the anisotropic strain occurrence region 70a is, for example, not more than 1/10 of the second length L2.

In such a case as well, for example, the length of the anisotropic strain occurrence region 70a in the X-axis direction (corresponding to the third length L3 of the central portion 70c in the first direction) is not more than 0.3 times the first length L1. The length of the anisotropic strain occurrence region 70a in the Y-axis direction (corresponding to the fourth length L4 of the central portion 70c in the second direction) is not more than 0.3 times the second length L2.

Even in the case where the planar configuration of the film part 70d is a flattened circle, the pressure can be sensed with high sensitivity by disposing the sensing element 50 in such an anisotropic strain occurrence region 70a.

Figure 11A:
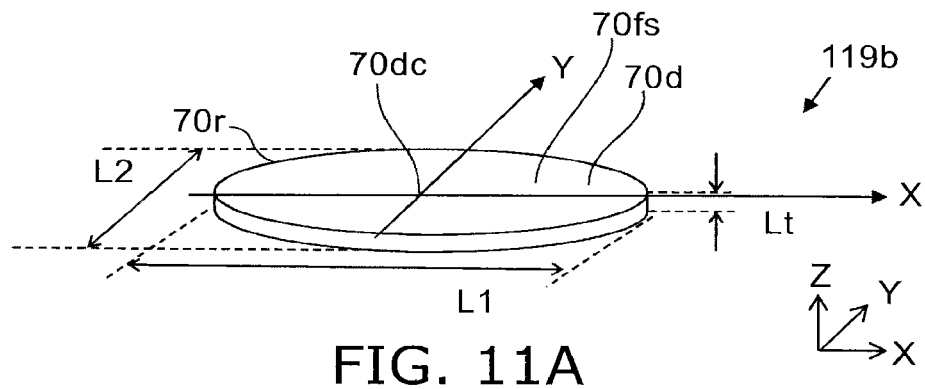
FIG. 11A to FIG. 11C are schematic views illustrating the configuration and characteristics of a pressure sensor of a reference example.
Figure 11B:
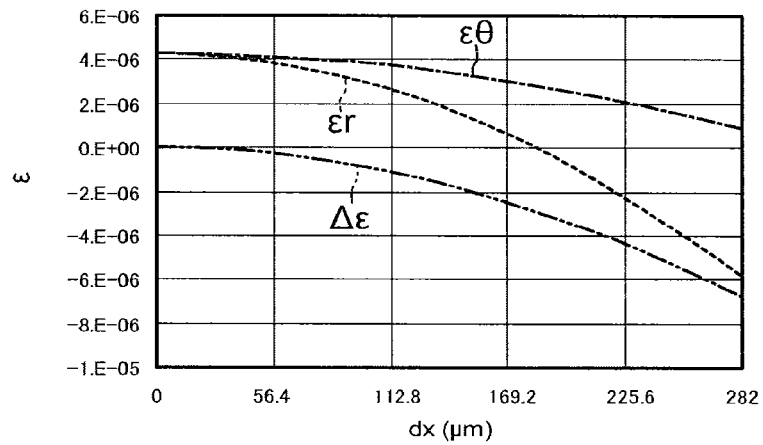
Figure 11C:
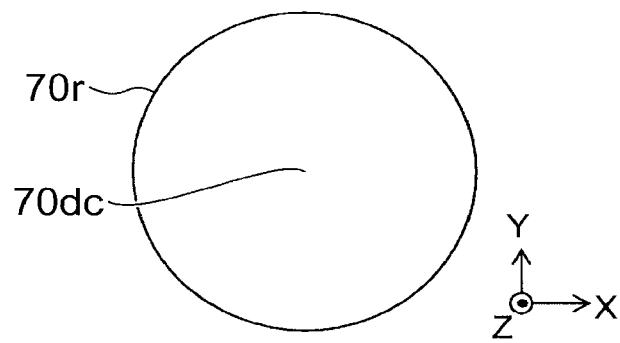

FIG. 11A to FIG. 11C are schematic views illustrating the configuration and characteristics of a pressure sensor of a reference example.

These drawings illustrate simulation results of characteristics of the pressure sensor 119b of the reference example. In the pressure sensor 119b, the planar configuration of the film part 70d is a circle; and the first length L1 and the second length L2 are 564 μm. Otherwise, the pressure sensor 119b of the reference example is similar to the pressure sensor 111. The conditions of the simulation also are similar to those of the pressure sensor 111. The surface area of the film part 70d of the pressure sensor 119b is the same as the surface area of the film part 70d of the pressure sensor 111. In the example, a strain εr in the radial direction and a strain εθ in the circumferential direction of the film part are determined. The anisotropic strain Δε is εr−εθ.

It can be seen from FIG. 11B that the anisotropic strain Δε at the centroid 70dc is zero. This is because the circular film part 70d is isotropic in the X-Y plane.

There are no contours illustrated in the contour diagram of FIG. 11C because the anisotropic strain Δε is not obtained at the centroid 70dc vicinity. In other words, the region at the centroid 70dc vicinity of the circle film surface 70fs where the anisotropic strain is obtained does not exist. Therefore, the change of the electrical resistance cannot be obtained even in the case where the sensing element 50 is disposed at the centroid 70dc vicinity.

Thus, the anisotropic strain can be applied to the sensing element 50 by disposing the sensing element 50 in a region (the central portion 70c) of the film surface 70fs including the centroid 70dc by using the film part 70d that is a flattened circle (e.g., an ellipse). Then, by providing multiple sensing elements 50 in this region, a similar change of electrical resistance (e.g., having the same polarity) due to the pressure occurs. The S/N ratio can be increased by, for example, connecting the multiple sensing elements 50 electrically in series. Further, a highly-sensitive pressure sensor is obtained by setting the bias voltage to be an appropriate value.

An example of the characteristics of the pressure sensor will now be described in more detail for the case where the planar configuration of the film part 70d is a flattened circle.

Figure 12:
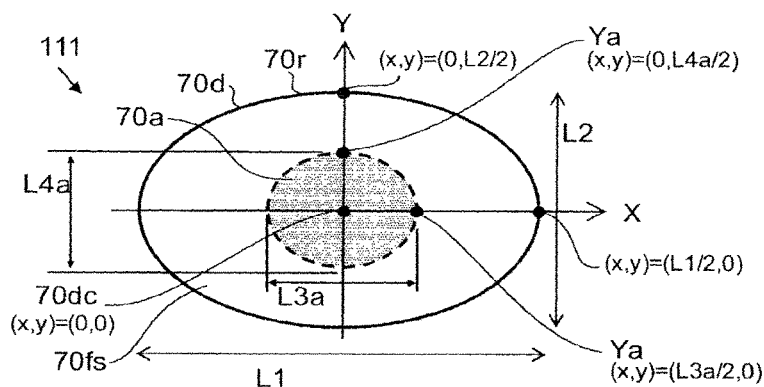
FIG. 12 is a schematic plan view illustrating the pressure sensor.

FIG. 12 is a schematic plan view illustrating the pressure sensor.

FIG. 12 illustrates the coordinate system of the film part 70d of the pressure sensor 111. In the example, the planar configuration of the film part 70d is an ellipse. In such a case as well, the coordinates of the outer edge of the film part 70d and the outer edge of the anisotropic strain occurrence region 70a can be defined similarly to those of the description regarding FIG. 7. The aspect ratio AR of the film part 70d also can be defined similarly.

An example of the characteristics of pressure sensors having seventh to twelfth configurations such as those recited below will now be described for the case where the planar configuration of the film part 70d is an ellipse.

In the seventh configuration, the first length L1 (the length of the major axis) is 2820 μm; the second length L2 (the length of the minor axis) is 112 μm; and the aspect ratio AR is 0.04.

In the eighth configuration, the first length L1 is 1784 μm; the second length L2 is 178 μm; and the aspect ratio AR is 0.1.

In the ninth configuration, the first length L1 is 1000 μm; the second length L2 is 250 μm; and the aspect ratio AR is 0.25.

In the tenth configuration, the first length L1 is 704 μm; the second length L2 is 452 μm; and the aspect ratio AR is 0.64. The tenth configuration corresponds to the configuration described in regard to FIG. 10A to FIG. 10D.

In the eleventh configuration, the first length L1 is 630 μm; the second length L2 is 504 μm; and the aspect ratio AR is 0.8.

In the twelfth configuration, the first length L1 is 564 μm; the second length L2 also is 564 μm; and the aspect ratio AR is 1. The twelfth configuration corresponds to the configuration described in regard to FIG. 11A to FIG. 11C.

The surface area of the film part 70d is constant at 250,000 μm$^2$ for each of these configurations.

Results of the simulation of the characteristics for the seventh to twelfth configurations having different aspect ratios AR using conditions (conditions such as the thickness of the film part 70d, material parameters, the mesh subdivision, etc.) similar to those recited above are as follows.

For the twelfth configuration for which the aspect ratio AR is 1, the anisotropic strain does not occur at the centroid 70dc. Conversely, for the seventh to eleventh configurations for which the aspect ratio AR is less than 1, the anisotropic strain is obtained at the centroid 70dc. A highly-sensitive pressure sensor is obtained by providing the sensing element 50 at the centroid 70dc vicinity of the film part 70d having the anisotropic configuration.

The aspect ratio AR dependence of the strain for the case where the planar configuration of the film part 70d is a flattened circle is similar to that of the case where the planar configuration is a rectangle. Thereby, from the aspect of increasing the value (the absolute value) of the anisotropic strain at the centroid 70dc, it is favorable for the aspect ratio AR of the film part 70d to be not less than 0.1 and not more than 0.8, and more favorable to be not less than 0.25 and not more than 0.64.

By examining the anisotropic strain occurrence region 70a for the film part 70d having an elliptical configuration of different aspect ratios AR, it was found that the characteristics are similar to the characteristics of the film part 70d having a rectangular configuration.

For example, the ratio (the surface area ratio Ra) of the surface area of the anisotropic strain occurrence region 70a to the surface area of the film part 70d increases as the aspect ratio decreases (the difference between the first length L1 and the second length L2 increases). Thereby, from the aspect of increasing the surface area of the anisotropic strain occurrence region 70a, it is favorable for the aspect ratio AR to be not more than 0.64, and more favorable to be not more than 0.25.

Even in the case where the planar configuration of the film part 70d is a flattened circle, in the case where the aspect ratio AR (L2/L1) is not less than 0.8 but less than 1, it is favorable for the settings to satisfy the seventh formula and the eighth formula recited above. Accordingly, even in the case where the planar configuration of the film part 70d is a flattened circle, in the case where the aspect ratio AR (L2/L1) is not less than 0.8 but less than 1, it is favorable for the third length L3 to be not less than 0.8 times and not more than 1.2 times L1×{−0.8×(L2/L1)+0.8}. Also, it is favorable for the fourth length L4 to be not less than 0.8 times and not more than 1.2 times L2×{−2.5×(L2/L1)+2.5}.

Even in the case where the planar configuration of the film part 70d is a flattened circle, it is favorable for the settings to satisfy the ninth formula and the tenth formula recited above. In other words, in the case where the aspect ratio AR (L2/L1) is less than 0.8, it is favorable for the third length to be not less than 0.8 times and not more than 1.2 times L1×{−0.8×(L2/L1)+0.8}. It is favorable for the fourth length L4 to be not less than 0.8 times and not more than 1.2 times L2×{0.375×(L2/L1)+0.2}.

By satisfying such conditions, an anisotropic strain having a larger absolute value is obtained; and a highly-sensitive pressure sensor is obtained more reliably.

Figures 13A, 13B:
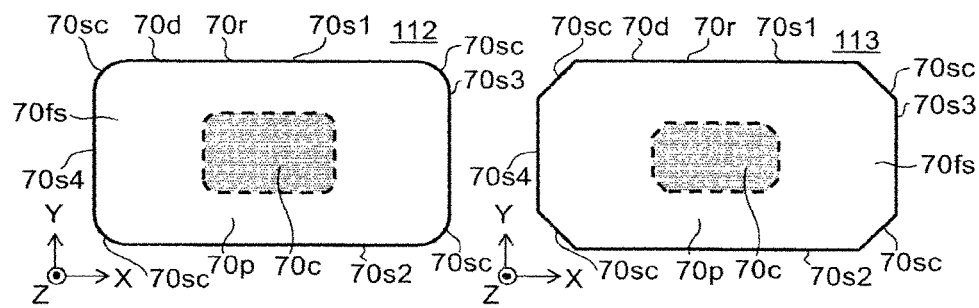
FIG. 13A to FIG. 13C are schematic plan views illustrating other pressure sensors according to the first embodiment.
Figure 13C:
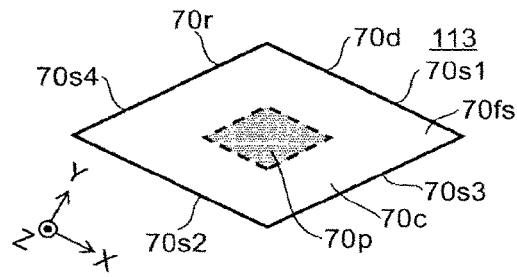

FIG. 13A to FIG. 13C are schematic plan views illustrating other pressure sensors according to the first embodiment.

These drawings illustrate the planar configuration of the film part 70d.

In a pressure sensor 112 according to the embodiment as shown in FIG. 13A, the planar configuration of the film part 70d is substantially rectangular (rectangle); and corner portions 70sc of the film part 70d have curved configurations. In other words, the film part 70d has the first to fourth sides 70s1 to 70s4; and the sides are connected by the corner portions 70sc having the curved configurations.

In a pressure sensor 113 according to the embodiment as shown in FIG. 13B, the film part 70d has the first to fourth sides 70s1 to 70s4; and the sides are connected by the corner portions 70sc having linear configurations.

Thus, in the embodiment, two sides may be connected by the corner portions 70sc. This state also is included in the state in which two sides are connected.

In a pressure sensor 114 according to the embodiment as shown in FIG. 13C, the planar configuration of the film part 70d is a parallelogram, e.g., in the example, a diamond. In other words, the film part 70d includes the first to fourth sides 70s1 to 70s4. The first side 70s1 and the second side 70s2 are along the first direction (e.g., the X-axis direction); and the third side 70s3 and the fourth side 70s4 are along a third direction that is tilted with respect to the first direction. The third direction is non-parallel to the first direction and non-orthogonal to the first direction. In the example as well, the sides may be connected by the corner portions 70sc having curved configurations or linear configurations.

In the pressure sensors 112 to 114 as well, the planar configuration of the film part 70d is an anisotropic configuration. In other words, for example, the length of the film part 70d along the first axis 70x passing through the centroid 70dc of the film surface 70fs is longer than the length of the film part 70d along the second axis 70y intersecting (e.g., orthogonal to) the first axis 70x to pass through the centroid 70dc of the film surface 70fs. The sensing element 50 is disposed in such a central portion 70c of the film part 70d. According to the pressure sensors 112 to 114 as well, highly-sensitive pressure sensors are obtained.

In the embodiment, the configuration of the anisotropic strain occurrence region 70a corresponds to the planar configuration of the film part 70d. In the case where the planar configuration of the film part 70d is a rectangle, the anisotropic strain occurrence region 70a is a rectangular area at the vicinity of the centroid 70dc of the film surface 70fs. In the case where the planar configuration of the film part 70d is a flattened circle, the anisotropic strain occurrence region 70a is a flattened circular area at the vicinity of the centroid 70dc of the film surface 70fs. In the case where the planar configuration of the film part 70d is a diamond, the anisotropic strain occurrence region 70a is a diamond-like area at the vicinity of the centroid 70dc of the film surface 70fs. The anisotropic strain occurrence regions 70a are used as the central portion 70c of the film part 70d.

In the embodiment, multiple sensing elements may be provided in the sensing unit 50u.

Figure 14A:
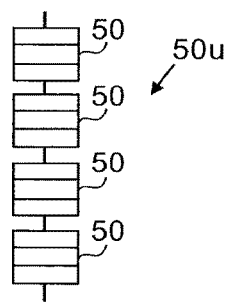
FIG. 14A to FIG. 14C are schematic views illustrating pressure sensors according to the first embodiment.
Figure 14B:
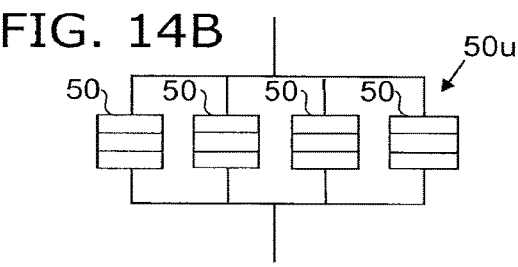
Figure 14C:
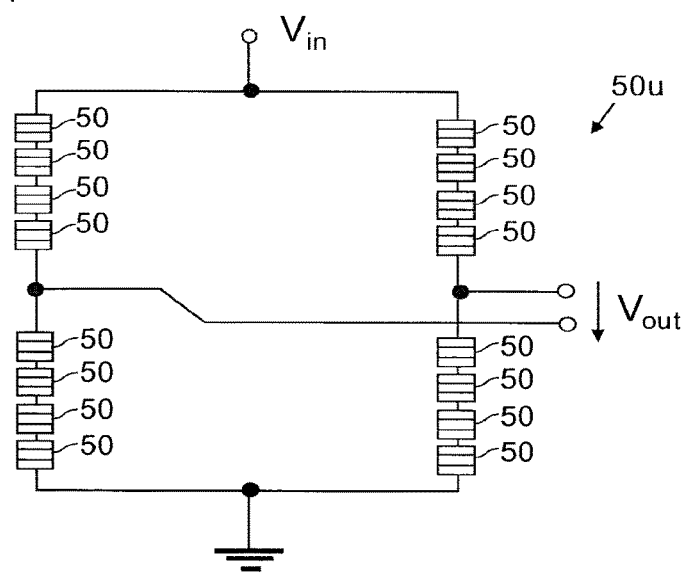

FIG. 14A to FIG. 14C are schematic views illustrating pressure sensors according to the first embodiment.

These drawings show examples of the connection state of the multiple sensing elements.

As shown in FIG. 14A, the multiple sensing elements 50 are connected in series. In the case where N sensing elements of the multiple sensing elements 50 are connected in series, the electrical signal that is obtained is N times that of the case where the number of the sensing elements 50 is 1. On the other hand, the thermal noise and the Schottky noise increase by a factor of $N^{1/2}$. In other words, the SN ratio (signal-noise ratio (SNR)) increases by a factor of $N^{1/2}$. By increasing the number N of the sensing elements 50 connected in series, the SN ratio can be increased without causing the size of the film part 70d to become large.

By using the film part 70d having the anisotropic configuration in the embodiment, the change (e.g., the polarity) of the electrical resistance due to the pressure is similar between the multiple sensing elements 50 disposed together at the centroid 70dc vicinity of the film part 70d. Therefore, it is possible to add the signals of the multiple sensing elements 50.

The bias voltage applied to one sensing element 50 is, for example, not less than 50 millivolts (my) and not more than 150 mV. In the case where N sensing elements 50 are connected in series, the bias voltage is not less than 50 mV×N and not more than 150 mV×N. For example, in the case where the number N of the sensing elements 50 connected in series is 25, the bias voltage is not less than 1 V and not more than 3.75 V.

In the case where the value of the bias voltage is 1 V or more, the design of the electronic circuit that processes the electrical signal obtained from the sensing elements 50 is easy and practically favorable. In the embodiment, the sensing element 50 can be multiply disposed to obtain electrical signals having the same polarity when the pressure is applied. Therefore, the SN ratio can be increased as recited above by connecting the sensing elements 50 in series.

In the electronic circuit that processes the electrical signals obtained from the sensing elements 50, it is undesirable for the bias voltage (the voltage across terminals) to exceed 10 V. In the embodiment, the bias voltage and the number N of the sensing elements 50 connected in series are set to be in appropriate voltage ranges.

For example, in the case where the multiple sensing elements 50 are connected electrically in series, it is favorable for the voltage to be not less than 1 V and not more than 10 V. For example, the voltage that is applied between the terminals of the multiple sensing elements 50 connected electrically in series (between the terminal of one end and the terminal of the other end) is not less than 1 V and not more than 10 V.

To generate the voltage, it is favorable for the number N of the sensing elements 50 connected in series to be not less than 20 and not more than 200 in the case where the bias voltage applied to one sensing element 50 is 50 mv. In the case where the bias voltage applied to the one sensing element 50 is 150 mV, it is favorable for the number N of the sensing elements 50 connected in series to be not less than 7 and not more than 66.

As shown in FIG. 14B, at least a portion of the multiple sensing elements 50 may be connected electrically in parallel.

As shown in FIG. 14C, the multiple sensing elements 50 may be connected such that the multiple sensing elements 50 form a Wheatstone bridge circuit. Thereby, for example, temperature compensation of the sensing characteristics can be performed.

Figure 15A:
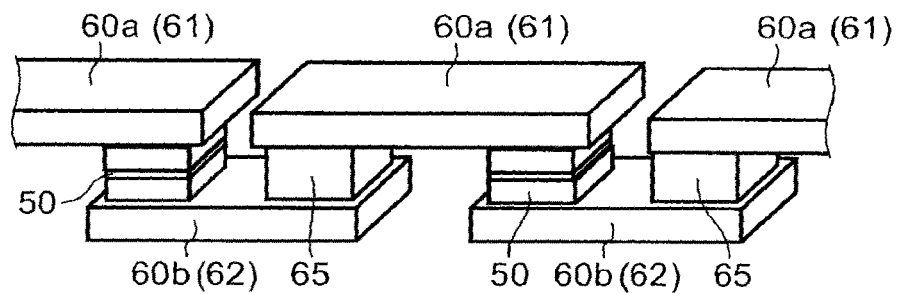
FIG. 15A to FIG. 15C are schematic perspective views illustrating pressure sensors according to the first embodiment.
Figure 15B:
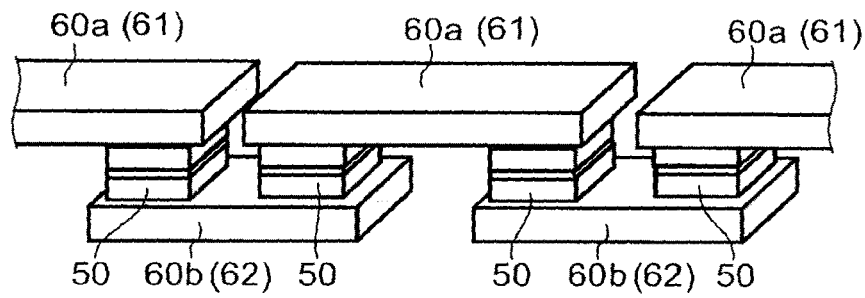
Figure 15C:
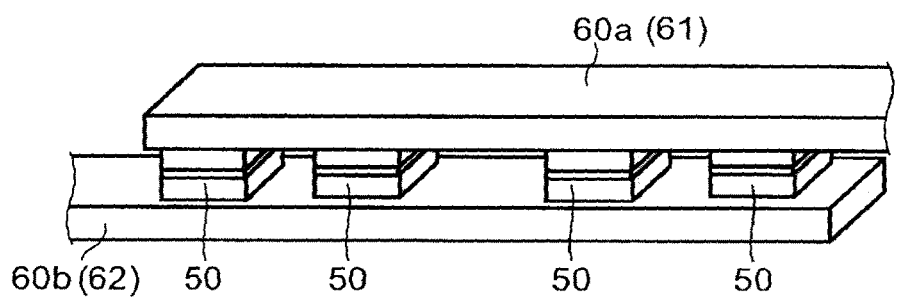

FIG. 15A to FIG. 15C are schematic perspective views illustrating pressure sensors according to the first embodiment.

These drawings show examples of connections of the multiple sensing elements 50.

As shown in FIG. 15A, the sensing elements 50 and via contacts 65 are provided between a lower electrode 60b (e.g., the second interconnect 62) and an upper electrode 60a (e.g., the first interconnect 61) in the case where the multiple sensing elements 50 are connected electrically in series. Thereby, the conduction direction is in one direction. The current conducted through the multiple sensing elements 50 is downward or upward. In this connection, the signal-noise characteristics of the multiple sensing elements 50 can be similar to each other.

As shown in FIG. 15B, the sensing elements 50 are disposed between the lower electrode 60b and the upper electrode 60a without the via contacts 65 being provided. In the example, the direction of the current conducted through the sensing element 50 is reversed between two mutually-adjacent sensing elements 50. For this connection, the density of the disposition of the multiple sensing elements 50 is high.

As shown in FIG. 15C, the multiple sensing elements 50 are provided between one lower electrode 60b and one upper electrode 60a. The multiple sensing elements 50 are connected in parallel.

Second Embodiment

FIG. 16A to FIG. 16D are schematic views illustrating a pressure sensor according to a second embodiment.

Figure 16A:
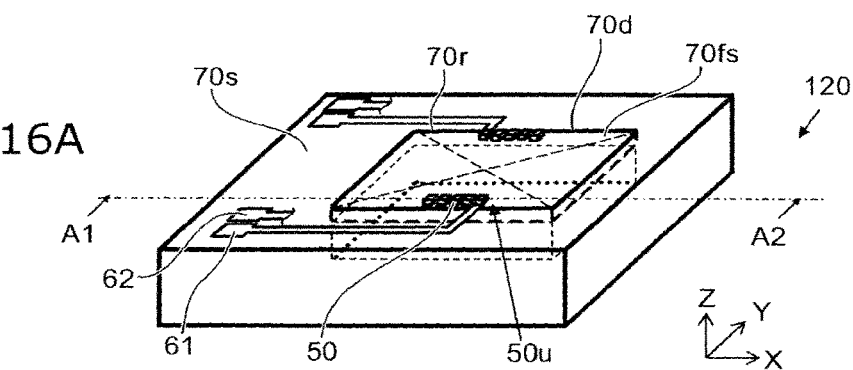
FIG. 16A to FIG. 16D are schematic views illustrating a pressure sensor according to a second embodiment.
Figure 16B:
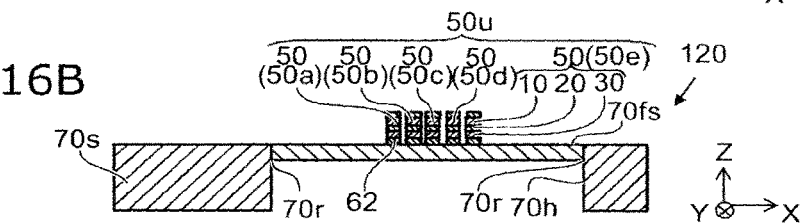
Figure 16C:
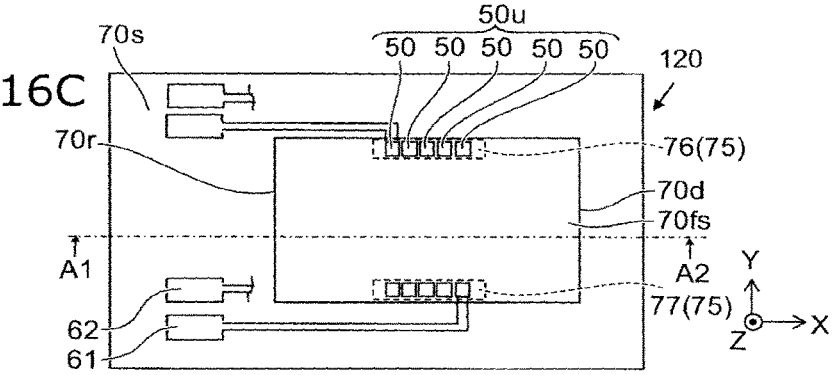
Figure 16D:
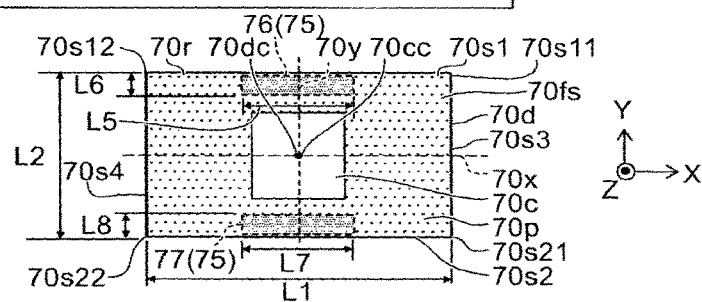

FIG. 16A is a schematic perspective view. FIG. 16B is a cross-sectional view along line A1-A2 of FIG. 16A and FIG. 16C. FIG. 16C is a schematic plan view. FIG. 16D is a schematic plan view of the film part included in the pressure sensor.

As shown in FIG. 16A to FIG. 16C, the pressure sensor 120 according to the embodiment also includes the film part 70d and the sensing unit 50u. The support unit 70s is provided in the example. The film part 70d is supported by the support unit 70s and is flexible. The sensing unit 50u includes the multiple sensing elements 50 (e.g., the first to fifth sensing elements 50a to 50e, etc.). The multiple sensing elements 50 are provided on the film part 70d. In the example as well, each of the multiple sensing elements 50 includes the first magnetic layer 10, the second magnetic layer 20 provided between the first magnetic layer 10 and the film part 70d, and the spacer layer 30 provided between the first magnetic layer 10 and the second magnetic layer 20. The spacer layer 30 may include, for example, a magnetic material. The disposition of the sensing unit 50u of the pressure sensor 120 is different from that of the pressure sensor 110.

The positions of at least two of the multiple sensing elements 50 along the first direction (e.g., the X-axis direction) are different from each other. In the example, the multiple sensing elements 50 are arranged along the outer edge 70r of the film part 70d. Otherwise, the pressure sensor 120 is similar to the pressure sensor 110; and a description is therefore omitted.

As shown in FIG. 16C, an element disposition region 75 (e.g., a first element disposition region 76 and a second element disposition region 77) is provided in the film part 70d of the pressure sensor 120. The element disposition region 75 extends along the outer edge of the film part 70d. The multiple sensing elements 50 are provided on the element disposition region 75.

The element disposition region 75 is provided on the peripheral portion 70p of the film part 70d. In other words, the film part 70d includes the central portion 70c and the peripheral portion 70p. The peripheral portion 70p is provided around the central portion 70c. The multiple sensing elements 50 are provided on the element disposition region 75 of the peripheral portion 70p of the film part 70d.

In other words, instead of being arranged in a radial configuration from the central portion 70c toward the peripheral portion 70p, the multiple sensing elements 50 may be arranged along the outer edge 70r of the peripheral portion 70p.

In the example, the planar configuration of the film part 70d is an anisotropic configuration. In other words, the first length L1 of the film part 70d in the first direction (e.g., the X-axis direction) in the film surface 70fs is longer than the second length L2 of the film part 70d in the second direction (e.g., the Y-axis direction which is a direction perpendicular to the first direction in the film surface 70fs).

In such a case, the positions of at least two of the multiple sensing elements 50 provided inside the element disposition region 75 along the first direction (e.g., the X-axis direction) are different from each other. In the example, the multiple sensing elements 50 are arranged along the first direction (in the example, the X-axis direction) inside the element disposition region 75.

In the embodiment, for example, two most proximal sensing elements 50 of the multiple sensing elements are arranged along the outer edge 70r.

In the example, the planar configuration of the film part 70d is substantially rectangular.

In other words, as shown in FIG. 16D, the film part 70d has the first to fourth sides 70s1 to 70s4. The first side 70s1 is provided along the first direction (e.g., the X-axis direction). The second side 70s2 is provided along the first direction to be separated from the first side 70s1. The third side 70s3 is provided along the second direction (e.g., the Y-axis direction) to be connected to the one end 70s11 of the first side 70s1 and the one end 70s21 of the second side 70s2. The fourth side 70s4 is provided along the second direction to be separated from the third side 70s3 and connected to the other end 70s12 of the first side 70s1 and the other end 70s22 of the second side 70s2. As described below, the sides may be connected to each other by corner portions having linear configurations or curved configurations.

Thus, in the case where the planar configuration of the film part 70d is substantially rectangular, the element disposition region 75 is provided to extend along a side of the rectangle. In the example, the peripheral portion 70p of the film part 70d includes the first element disposition region 76 provided along the first side 70s1. The multiple sensing elements 50 are provided on the first element disposition region 76; and the positions along the first direction (e.g., the X-axis direction) of the multiple sensing elements 50 (at least two of the multiple sensing elements 50) are different from each other. In the example, the multiple sensing elements 50 that are provided on the first element disposition region 76 are arranged along the first side 70s1.

In the example, the peripheral portion 70p of the film part 70d includes the second element disposition region 77 provided along the second side 70s2. The multiple sensing elements 50 are further provided on the second element disposition region 77. The positions along the first direction (e.g., the X-axis direction) of the multiple sensing elements 50 (at least two of the multiple sensing elements 50) provided on the second element disposition region 77 are different from each other. In the example, the multiple sensing elements 50 that are provided on the second element disposition region 77 are arranged along the second side 70s2.

Thus, in the pressure sensor 120 according to the embodiment, the positions along the first direction (e.g., the X-axis direction) of at least two of the multiple sensing elements 50 are different from each other and are arranged, for example, along the first direction. Thereby, in the multiple sensing elements 50, a similar resistance change occurs for the pressure that is applied. According to the embodiment, a highly-sensitive pressure sensor can be provided.

In the pressure sensor 120, for example, the multiple sensing elements 50 are disposed in at least one selected from the first element disposition region 76 and the second element disposition region 77. In other words, the first element disposition region 76 may be provided; and the second element disposition region 77 may not be provided. Or, the second element disposition region 77 may be provided; and the first element disposition region 76 may not be provided.

For example, any of the configurations described in regard to FIG. 14A to FIG. 14C and FIG. 15A to FIG. 15C are applicable to the connections of the multiple sensing elements 50 in the embodiment.

In the pressure sensor 120, the planar configuration of the film part 70d is an anisotropic configuration. Also, the multiple sensing elements 50 are provided together on the element disposition region 75 of the film part 70d. The element disposition region 75 is a region at the minor-axis end portion vicinity of the film part 70d.

As described in regard to the first embodiment, in the case where the planar configuration of the film part 70d is an anisotropic configuration, strains that are different between the major-axis direction and the minor-axis direction of the film part 70d occur in the surface of the film part 70d when the film part 70d deflects due to the pressure being applied from one surface of the film part 70d. The strain occurring in the minor-axis direction is greater than the strain occurring in the major-axis direction. The region on the film part 70d where the anisotropic strain occurs is wider for the film part 70d having the anisotropic configuration than for the film part 70d having the isotropic configuration. This tendency also is confirmed at the end portion vicinity of the film part 70d on the minor axis side.

The anisotropic strain having the large absolute value occurs in a wider region at the end portion on the minor axis side of the film part 70d having the anisotropic configuration than at the end portion of the film part 70d having the isotropic configuration. Therefore, the number of the sensing elements 50 for which a similar change of electrical resistance (e.g., having the same polarity) occurs due to the pressure can be increased. Thereby, a highly-sensitive pressure sensor can be provided.

The SN ratio can be increased by connecting the multiple sensing elements 50 in series. In the embodiment as well, the sensing elements 50 can be disposed to obtain electrical signals having the same polarity when the pressure is applied. Thereby, the SN ratio can be increased. In the embodiment, for example, the bias voltage and the number N of the sensing elements 50 connected in series are set to be in appropriate voltage ranges. For example, it is favorable for the voltage when the multiple sensing elements 50 are connected electrically in series to be not less than 1 V and not more than 10 V. For example, in the case where the bias voltage applied to one sensing element 50 is 50 mV, it is favorable for the number N of the sensing elements 50 connected in series to be not less than 20 and not more than 200. In the case where the bias voltage applied to the one sensing element 50 is 150 mV, it is favorable for the number N of the sensing elements 50 connected in series to be not less than 7 and not more than 66.

At least a portion of the multiple sensing elements 50 may be connected electrically in parallel. The multiple sensing elements 50 may be connected such that the multiple sensing elements 50 form a Wheatstone bridge circuit. Thereby, for example, temperature compensation of the sensing characteristics can be performed.

In the example, the planar configuration of the element disposition region 75 (the planar configurations of the first element disposition region 76 and the second element disposition region 77) is substantially rectangular.

For example, the length (a fifth length L5) of the first element disposition region 76 in the first direction (e.g., the X-axis direction) is not more than 0.5 times the first length L1. The width (a sixth length L6) of the first element disposition region 76 in the second direction (e.g., the Y-axis direction) is not more than 0.1 times the second length L2.

The X-axis direction center of the first element disposition region 76 is substantially aligned with the X-axis direction center of the film part 70d. For example, the distance in the first direction between the center of the first element disposition region 76 in the first direction (e.g., the X-axis direction) and the first-direction center of the film part 70d is not more than 1/10 of the second length L2.

Similarly, for example, the length (a seventh length L7) of the second element disposition region 77 in the first direction (e.g., the X-axis direction) is not more than 0.5 times the first length L1. The width (an eighth length L8) of the second element disposition region 77 in the second direction (e.g., the Y-axis direction) is not more than 0.1 times the second length L2.

The X-axis direction center of the second element disposition region 77 is substantially aligned with the X-axis direction center of the film part 70d. For example, the distance in the first direction between the center of the second element disposition region 77 in the first direction (e.g., the X-axis direction) and the first-direction center of the film part 70d is not more than 1/10 of the second length L2.

An example of the characteristics in the case where the planar configuration of the film part 70d is a rectangle and the multiple sensing elements 50 are disposed together at the end portion vicinity of the film part 70d on the minor axis side will now be described.

Figure 17A:
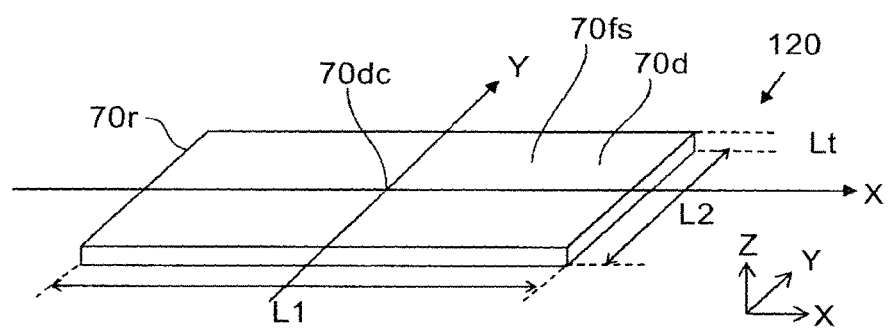
FIG. 17A and FIG. 17B are schematic views illustrating the configuration and characteristics of the pressure sensor according to the second embodiment.
Figure 17B:
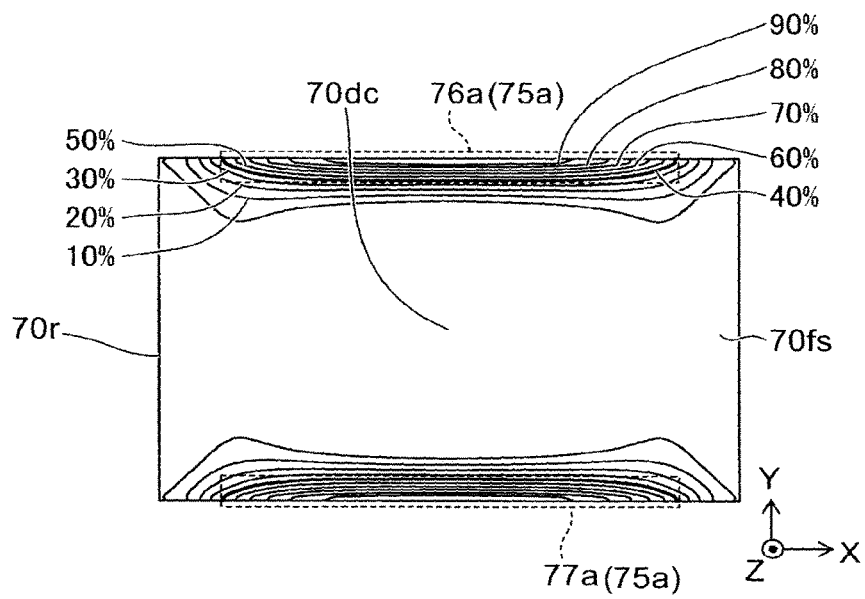

FIG. 17A and FIG. 17B are schematic views illustrating the configuration and characteristics of the pressure sensor according to the second embodiment.

These drawings illustrate simulation results of characteristics of the pressure sensor 120. FIG. 17A is a schematic perspective view of the film part 70d. FIG. 17B illustrates the distribution in the X-Y plane of the anisotropic strain $\Delta\varepsilon$ occurring in the film part 70d.

In the example as shown in FIG. 17A, the planar configuration of the film part 70d is a rectangle. In the example, the length (the first length L1) of the film part 70d in the major-axis direction is 625 µm; the length (the second length L2) in the minor-axis direction is 400 µm; and the thickness Lt is 2 µm.

The analysis of the strain occurring in the front surface of the film part 70d is performed for such a film part 70d. The conditions of the finite element method of the analysis are similar to those described in regard to the first embodiment. The dependence of the displacement of the film part 70d on the distance from the centroid 70dc is the same as the results (FIG. 5D and FIG. 5E) described in regard to the first embodiment. An end portion anisotropic strain occurrence region 75a is the area where the anisotropic strain is not less than 0.4 times (i.e., 40% of) the maximum value of the anisotropic strain (the absolute value) obtained at the end portion of the film part 70d on the minor axis side. Because two end portions exist, the end portion anisotropic strain occurrence region 75a includes a first end portion anisotropic strain occurrence region 76a and a second end portion anisotropic strain occurrence region 77a.

FIG. 17B is a contour diagram illustrating the first end portion anisotropic strain occurrence region 76a and the second end portion anisotropic strain occurrence region 77a.

It can be seen from FIG. 17B that the first end portion anisotropic strain occurrence region 76a and the second end portion anisotropic strain occurrence region 77a occur at the vicinity of the two minor-axis direction end portions by using the film part 70d having the anisotropic configuration. The surface areas of these regions are large. The surface area of the end portion anisotropic strain occurrence region 75a (the sum of the surface area of the first end portion anisotropic strain occurrence region 76a and the surface area of the second end portion anisotropic strain occurrence region 77a) is about 8500 µm².

Thus, an anisotropic strain that is equivalent to that of the minor-axis direction end portion can be obtained in a wide area at the end portion vicinity. In the embodiment, the multiple sensing elements 50 are disposed in the area where the equivalent anisotropic strain is obtained. In other words, for example, the first end portion anisotropic strain occurrence region 76a is set to be the first element disposition region 76; and the second end portion anisotropic strain occurrence region 77a is set to be the second element disposition region 77. A highly-sensitive pressure sensor is obtained by disposing the multiple sensing elements 50 in such regions.

It can be seen from FIG. 17B that in the case where the film part 70d has a rectangle configuration, the configuration of the end portion anisotropic strain occurrence region 75a (the configurations of the first end portion anisotropic strain occurrence region 76a and the second end portion anisotropic strain occurrence region 77a) also is substantially rectangular.

The length (corresponding to the fifth length L5) of the first end portion anisotropic strain occurrence region 76a in the X-axis direction is not more than 0.5 times the first length L1. The width (corresponding to the sixth length L6) of the first end portion anisotropic strain occurrence region 76a in the Y-axis direction is not more than 0.1 times the second length L2. The first end portion anisotropic strain occurrence region 76a has substantially line symmetry around an axis passing through the centroid 70dc of the film surface 70fs parallel to the second direction. For example, the distance in the X-axis direction between the X-axis direction center of the first end portion anisotropic strain occurrence region 76a and the X-axis direction center of the film part 70d is not more than 1/10 of the second length L2.

Similarly, the length (corresponding to the seventh length L7) of the second end portion anisotropic strain occurrence region 77a in the X-axis direction is not more than 0.5 times the first length L1. The width (corresponding to the eighth length L8) of the second end portion anisotropic strain occurrence region 77a in the Y-axis direction is not more than 0.1 times the second length L2. For example, the distance in the X-axis direction between the X-axis direction center of the second end portion anisotropic strain occurrence region 77a and the X-axis direction center of the film part 70d is not more than 1/10 of the second length L2.

The first element disposition region 76 is set to correspond to such a first end portion anisotropic strain occurrence region 76a; and the second element disposition region 77 is set to correspond to such a second end portion anisotropic strain occurrence region 77a. In the embodiment, the multiple sensing elements 50 are disposed along the outer edge 70r of the film part 70d on such regions. For example, the centroids of the multiple sensing elements 50 overlap these regions when the multiple sensing elements 50 are projected onto the X-Y plane. Thereby, a highly-sensitive pressure sensor is obtained.

In the embodiment, the multiple sensing elements 50 are provided in at least one selected from the first end portion anisotropic strain occurrence region 76a and the second end portion anisotropic strain occurrence region 77a.

Figure 18A:
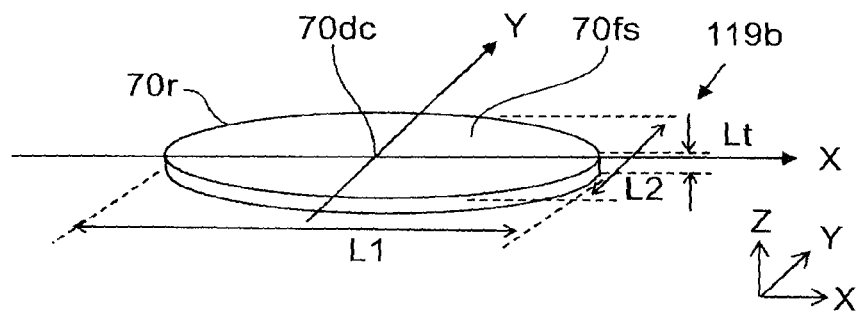
FIG. 18A and FIG. 18B are schematic views illustrating the configuration and characteristics of a pressure sensor of a reference example.
Figure 18B:
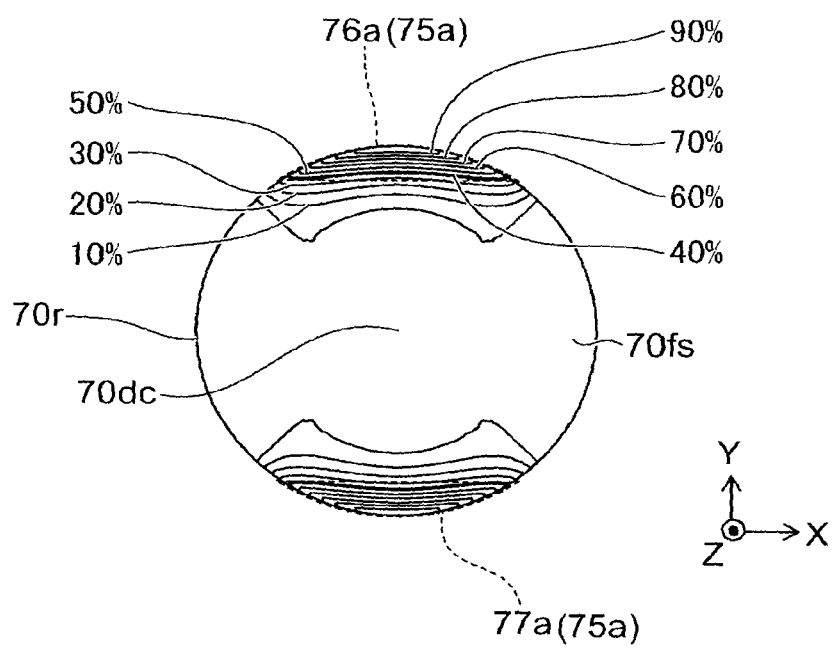

FIG. 18A and FIG. 18B are schematic views illustrating the configuration and characteristics of a pressure sensor of a reference example.

These drawings illustrate simulation results of characteristics of the pressure sensor 119b of the reference example. FIG. 18A is a schematic perspective view of the film part 70d. FIG. 18B illustrates the distribution in the X-Y plane of the anisotropic strain Δε occurring in the film part 70d.

In the pressure sensor 119b of the reference example as shown in FIG. 18A, the planar configuration of the film part 70d is a circle. The diameter (the first length L1 and the second length L2) of the planar configuration of the film part 70d is 564 μm; and the thickness Lt of the film part 70d is 2 μm. The strain of the pressure sensor 119b is as described in regard to FIG. 11B. The end portion anisotropic strain occurrence region 75a (the area where the anisotropic strain is not less than 0.4 times (i.e., 40% of) the maximum value of the absolute value of the anisotropic strain obtained at the end portion of the film part 70d on the minor axis side) is determined from the analysis results of the strain.

FIG. 18B is a contour diagram of the end portion anisotropic strain occurrence region 75a. In the reference example, the surface areas of the first end portion anisotropic strain occurrence region 76a and the second end portion anisotropic strain occurrence region 77a are small. The surface area of the end portion anisotropic strain occurrence region 75a (the sum of the surface area of the first end portion anisotropic strain occurrence region 76a and the surface area of the second end portion anisotropic strain occurrence region 77a) is about 5000 μm².

The surface area of the film part 70d is the same for the pressure sensor 120 and the pressure sensor 119b. The ratio of the surface area of the end portion anisotropic strain occurrence region 75a to the surface area of the film part 70d is higher for the pressure sensor 120 than for the pressure sensor 119b.

Thus, by using the film part 70d having the anisotropic configuration (e.g., the rectangle), the region (the end portion anisotropic strain occurrence region 75a) where the large anisotropic strain is obtained can be larger than in the case where the isotropic circular film part 70d is used. In the embodiment, the multiple sensing elements 50 are disposed in this region.

In the pressure sensor 120, the multiple sensing elements 50 are disposed together along the minor-axis direction outer edge 70r of the rectangular film part 70d having the anisotropic configuration. Thereby, a similar anisotropic strain (e.g., having the same polarity) is applied to the multiple sensing elements 50. In the embodiment, the multiple sensing elements 50 that have similar change of electrical resistance (e.g., having the same polarity) due to the pressure can be disposed in this region. The S/N ratio can be increased by connecting the sensing elements, for example, electrically in series. Further, a highly-sensitive pressure sensor can be provided by setting the bias voltage to be an appropriate value.

An example of the characteristics will now be described for different aspect ratios of the film part 70d in the case where the planar configuration of the film part 70d is a rectangle and the multiple sensing elements 50 are disposed together at the minor-axis direction end portion vicinity of the film part. The first end portion anisotropic strain occurrence region 76a of the end portion anisotropic strain occurrence region 75a will now be described.

Figure 19:
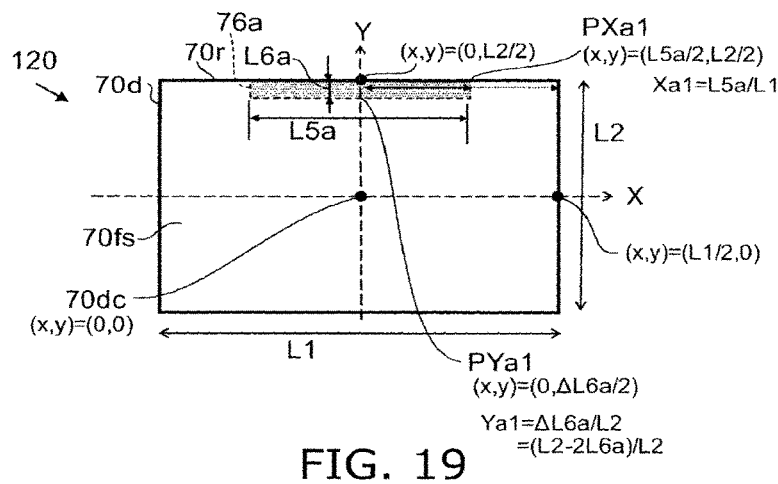
FIG. 19 is a schematic plan view illustrating a pressure sensor.

FIG. 19 is a schematic plan view illustrating a pressure sensor.

FIG. 19 illustrates the coordinate system of the film part 70d of the pressure sensor 120. The coordinates (x, y) of the centroid of the film surface 70fs are (0, 0). The coordinates of one point of the outer edge 70r of the film part 70d in the X-axis direction are (L1/2, 0). The coordinates of one point of the outer edge 70r of the film part 70d in the Y-axis direction are (0, L2/2).

The length of the first end portion anisotropic strain occurrence region 76a in the first direction (the length in the X-axis direction) is a length L5a; and the length of the first end portion anisotropic strain occurrence region 76a in the second direction (the length in the Y-axis direction) is a length L6a. The difference between the second length L2 and the length L6a is ΔL6a (i.e., ΔL6a=L2−2×L6a). The coordinates of one point PXa1 of the outer edge of the first end portion anisotropic strain occurrence region 76a in the X-axis direction are (L5a/2, L2/2). The coordinates of one point PYa1 in the Y-axis direction of the outer edge on the centroid 70dc side of the first end portion anisotropic strain occurrence region 76a are (0, ΔL6a/2).

An example of the characteristics will now be described for different aspect ratios AR of the film part 70d for the case where the planar configuration of the film part 70d is such a rectangle.

FIG. 20A to FIG. 20D are graphs illustrating the characteristics of the pressure sensors.

These drawings show the characteristics of the pressure sensors having the first to sixth configurations described above. These drawings also show the characteristics of a pressure sensor of a thirteenth configuration.

In the thirteenth configuration, the planar configuration of the film part 70d is a circle. Namely, the first length L1 is 564 μm; the second length L2 is 564 μm; and the aspect ratio AR is 1. The thirteenth configuration corresponds to the configuration described in regard to FIG. 18A and FIG. 18B.

Figure 20A:
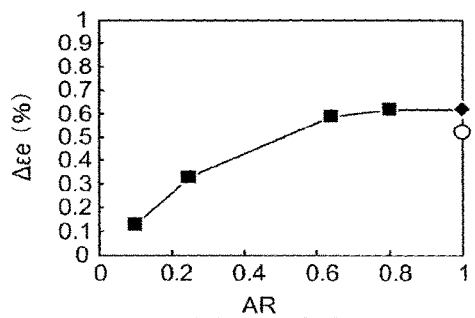
FIG. 20A to FIG. 20D are graphs illustrating the characteristics of the pressure sensors.
Figure 20B:
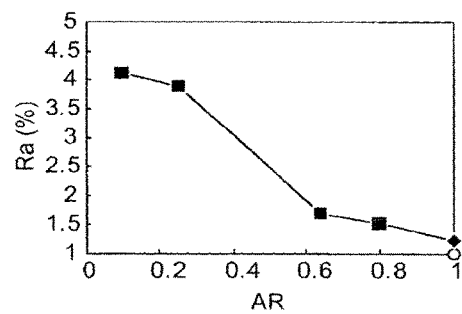

In the first to fifth configurations, the planar configuration of the film part 70d is a rectangle and has an anisotropic configuration. In the sixth configuration, the planar configuration of the film part 70d is a square. In the thirteenth configuration, the planar configuration of the film part 70d is a circle. In FIG. 20A to FIG. 20D, the values for the first to sixth configurations are illustrated by the solid symbols. In FIG. 20A and FIG. 20B, the values for the thirteenth configuration are illustrated by the unfilled round symbols.

Analysis of the strain occurring in the front surface of the film part 70d is performed by finite element analysis for these configurations. The conditions of the finite element method are the same as the conditions described in regard to FIG. 5A to FIG. 5F.

In FIG. 20A, the vertical axis is an anisotropic strain Δεe (the absolute value of the anisotropic strain) at the end portion of the film part 70d. The horizontal axis is the aspect ratio AR of the planar configuration of the film part 70d. For the thirteenth configuration (the unfilled round symbols), the absolute value of the anisotropic strain Δεe at the end portion is small. Conversely, for the first to sixth configurations (the solid symbols), the absolute value of the anisotropic strain Δεe at the end portion is large. Thus, compared to the case where the planar configuration of the film part 70d is a circle, an anisotropic strain Δεe having a large absolute value is obtained for the first to sixth configurations having planar configurations that are rectangular or square.

From FIG. 20A, from the aspect of increasing the absolute value of the anisotropic strain Δεe at the end portion of the film part 70d, it is favorable for the aspect ratio AR of the film part 70d to be not less than 0.25 but less than 1.0, and more favorable to be not less than 0.64 but less than 1.0.

The first end portion anisotropic strain occurrence region 76a (the area where the anisotropic strain is not less than 0.4 times (i.e., 40% of) the maximum value of the anisotropic strain obtained at the end portion of the film part 70d on the minor axis side) was analyzed for the first to sixth configurations. As a result, it was found that the planar configuration of the first end portion anisotropic strain occurrence region 76a is a rectangle.

In FIG. 20B, the vertical axis is the ratio (the surface area ratio Ra) of the surface area of the first end portion anisotropic strain occurrence region 76a to the surface area of the film part 70d. The horizontal axis is the aspect ratio AR. It can be seen from FIG. 20B that the surface area ratio Ra is higher (greater) for the first to sixth configurations than for the thirteenth configuration. The surface area ratio Ra increases as the aspect ratio AR decreases (as the difference between the first length L1 and the second length L2 increases). From the aspect of widening the region on the film part 70d where the anisotropic strain is obtained, it is favorable for the aspect ratio AR to be not more than 0.8, and more favorable to be not more than 0.25.

The position of the outer edge of the first end portion anisotropic strain occurrence region 76a (the coordinates referring to FIG. 19) will now be described.

Figure 20C:
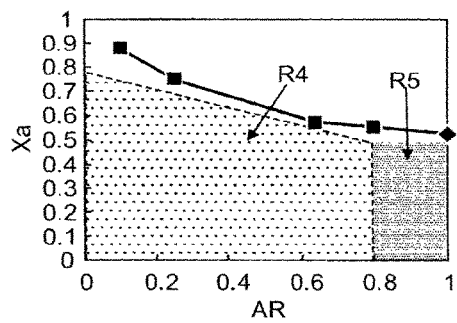

The vertical axis of FIG. 20C is the normalized coordinate (a distance Xa1) of the point PXa1 in the X-axis direction on the outer edge of the first end portion anisotropic strain occurrence region 76a. The distance Xa1 corresponds to (L5a)/(L1).

Figure 20D:
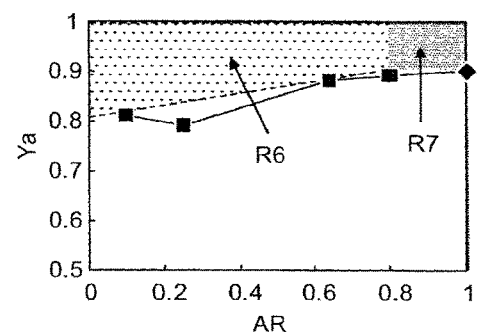

The vertical axis of FIG. 20D is the normalized coordinate (a distance Ya1) of the point PYa1 in the Y-axis direction on the centroid 70dc side on the outer edge of the first end portion anisotropic strain occurrence region 76a. The distance Ya1 corresponds to (ΔL6a)/(L2).

In these drawings, the horizontal axis is the aspect ratio AR. FIG. 20C and FIG. 20D show the results for the first to sixth configurations.

It can be seen from these drawings that the distance Xa1 and the distance Ya1 are greater than zero for the first to sixth configurations. In other words, the first end portion anisotropic strain occurrence region 76a is obtained for these configurations.

It can be seen from these drawings that in the case where the aspect ratio AR is not less than 0.8 but less than 1, it is favorable that $|Xa1| \le (L1/2) \times 0.5$, and $|Ya1| \ge (L2/2) \times 0.9$.

On the other hand, in the case where the aspect ratio AR is less than 0.8, it is favorable that $|Xa1| \le (L1/2) \times \{-0.375 \times (L2/L1) + 0.8\}$, and $|Ya1| \ge (L2/2) \times \{0.125 \times (L2/L1) + 0.8\}$.

In FIG. 20C, a fourth hatching region R4 that is the light hatching and a fifth hatching region R5 that is the dark hatching correspond to the conditions of the first end portion anisotropic strain occurrence region 76a. In FIG. 20D, a sixth hatching region R6 that is the light hatching and a seventh hatching region R7 that is the dark hatching correspond to the conditions of the first end portion anisotropic strain occurrence region 76a.

The fourth hatching region R4 is represented by the eleventh formula recited below, i.e., the twelfth formula recited below.

$$Xa1 \le -0.375 AR + 0.8 \tag{11}$$

$$L5a \le L1 \times \{-0.375(L2/L1) + 0.8\} \tag{12}$$

The fifth hatching region R5 is represented by the thirteenth formula recited below, i.e., the fourteenth formula recited below.

$$Xa1 \le 0.5 \tag{13}$$

$$L5a \le 0.5 L1 \tag{14}$$

The sixth hatching region R6 is represented by the fifteenth formula recited below, i.e., the sixteenth formula recited below.

$$Ya1 \ge 0.125 AR + 0.8 \tag{15}$$

$$L6a \le (L2/2)\{1 - 0.125(L2/L1) + 0.8\} \tag{16}$$

The seventh hatching region R7 is represented by the seventeenth formula recited below, i.e., the eighteenth formula recited below.

$$Ya1 \geq 0.9 \quad (17)$$

$$L6a \leq 0.05L2 \quad (18)$$

In other words, in the case where the aspect ratio AR is less than 0.8, the conditions of the eleventh formula, the twelfth formula, the fifteenth formula, and the sixteenth formula are favorable.

On the other hand, in the case where the aspect ratio AR is not less than 0.8 but less than 1, the conditions of the thirteenth formula, the fourteenth formula, the seventeenth formula, and the eighteenth formula are favorable.

In other words, in the case where the aspect ratio AR is less than 0.8, it is favorable for the length (the length L5a) of the first element disposition region 76 in the first direction to be not more than $L1 \times \{-0.375 \times (L2/L1) + 0.8\}$. It is favorable for the width (the length L6a) of the first element disposition region 76 in the second direction to be not more than $(L2/2) \times \{1 - 0.125 \times (L2/L1) + 0.8\}$. It is favorable for the first-direction center of the first element disposition region 76 to substantially overlap the first-direction center of the film part 70d and for the distance in the first direction between the first-direction center of the first element disposition region 76 and the first-direction center of the film part 70d to be, for example, 1/10 of the second length L2.

On the other hand, in the case where the aspect ratio AR is not less than 0.8 but less than 1, it is favorable for the width (the length L5a) of the first element disposition region 76 in the first direction to be not more than 0.5 times the second length L2. It is favorable for the width (the length L6a) of the first element disposition region 76 in the second direction to be not more than 0.05 times the second length L2.

The characteristics of the second element disposition region are similar to the characteristics of the first element disposition region 76 recited above.

An example of the characteristics in the case where the planar configuration of the film part 70d is an ellipse and the multiple sensing elements 50 are disposed together at the minor-axis direction end portion vicinity of the film part 70d will now be described.

Figure 21A:
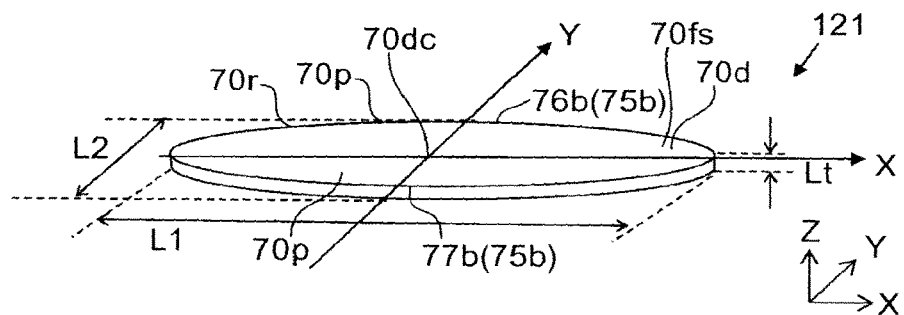
FIG. 21A and FIG. 21B are schematic views illustrating the configuration and characteristics of another pressure sensor according to the second embodiment.
Figure 21B:
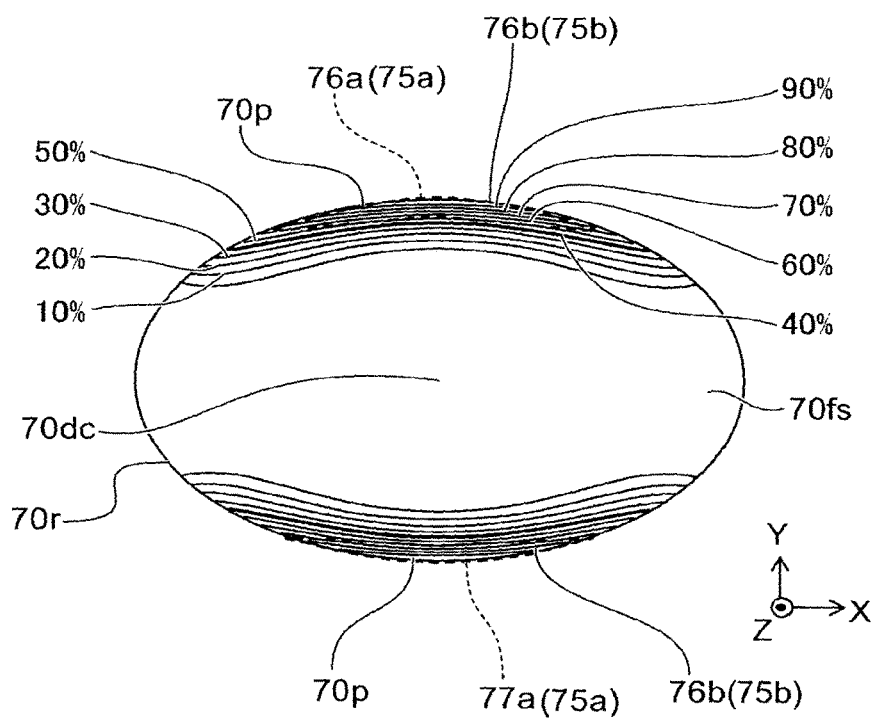

FIG. 21A and FIG. 21B are schematic views illustrating the configuration and characteristics of another pressure sensor according to the second embodiment.

These drawings illustrate simulation results of characteristics of the pressure sensor 121 according to the embodiment. FIG. 21A is a schematic perspective view of the film part 70d. FIG. 21B illustrates the distribution in the X-Y plane of the anisotropic strain Δε occurring in the film part 70d.

As shown in FIG. 21A, the planar configuration of the film part 70d is a flattened circle (also including an ellipse). The sensing element 50 (not-shown in the drawing) is disposed at the minor axis (the second direction) end portion of the film part 70d. In the example, the length (the first length L1) of the major axis of the film part 70d is 704 μm; and the length (the second length L2) in the minor axis is 452 μm. The thickness Lt of the film part 70d is 2 μm. The conditions of the simulation are the same as the conditions described above.

The dependence of the strain of the front surface of the film part 70d on the distance from the centroid is as illustrated in FIG. 10B and FIG. 10C described above.

FIG. 21B is a contour diagram illustrating the end portion anisotropic strain occurrence region 75a (the first end portion anisotropic strain occurrence region 76a and the second end portion anisotropic strain occurrence region 77a). As described above, an anisotropic strain that is not less than 0.4 times (i.e., 40% of) the anisotropic strain Δεe (corresponding to the maximum value) occurring at the end portion of the film part 70d is obtained in the end portion anisotropic strain occurrence region 75a. As shown in FIG. 21B, by using the film part 70d having the anisotropic configuration, an anisotropic strain that is equivalent to that of the end portion can be obtained in a wide area at the minor-axis direction end portion vicinity. The surface area of the end portion anisotropic strain occurrence region 75a (the sum of the surface area of the first end portion anisotropic strain occurrence region 76a and the surface area of the second end portion anisotropic strain occurrence region 77a) is about 6600 μm².

On the other hand, as described above, in the pressure sensor 119b in which the planar configuration of the film part 70d is a circle, the surface area of the end portion anisotropic strain occurrence region 75a is about 5000 μm². The surface area of the film part 70d is the same between in the pressure sensor 121 and the pressure sensor 119b. The ratio of the surface area of the end portion anisotropic strain occurrence region 75a to the surface area of the film part 70d is higher for the pressure sensor 121 than for the pressure sensor 119b.

Thus, in the embodiment, the configuration of the film surface 70fs may be a flattened circle (including an ellipse). For example, the configuration of the film part 70d projected onto a plane (e.g., the X-Y plane) parallel to the film surface 70fs of the film part 70d may be a flattened circle (including an ellipse). In the flattened circle, the first direction (e.g., the X-axis direction) is taken to be the major axis; and the second direction (e.g., the Y-axis direction) is taken to be the minor axis.

As illustrated in FIG. 21A and FIG. 21B, the peripheral portion 70p of the film part 70d has an arc 75b (a major-axis arc) along the major axis. The arc 75b along the major axis includes, for example, a first arc 76b and a second arc 77b. The first element disposition region 76 is provided along the first arc 76b. The second element disposition region 77 is provided along the second arc 77b.

At least two of the multiple sensing elements 50 are arranged along the major-axis arc (the first arc 76b) in the first element disposition region 76. At least two other elements of the multiple sensing elements 50 are arranged along the major-axis arc (the second arc 77b) in the second element disposition region 77.

According to such a pressure sensor 120, a highly-sensitive pressure sensor can be provided.

In the example, the multiple sensing elements 50 may be provided in at least one selected from the first end portion anisotropic strain occurrence region 76a and the second end portion anisotropic strain occurrence region 77a.

An example of the characteristics of the case where the planar configuration of the film part 70d is an ellipse and the multiple sensing elements 50 are disposed together at the minor-axis direction end portion vicinity of the film part 70d will now be described.

A tendency that is similar to that of the rectangular film part 70d is obtained when analyzing the aspect ratio AR dependence of the anisotropic strain for the seventh to eleventh configurations described above. From the aspect of increasing the absolute value of the anisotropic strain, it is favorable for the aspect ratio AR to be not less than 0.25 but less than 1.0, and more favorable to be not less than 0.64 but less than 1.0.

In the seventh to eleventh configurations, the ratio (the surface area ratio) of the surface area of the end portion anisotropic strain occurrence region 75a to the surface area of the film part 70d is larger than that of the thirteenth configuration. The surface area ratio increases as the aspect ratio AR decreases (the difference between the first length L1 and the second length L2 increases). From the aspect of widening the region on the film part 70d where the anisotropic strain is obtained, it is favorable for the aspect ratio AR to be not more than 0.8, and more favorable to be not more than 0.25.

Figure 22:
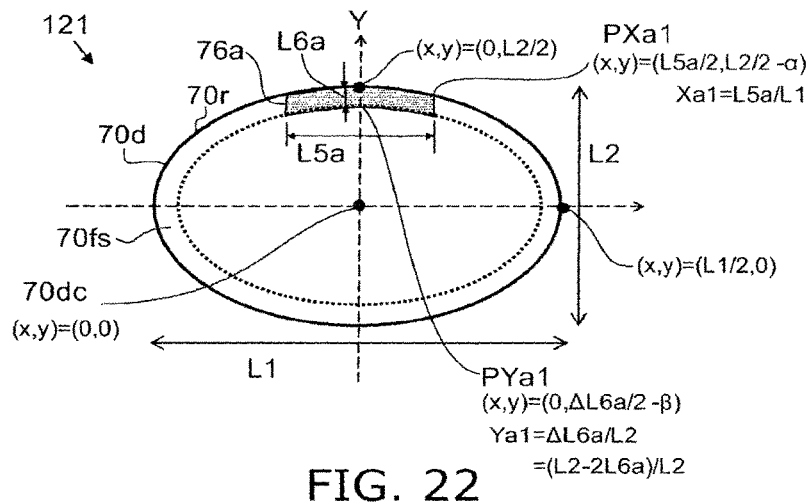
FIG. 22 is a schematic view illustrating another pressure sensor according to the second embodiment

FIG. 22 is a schematic view illustrating another pressure sensor according to the second embodiment.

FIG. 22 illustrates the coordinate system of the film part 70d of the pressure sensor 121. In the case where the planar configuration of the film part 70d is an ellipse, the coordinates of the first end portion anisotropic strain occurrence region 76a may be substantially similar to those of the pressure sensor 120 illustrated in FIG. 19.

Using such coordinates, the characteristics were examined for the coordinates of the first end portion anisotropic strain occurrence region 76a in the case where the planar configuration of the film part 70d is an ellipse. As a result, it was found that the characteristics in the case where the film part 70d is an ellipse are similar to the characteristics in the case where the planar configuration is a rectangle.

Accordingly, in such a case as well, in the case where the aspect ratio AR is less than 0.8, it is favorable for the length (the length L5a) of the first element disposition region 76 in the first direction to be not more than L1×{−0.375×(L2/L1)+0.8}. It is favorable for the width (the length L6a) of the first element disposition region 76 in the second direction to be not more than (L2/2)×{1−0.125×(L2/L1)+0.8}. It is favorable for the first-direction center of the first element disposition region 76 to substantially overlap the first-direction center of the film part 70d and for the distance in the first direction between the first-direction center of the first element disposition region 76 and the first-direction center of the film part 70d to be, for example, not more than 1/10 of the second length L2.

On the other hand, in such a case as well, in the case where the aspect ratio AR is not less than 0.8 but less than 1, it is favorable for the length (the length L5a) of the first element disposition region 76 in the first direction to be not more than 0.5 times the second length L2. It is favorable for the width (the length L6a) of the first element disposition region 76 in the second direction to be not more than 0.05 times the second length L2.

The characteristics of the second element disposition region are similar to the characteristics of the first element disposition region 76.

Figures 23A, 23B:
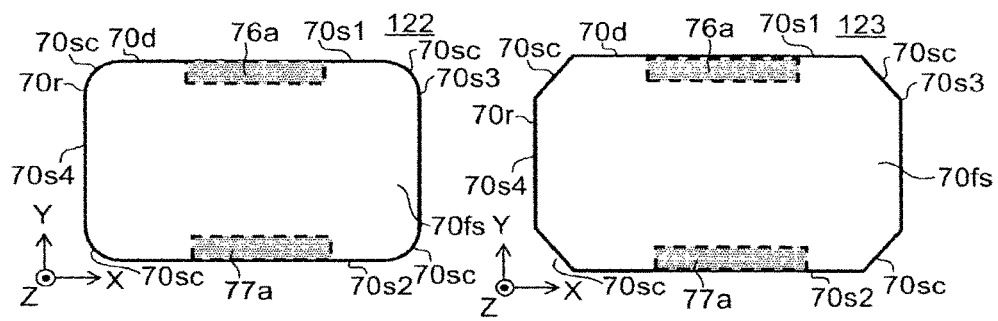
FIG. 23A and FIG. 23B are schematic plan views illustrating other pressure sensors according to the second embodiment.

FIG. 23A and FIG. 23B are schematic plan views illustrating other pressure sensors according to the second embodiment.

These drawings illustrate the planar configuration of the film part 70d.

In a pressure sensor 122 according to the embodiment as shown in FIG. 23A, the corner portions 70sc have curved configurations. In a pressure sensor 123 according to the embodiment as shown in FIG. 23B, the corner portions 70sc have linear configurations. According to the pressure sensors 122 and 123 as well, a highly-sensitive pressure sensor is obtained.

FIG. 24A to FIG. 24F are schematic plan views illustrating other pressure sensors according to the second embodiment.

These drawings illustrate the disposition of the multiple sensing elements 50 in the element disposition region 75. In the example, the first element disposition region 76 is illustrated as the element disposition region 75. The disposition of the multiple sensing elements 50 in the second element disposition region 77 may be, for example, similar to the disposition of the multiple sensing elements 50 in the first element disposition region 76.

In a pressure sensor 120a as shown in FIG. 24A, the multiple sensing elements 50 are arranged along the X-axis direction (the direction along the long side of the film part 70d). In the example, the planar configuration of the sensing element 50 (the configuration of the sensing element 50 when the sensing element 50 is projected onto the X-Y plane) is a rectangle. The configuration of the sensing element 50 is, for example, a square.

As shown in FIG. 24B, in a pressure sensor 120b as well, the multiple sensing elements 50 are arranged along the X-axis direction (the direction along the long side of the film part 70d). In the example, the planar configuration of the sensing element 50 is a circle. The planar configuration of the sensing element 50 may be a flattened circle. The planar configuration of the sensing element 50 may be a rectangle.

In a pressure sensor 120c as shown in FIG. 24C, the multiple sensing elements 50 are arranged in multiple columns. In each of the columns, the multiple sensing elements 50 are arranged along the X-axis direction (the direction along the long side of the film part 70d). The disposition of the multiple sensing elements 50 is, for example, a staggered disposition. In the example, the planar configuration of the sensing element 50 is a circle. The planar configuration of the sensing element 50 may be a flattened circle. The planar configuration of the sensing element 50 may be a rectangle.

In pressure sensors 120d and 120e as shown in FIG. 24D and FIG. 24E, the distance between the outer edge 70r of the film part 70d and each of the multiple sensing elements 50 is different between the multiple sensing elements 50. The multiple sensing elements 50 are arranged along an arc. In these examples, the planar configuration of the sensing element 50 is a circle. The planar configuration of the sensing element 50 may be a flattened circle. The planar configuration of the sensing element 50 may be a rectangle.

In the pressure sensor 120d illustrated in FIG. 24D, the distance between the outer edge 70r and the sensing elements 50 disposed in the region of the X-axis direction central portion of the first element disposition region 76 is longer than the distance between the outer edge 70r and the sensing elements 50 disposed in the region of the X-axis direction end portion of the first element disposition region 76.

In the pressure sensor 120e illustrated in FIG. 24E, the distance between the outer edge 70r and the sensing elements 50 disposed in the region of the X-axis direction central portion of the first element disposition region 76 is shorter than the distance between the outer edge 70r and the sensing elements 50 disposed in the region of the X-axis direction end portion of the first element disposition region 76.

In a pressure sensor 120f as shown in FIG. 24F, the multiple sensing elements 50 are disposed arbitrarily inside the element disposition region 75. In the example, the planar configuration of the sensing element 50 is a circle. The planar configuration of the sensing element 50 may be a flattened circle. The planar configuration of the sensing element 50 may be a rectangle.

Thus, in the embodiment, the multiple sensing elements 50 are disposed such that the positions along the first direction (the X-axis direction) of at least two of the multiple sensing elements 50 provided in the element disposition region 75 (at least one selected from the first element disposition region 76 and the second element disposition region 77) are different from each other.

Figure 25A:
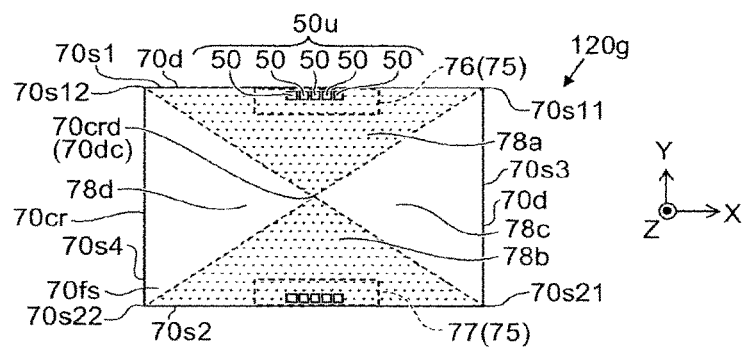
FIG. 25A and FIG. 25B are schematic plan views illustrating other pressure sensors according to the second embodiment.
Figure 25B:
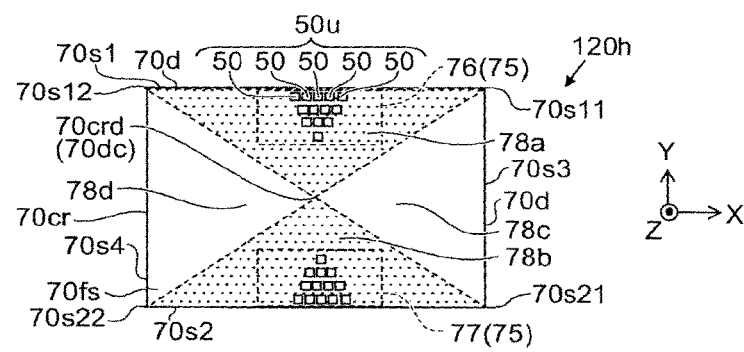

FIG. 25A and FIG. 25B are schematic plan views illustrating other pressure sensors according to the second embodiment.

These drawings illustrate the element disposition region 75 (the first element disposition region 76 and the second element disposition region 77) and the disposition of the multiple sensing elements 50.

The first element disposition region 76 and the second element disposition region 77 are provided in pressure sensors 120g and 120h according to the embodiment as shown in FIG. 25A and FIG. 25B. The multiple sensing elements 50 are provided in each of these regions.

In the pressure sensor 120g as shown in FIG. 25A, the multiple sensing elements 50 are along the X-axis direction (the direction along the length L1 of the film part 70d) in each of these regions.

In the pressure sensor 120h as shown in FIG. 25B, the multiple sensing elements 50 are disposed in multiple columns along the X-axis direction (the direction along the length L1 of the film part 70d) in each of these regions. The number of the sensing elements 50 included in the multiple columns is different between the multiple columns. The multiple sensing elements 50 are disposed in a triangular configuration in each of these regions. One side of the triangle is provided along the X-axis direction.

As shown in FIG. 25A and FIG. 25B, a circumscribing rectangle 70cr is formable when the film part 70d is projected onto a plane (e.g., the X-Y plane) parallel to the film surface 70fs. The circumscribing rectangle 70cr circumscribes the configuration of the film surface 70fs. The configuration of the film surface 70fs has, for example, the configuration of the outer edge 70r of the film part 70d projected onto a plane parallel to the film surface 70fs. In the example, the planar configuration of the film part 70d is an anisotropic configuration and is a rectangle. The circumscribing rectangle 70cr also is a rectangle.

The circumscribing rectangle 70cr has the first side 70s1, the second side 70s2, the third side 70s3, and the fourth side 70s4. The second side 70s2 is separated from the first side 70s1. The third side 70s3 is connected to the one end 70s11 of the first side 70s1 and the one end 70s21 of the second side 70s2. The fourth side 70s4 is separated from the third side 70s3 and connected to the other end 70s12 of the first side 70s1 and the other end 70s22 of the second side 70s2.

In the example, the first length of the film part 70d in the first direction (the X-axis direction) in the film surface 70fs of the film part 70d is longer than the second length of the film part 70d in the second direction (the Y-axis direction) perpendicular to the first direction in the film surface 70fs. Therefore, the circumscribing rectangle 70cr is a rectangle. The first side 70s1 and the second side 70s2 extend in the first direction (the X-axis direction). The third side 70s3 and the fourth side 70s4 extend in the second direction (the Y-axis direction). The length of the first side 70s1 is the same as the length of the second side 70s2. The length of the third side 70s3 is shorter than the length of the first side 70s1 and shorter than the length of the second side 70s2. The length of the fourth side 70s4 is shorter than the length of the first side 70s1 and shorter than the length of the second side 70s2.

The circumscribing rectangle 70cr has a centroid 70crd. For example, the centroid 70crd overlaps the centroid 70dc of the film surface 70fs.

The circumscribing rectangle 70cr includes a first region 78a, a second region 78b, a third region 78c, and a fourth region 78d.

The first region 78a is the region enclosed by the first side 70s1, the line segment connecting the centroid 70crd to the one end 70s11 of the first side 70s1, and the line segment connecting the centroid 70crd to the other end 70s12 of the first side 70s1.

The second region 78b is the region enclosed by the second side 70s2, the line segment connecting the centroid 70crd to the one end 70s21 of the second side 70s2, and the line segment connecting the centroid 70crd to the other end 70s22 of the second side 70s2.

The third region 78c is the region enclosed by the third side 70s3, the line segment connecting the centroid 70crd to the one end 70s11 of the first side 70s1, and the line segment connecting the centroid 70crd to the one end 70s21 of the second side 70s2.

The fourth region 78d is the region enclosed by the fourth side 70s4, the line segment connecting the centroid 70crd to the other end 70s12 of the first side 70s1, and the line segment connecting the centroid 70crd to the other end 70s22 of the second side 70s2.

As shown in FIG. 25A and FIG. 25B, the multiple sensing elements 50 are provided on the portion of the film surface 70fs overlapping the first region 78a. The positions along the first direction (the X-axis direction) of at least two of the multiple sensing elements 50 provided in the region of the film surface 70fs overlapping the first region 78a are different from each other.

Also, in the example, the multiple sensing elements 50 are further provided on the portion of the film surface 70fs overlapping the second region 78b. In other words, multiple sensing elements 50 that are different from the at least two recited above provided on the portion of the film surface 70fs overlapping the first region 78a are disposed on the portion of the film surface 70fs overlapping the second region 78b. The positions along the first direction (the X-axis direction) of the at least two other sensing elements 50 disposed on the portion overlapping the second region 78b are different from each other.

As in the pressure sensor 121 described above, the circumscribing rectangle 70cr can be defined even in the case where the planar configuration of the film part 70d (the configuration of the film surface 70fs) is a flattened circle. As in the pressure sensors 122 and 123, the circumscribing rectangle 70cr can be defined even in the case where the corner portions 70sc having curved configurations or linear configurations are provided in the planar configuration of the film part 70d (the configuration of the film surface 70fs). Also, the first to fourth regions 78a to 78d can be defined. In the pressure sensors 121 to 123 as well, the multiple sensing elements 50 are provided on the portion of the film surface 70fs overlapping the first region 78a. The positions along the first direction (the X-axis direction) of the at least two of the multiple sensing elements 50 provided in the region of the film surface 70fs overlapping the first region 78a are different from each other. Further, the multiple sensing elements 50 are provided on the portion of the film surface 70fs overlapping the second region 78b. The positions along the first direction (the X-axis direction) of the at least two other sensing elements 50 disposed on the portion overlapping the second region 78b are different from each other.

Figure 26:
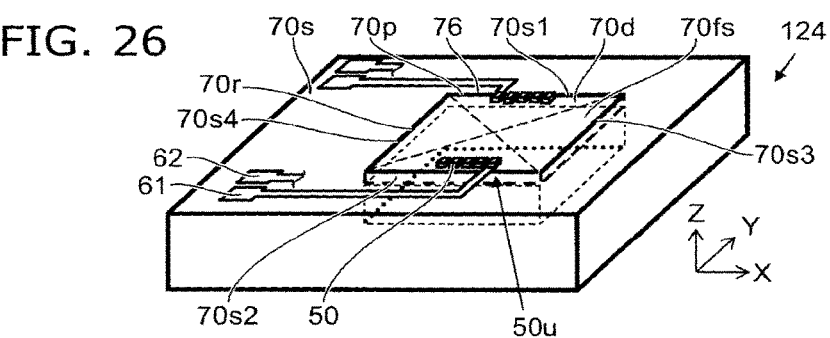
FIG. 26 is a schematic perspective view illustrating another pressure sensor according to the second embodiment.

FIG. 26 is a schematic perspective view illustrating another pressure sensor according to the second embodiment.

In the pressure sensor 124 according to the embodiment as shown in FIG. 26, the planar configuration of the film part 70d is a square. Otherwise, the pressure sensor 124 is similar to the pressure sensor 120.

In the example, the film part 70d includes the first side 70s1 provided along the first direction (e.g., the X-axis direction), the second side 70s2 provided along the first direction to be separated from the first side 70s1, the third side 70s3 provided along the second direction (e.g., the Y-axis direction) to be connected to the one end 70s11 of the first side 70s1 and the one end 70s21 of the second side 70s2, and the fourth side 70s4 provided along the second direction to be separated from the third side 70s3 and connected to the other end 70s12 of the first side 70s1 and the other end 70s22 of the second side 70s2.

The peripheral portion 70p of the film part 70d includes the first element disposition region 76 provided along the first side 70s1. The multiple sensing elements 50 are arranged along the first side 70s1 in the first element disposition region 76. According to the pressure sensor 124 as well, a highly-sensitive pressure sensor is obtained.

Figure 27A:
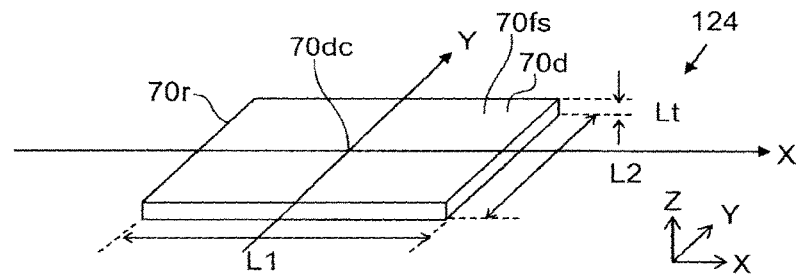
FIG. 27A and FIG. 27B are schematic views illustrating the configuration and characteristics of another pressure sensor according to the second embodiment.
Figure 27B:
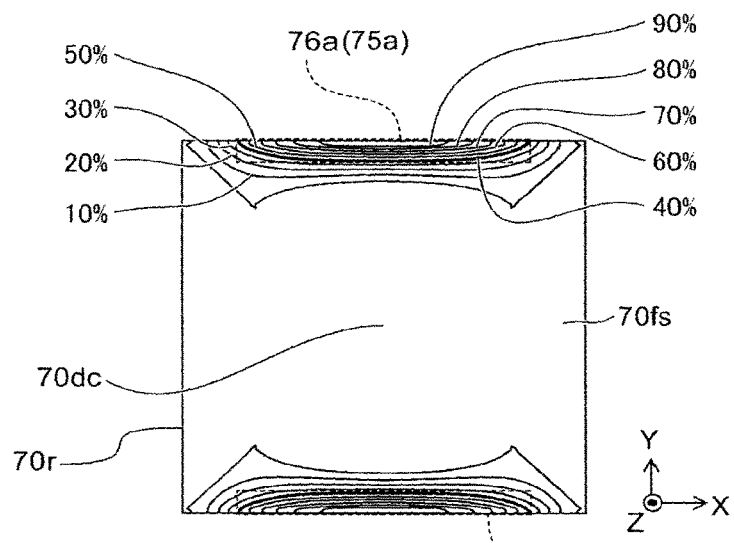

FIG. 27A and FIG. 27B are schematic views illustrating the configuration and characteristics of another pressure sensor according to the second embodiment.

FIG. 27A is a schematic perspective view illustrating the film part 70d of the pressure sensor 124. In the pressure sensor 124, the first length L1 is 500 µm; the second length L2 also is 500 µm; and the thickness Lt is 2 µm.

FIG. 27B illustrates the distribution in the X-Y plane of the anisotropic strain Δε occurring in the film part 70d.

As shown in FIG. 27A, in the pressure sensor 124 as well, the end portion anisotropic strain occurrence region 75a having a large surface area is obtained.

In the pressure sensor 124 as well, the multiple sensing elements 50 are provided on the portions of the film surface 70fs overlapping the first region 78a and the second region 78b. Also, the positions along the first direction (the X-axis direction) of the at least two of the multiple sensing elements 50 provided in the regions of the film surface 70fs overlapping the first region 78a and the second region 78b are different from each other.

Third Embodiment

Figure 28:
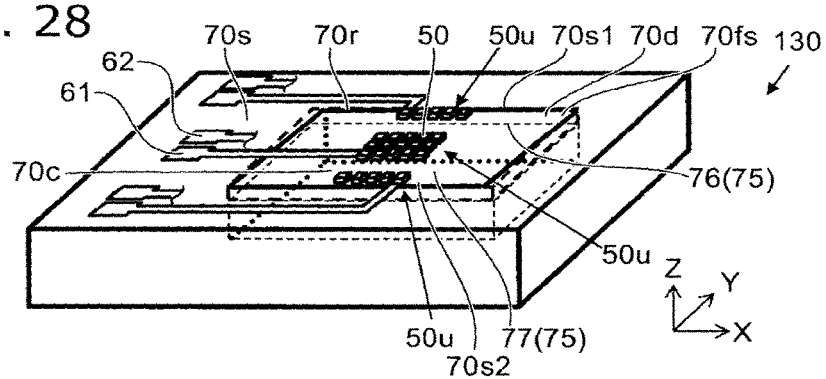
FIG. 28 is a schematic perspective view illustrating a pressure sensor according to a third embodiment.

FIG. 28 is a schematic perspective view illustrating a pressure sensor according to a third embodiment.

As shown in FIG. 28, the multiple sensing units 50u are provided in the pressure sensor 130 according to the embodiment. One sensing unit 50u is provided on the central portion 70c of the film part 70d. Another sensing unit 50u is provided on the first element disposition region 76. One other sensing unit 50u is provided on the second element disposition region 77. In the example, the first element disposition region 76 is provided along the first side 70s1 (the long side); and the second element disposition region 77 is provided along the second side 70s2 (the long side). The positions along the first direction of at least two of the multiple sensing elements 50 are different from each other.

Figure 29:
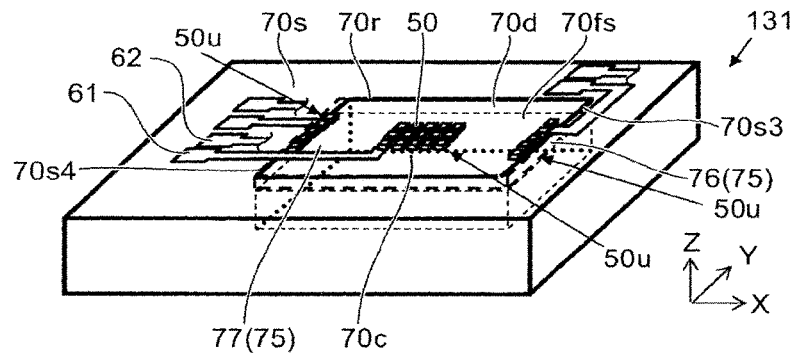
FIG. 29 is a schematic perspective view illustrating another pressure sensor according to the third embodiment.

FIG. 29 is a schematic perspective view illustrating another pressure sensor according to the third embodiment.

In the pressure sensor 131 according to the embodiment as shown in FIG. 29, the multiple sensing units 50u are provided on the central portion 70c, the first element disposition region 76, and the second element disposition region 77. In the example, the first element disposition region 76 is provided along the third side 70s3 (the short side); and the second element disposition region 77 is provided along the fourth side 70s4 (the short side).

Figure 30:
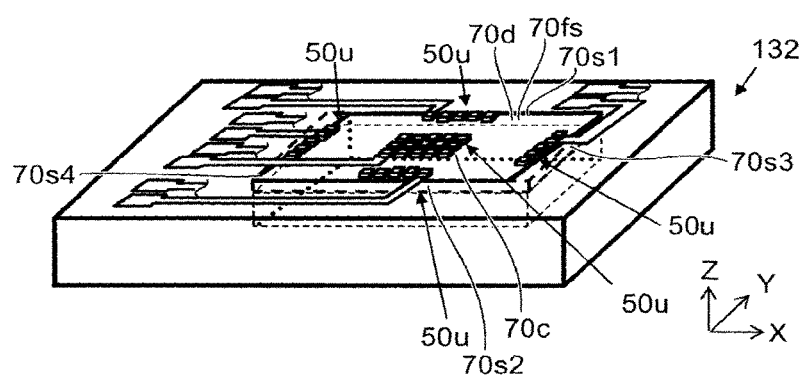
FIG. 30 is a schematic perspective view illustrating another pressure sensor according to the third embodiment.

FIG. 30 is a schematic perspective view illustrating another pressure sensor according to the third embodiment.

In the pressure sensor 132 according to the embodiment as shown in FIG. 30, the sensing unit 50u is provided on the central portion 70c. Further, element disposition regions are provided along the first to fourth sides 70s1 to 70s4; and the sensing units 50u are provided on the element disposition regions.

Figure 31:
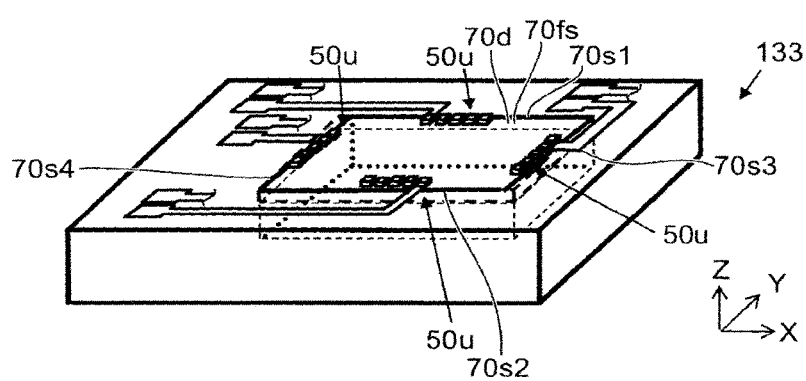
FIG. 31 is a schematic perspective view illustrating another pressure sensor according to the third embodiment.

FIG. 31 is a schematic perspective view illustrating another pressure sensor according to the third embodiment.

In the pressure sensor 133 according to the embodiment as shown in FIG. 31, element disposition regions are provided along the first to fourth sides 70s1 to 70s4; and the sensing units 50u are provided on the element disposition regions.

In the pressure sensors 130 to 133, the planar configuration of the film part 70d is a rectangle. The planar configuration of the film part 70d may be an ellipse. Or, the planar configuration of the film part 70d may be a square.

Figure 32:
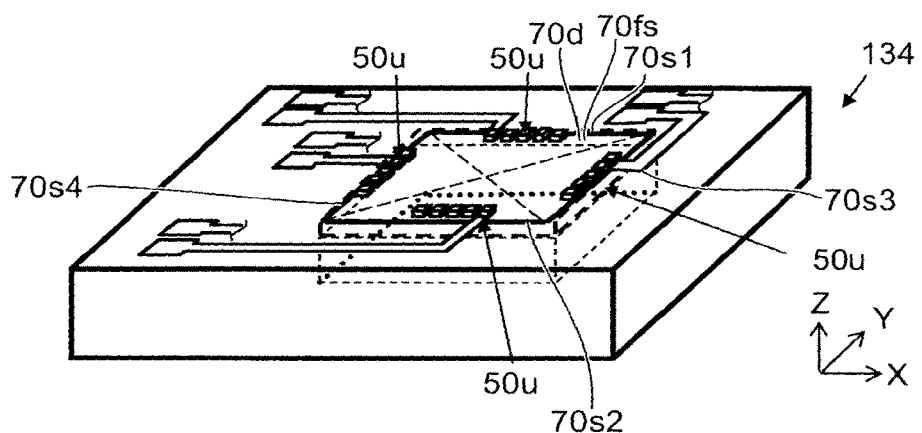
FIG. 32 is a schematic perspective view illustrating another pressure sensor according to the third embodiment.

FIG. 32 is a schematic perspective view illustrating another pressure sensor according to the third embodiment.

In the pressure sensor 134 according to the embodiment as shown in FIG. 32, the planar configuration of the film part 70d is a square. Element disposition regions are provided along the first to fourth sides 70s1 to 70s4; and the sensing units 50u are provided on the element disposition regions.

In the pressure sensors 130 to 134, the multiple sensing elements 50 included in the sensing unit 50u are arranged along the sides (the first to fourth sides 70s1 to 70s4, etc.) of the film part 70d.

An example of the sensing element used in the pressure sensors according to the first to third embodiments will now be described.

Herein, "material A/material B" indicates the state in which a layer of material B is provided on a layer of material A.

Figure 33:
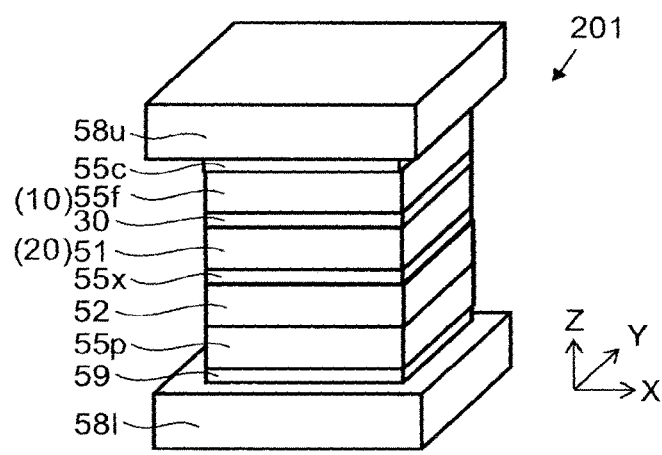
FIG. 33 is a schematic perspective view illustrating the sensing element used in the embodiment.

FIG. 33 is a schematic perspective view illustrating the sensing element used in the embodiment.

As shown in FIG. 33, the sensing element 201 used in the embodiment includes a lower electrode 58l, a foundation layer 59, a pinning layer 55p, a second magnetization fixed layer 52, a magnetic coupling layer 55x, a first magnetization fixed layer 51, the spacer layer 30, a magnetization free layer 55f, a capping layer 55c, and an upper electrode 58u arranged in order.

In the example, the magnetization free layer 55f corresponds to the first magnetic layer 10; and the first magnetization fixed layer 51 corresponds to the second magnetic layer 20. The sensing element 201 is a bottom spin-valve type element.

The foundation layer 59 includes, for example, Ta/Ru. The thickness (the length in the Z-axis direction) of the Ta layer is, for example, 3 nm. The thickness of the Ru layer is, for example, 2 nm.

The pinning layer 55p includes, for example, an IrMn layer having a thickness of 7 nm. The second magnetization fixed layer 52 includes, for example, a $Co_{75}Fe_{25}$ layer having a thickness of 2.5 nm. The magnetic coupling layer 55x includes, for example, a Ru layer having a thickness of 0.9 nm.

The first magnetization fixed layer 51 includes, for example, a $Co_{40}Fe_{40}B_{20}$ layer having a thickness of 3 nm. The spacer layer 30 includes, for example, a MgO layer having a thickness of 1.5 nm. The magnetization free layer 55f includes, for example, $Co_{40}Fe_{40}B_{20}/Fe_{80}Ga_{20}$. The thickness of the $Co_{40}Fe_{40}B_{20}$ layer is about 2 nm. The thickness of the $Fe_{80}Ga_{20}$ layer is 4 nm.

The capping layer 55c includes, for example, Ta/Ru. The thickness of the Ta layer is, for example, 1 nm. The thickness of the Ru layer is, for example, 5 nm.

The lower electrode 58l and the upper electrode 58u include, for example, at least one selected from aluminum (Al), an aluminum copper alloy (Al—Cu), copper (Cu), silver (Ag), and gold (Au). A current can be caused to flow efficiently in the sensing element 50 by using such a material that has a relatively small electrical resistance as the lower electrode 58l and the upper electrode 58u.

The lower electrode 58l may have a structure in which at least one layer selected from Al, Al—Cu, Cu, Ag, and Au is provided between a capping layer (not shown) and a foundation layer (not shown) that are for the lower electrode 58l. For example, the lower electrode 58l includes tantalum (Ta)/copper (Cu)/tantalum (Ta), etc. For example, the adhesion between the film part and the lower electrode 58l can be improved by using Ta as the foundation layer for the lower electrode 58l. Titanium (Ti), titanium nitride (TiN), etc., may be used as the foundation layer for the lower electrode 58l.

Oxidization of the copper (Cu), etc., under the capping layer for the lower electrode 58l can be prevented by using Ta as the capping layer. Titanium (Ti), titanium nitride (TiN), etc., may be used as the capping layer for the lower electrode 58l.

The foundation layer 59 may include a stacked structure of a buffer layer (not shown) and a seed layer (not shown). For example, the buffer layer relaxes the irregularity of the surfaces of the lower electrode 58l and the film part and improves the crystallinity of the layers stacked on the buffer layer. For example, at least one selected from the group consisting of tantalum (Ta), titanium (Ti), vanadium (V), tungsten (W), zirconium (Zr), hafnium (Hf), and chrome (Cr) is used as the buffer layer. An alloy including at least one material selected from these materials may be used as the buffer layer.

It is favorable for the thickness of the buffer layer to be not less than 1 nm and not more than 10 nm. It is more favorable for the thickness of the buffer layer to be not less than 1 nm and not more than 5 nm. The buffering effect is lost when the thickness of the buffer layer is too thin. The thickness of the sensing element 50 becomes excessively thick when the thickness of the buffer layer is too thick. A seed layer may be formed on the buffer layer; and the seed layer may have a buffering effect. The buffer layer may be omitted. The buffer layer includes, for example, a Ta layer having a thickness of 3 nm.

A not-shown seed layer controls the crystal orientation of the layers stacked on the seed layer. The seed layer controls the crystal grain size of the layers stacked on the seed layer. A metal or the like having a fcc structure (face-centered cubic structure), a hcp structure (hexagonal close-packed structure), or a bcc structure (body-centered cubic structure) is used as the seed layer.

By using ruthenium (Ru) having a hcp structure, NiFe having a fcc structure, or Cu having a fcc structure as the seed layer, for example, the crystal orientation of the spin-valve film on the seed layer can have a fcc (111) orientation. The seed layer includes, for example, a Cu layer having a thickness of 2 nm or a Ru layer having a thickness of 2 nm. To improve the crystal orientation of the layers formed on the seed layer, it is favorable for the thickness of the seed layer to be not less than 1 nm and not more than 5 nm. It is more favorable for the thickness of the seed layer to be not less than 1 nm and not more than 3 nm. Thereby, the function as the seed layer of improving the crystal orientation is sufficiently realized. On the other hand, for example, in the case where it is unnecessary to cause the layers formed on the seed layer to have a crystal orientation (e.g., in the case where an amorphous magnetization free layer 55f is formed, etc.), the seed layer may be omitted. For example, a Cu layer having a thickness of 2 nm is used as the seed layer.

For example, the pinning layer 55p provides unidirectional anisotropy to the ferromagnetic layer of the second magnetization fixed layer 52 formed on the pinning layer 55p to fix the magnetization. The pinning layer 55p includes, for example, an antiferromagnetic layer. The pinning layer 55p includes, for example, at least one selected from the group consisting of IrMn, PtMn, PdPtMn, and RuRhMn. The thickness of the pinning layer 55p is set appropriately to provide unidirectional anisotropy of sufficient strength.

In the case where PtMn or PdPtMn is used as the pinning layer 55p, it is favorable for the thickness of the pinning layer 55p to be not less than 8 nm and not more than 20 nm. It is more favorable for the thickness of the pinning layer 55p to be not less than 10 nm and not more than 15 nm. The pinning layer 55p that provides the unidirectional anisotropy can be thinner in the case where IrMn is used as the pinning layer 55p than in the case where PtMn is used as the pinning layer 55p. In such a case, it is favorable for the thickness of the pinning layer 55p to be not less than 4 nm and not more than 18 nm. It is more favorable for the thickness of the pinning layer 55p to be not less than 5 nm and not more than 15 nm. The pinning layer 55p includes, for example, an $Ir_{22}Mn_{78}$ layer having a thickness of 7 nm.

A hard magnetic layer may be used as the pinning layer 55p. For example, CoPt (having a proportion of Co of not less than 50 at. % and not more than 85 at. %), $(Co_xPt_{100-x})_{100-y}Cr_y$ (x being not less than 50 at. % and not more than 85 at. % and y being not less than 0 at. % and not more than 40 at. %), FePt (having a proportion of Pt of not less than 40 at. % and not more than 60 at. %), etc., may be used as the hard magnetic layer.

The second magnetization fixed layer 52 includes, for example, a $Co_xFe_{100-x}$ alloy (x being not less than 0 at. % and not more than 100 at. %), a $Ni_xFe_{100-x}$ alloy (x being not less than 0 at. % and not more than 100 at. %), or a material in which a nonmagnetic element is added to these alloys. For example, at least one selected from the group consisting of Co, Fe, and Ni is used as the second magnetization fixed layer 52. An alloy including at least one material selected from these materials may be used as the second magnetization fixed layer 52. A $(Co_xFe_{100-x})_{100-y}B_y$ alloy (x being not less than 0 at. % and not more than 100 at. % and y being not less than 0 at. % and not more than 30 at. %) may be used as the second magnetization fixed layer 52. By using an amorphous alloy of $(Co_xFe_{100-x})_{100-y}B_y$ as the second magnetization fixed layer 52, the fluctuation between the sensing elements 50 can be suppressed even in the case where the sensing element 50 is small.

It is favorable for the thickness of the second magnetization fixed layer 52 to be, for example, not less than 1.5 nm and not more than 5 nm. Thereby, for example, the strength of the unidirectional anisotropic magnetic field due to the pinning layer 55p can be stronger. For example, the strength of the antiferromagnetic coupling magnetic field between the second magnetization fixed layer 52 and the first magnetization fixed layer 51 via the magnetic coupling layer 55x formed on the second magnetization fixed layer 52 can be stronger. It is favorable for the magnetic thickness of the second magnetization fixed layer 52 (the product of a saturation magnetization Bs and a thickness t (Bs·t)) to be substantially equal to the magnetic thickness of the first magnetization fixed layer 51.

For a thin film, the saturation magnetization of $Co_{40}Fe_{40}B_{20}$ is about 1.9 T (teslas). For example, the magnetic thickness of the first magnetization fixed layer 51 is 1.9 T×3 nm which is 5.7 Tnm in the case where a $Co_{40}Fe_{40}B_{20}$ layer having a thickness of 3 nm is used as the first magnetization fixed layer 51. On the other hand, the saturation magnetization of $Co_{75}Fe_{25}$ is about 2.1 T. The thickness of the second magnetization fixed layer 52 to obtain a magnetic thickness that is equal to that recited above is 5.7 Tnm/2.1 T which is 2.7 nm. In such a case, it is favorable for the second magnetization fixed layer 52 to include $Co_{75}Fe_{25}$ having a thickness of about 2.7 nm. For example, a $Co_{75}Fe_{25}$ layer having a thickness of 2.5 nm is used as the second magnetization fixed layer 52.

In the sensing element 201, a synthetic pinned structure of the second magnetization fixed layer 52, the magnetic coupling layer 55x, and the first magnetization fixed layer 51 is used. Instead, a single pinned structure made of one magnetization fixed layer may be used. In the case where the single pinned structure is used, for example, a $Co_{40}Fe_{40}B_{20}$ layer having a thickness of 3 nm is used as the magnetization fixed layer. The same material as the first magnetization fixed layer 51 described above may be used as the ferromagnetic layer used in the magnetization fixed layer of the single pinned structure.

The magnetic coupling layer 55x causes antiferromagnetic coupling to occur between the second magnetization fixed layer 52 and the first magnetization fixed layer 51. The magnetic coupling layer 55x forms a synthetic pinned structure. For example, Ru is used as the magnetic coupling layer 55x. It is favorable for the thickness of the magnetic coupling layer 55x to be not less than 0.8 nm and not more than 1 nm. A material other than Ru may be used as the magnetic coupling layer if the material can cause sufficient antiferromagnetic coupling to occur between the second magnetization fixed layer 52 and the first magnetization fixed layer 51. The thickness of the magnetic coupling layer 55x may be set to be a thickness not less than 0.8 nm and not more than 1 nm that corresponds to the second peak (2nd peak) of RKKY (Ruderman-Kittel-Kasuya-Yosida) coupling. Further, the thickness of the magnetic coupling layer 55x may be set to be a thickness not less than 0.3 nm and not more than 0.6 nm that corresponds to the first peak (1st peak) of RKKY coupling. For example, Ru having a thickness of 0.9 nm is used as the magnetic coupling layer 55x. Thereby, highly reliable coupling is obtained more stably.

The magnetic layer that is used in the first magnetization fixed layer 51 contributes directly to the MR effect. For example, a Co—Fe—B alloy is used as the first magnetization fixed layer 51. Specifically, a $(Co_xFe_{100-x})_{100-y}B_y$ alloy (x being not less than 0 at. % and not more than 100 at. % and y being not less than 0 at. % and not more than 30 at. %) may be used as the first magnetization fixed layer 51. In the case where an amorphous alloy of $(Co_xFe_{100-x})_{100-y}B_y$ is used as the first magnetization fixed layer 51, for example, the fluctuation between the elements caused by the crystal grains can be suppressed even in the case where the sensing element is small.

The layer (e.g., a tunneling insulating layer (not shown)) that is formed on the first magnetization fixed layer 51 can be planarized. By planarizing the tunneling insulating layer, the defect density of the tunneling insulating layer can be reduced. Thereby, a higher MR ratio having a lower resistance per area is obtained. For example, in the case where MgO is used as the material of the tunneling insulating layer, the (100) orientation of the MgO layer formed on the tunneling insulating layer can be improved by using an amorphous alloy of $(Co_xFe_{100-x})_{100-y}B_y$. A higher MR ratio is obtained by improving the (100) orientation of the MgO layer. The $(Co_xFe_{100-x})_{100-y}B_y$ alloy crystallizes using the (100) plane of the MgO layer as a template in the annealing. Therefore, good crystal conformation between the MgO and $(Co_xFe_{100-x})_{100-y}B_y$ alloy is obtained. A higher MR ratio is obtained by obtaining good crystal conformation.

Other than the Co—Fe—B alloy, for example, an Fe—Co alloy may be used as the first magnetization fixed layer 51.

The MR ratio increases as the thickness of the first magnetization fixed layer 51 increases. A thinner first magnetization fixed layer 51 is favorable to obtain a larger magnetization fixed field. A trade-off relationship between the MR ratio and the magnetization fixed field exists for the thickness of the first magnetization fixed layer 51. In the case where the Co—Fe—B alloy is used as the first magnetization fixed layer 51, it is favorable for the thickness of the first magnetization fixed layer 51 to be not less than 1.5 nm and not more than 5 nm. It is more favorable for the thickness of the first magnetization fixed layer 51 to be not less than 2.0 nm and not more than 4 nm.

Other than the materials described above, the first magnetization fixed layer 51 may include a $Co_{90}Fe_{10}$ alloy having a fcc structure, Co having a hcp structure, or a Co alloy having a hcp structure. At least one selected from the group consisting of Co, Fe, and Ni is used as the first magnetization fixed layer 51. An alloy including at least one material selected from these materials is used as the first magnetization fixed layer 51. For example, a higher MR ratio is obtained by using an FeCo alloy material having a bcc structure, a Co alloy including a cobalt composition not less than 50 at. %, or a material having a Ni composition not less than 50 at. % as the first magnetization fixed layer 51. A Heusler magnetic alloy layer such as $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, etc., may be used as the first magnetization fixed layer 51. For example, a $Co_{40}Fe_{40}B_{20}$ layer having a thickness of 3 nm is used as the first magnetization fixed layer 51.

The spacer layer 30 divides the magnetic coupling between the first magnetization fixed layer 51 and the magnetization free layer 55f. The spacer layer 30 includes a metal, an insulator, or a semiconductor. For example, Cu, Au, Ag, etc., may be used as the metal. In the case where the metal is used as the spacer layer 30, the thickness of the spacer layer 30 is, for example, not less than about 1 nm and not more than about 7 nm. For example, magnesium oxide (MgO, etc.), aluminum oxide ($Al_2O_3$, etc.), titanium oxide (TiO, etc.), zinc oxide (ZnO, etc.), gallium oxide (Ga—O), etc., may be used as the insulator or the semiconductor. In the case where the insulator or the semiconductor is used as the spacer layer 30, the thickness of the spacer layer 30 is, for example, not less than about 0.6 nm and not more than about 2.5 nm. For example, a CCP (Current-Confined-Path) spacer layer may be used as the spacer layer 30. In the case where the CCP spacer layer is used as the spacer layer, for example, a structure in which copper (Cu) metal paths are formed in an insulating layer of aluminum oxide ($Al_2O_3$) is used. For example, a MgO layer having a thickness of 1.5 nm is used as the spacer layer 30.

The magnetization free layer 55f includes a ferromagnet material. For example, an FeCo alloy, a NiFe alloy, etc., may be used as the material of the magnetization free layer 55f. Further, the magnetization free layer 55f may include a Co—Fe—B alloy, an Fe—Co—Si—B alloy, an Fe—Ga alloy having a large λs (magnetostriction constant), an Fe—Co—Ga alloy, a Tb-M-Fe alloy (M being at least one selected from the group consisting of Sm, Eu, Gd, Dy, Ho, and Er), a Tb-M1-Fe-M2 alloy (M1 being at least one selected from the group consisting of Sm, Eu, Gd, Dy, Ho, and Er and M2 being at least one selected from the group consisting of Ti, Cr, Mn, Co, Cu, Nb, Mo, W, and Ta), an Fe-M3-M4-B alloy (M3 being at least one selected from the group consisting of Ti, Cr, Mn, Co, Cu, Nb, Mo, W, and Ta and M4 being at least one selected from the group consisting of Ce, Pr, Nd, Sm, Tb, Dy, and Er), Ni, Fe—Al, ferrite ($Fe_3O_4$, $(FeCo)_3O_4$, etc.), and the like. The thickness of the magnetization free layer 55*f* is, for example, not less than 2 nm.

The magnetization free layer 55*f* may have a multilayered structure. The magnetization free layer 55*f* may have, for example, a two-layer structure. In the case where a tunneling insulating layer of MgO is used as the spacer layer 30, it is favorable to provide a layer of a Co—Fe—B alloy at the interface contacting the spacer layer 30. Thereby, a high magnetoresistance effect is obtained. In such a case, the layer of the Co—Fe—B alloy may be provided on the spacer layer 30; and an Fe—Co—Si—B alloy, an Fe—Ga alloy having a large λs, an Fe—Co—Ga alloy, a Tb-M-Fe alloy (M being at least one selected from the group consisting of Sm, Eu, Gd, Dy, Ho, and Er), a Tb-M1-Fe-M2 alloy (M1 being at least one selected from the group consisting of Sm, Eu, Gd, Dy, Ho, and Er and M2 being at least one selected from the group consisting of Ti, Cr, Mn, Co, Cu, Nb, Mo, W, and Ta), an Fe-M3-M4-B alloy (M3 being at least one selected from the group consisting of Ti, Cr, Mn, Co, Cu, Nb, Mo, W, and Ta and M4 being at least one selected from the group consisting of Ce, Pr, Nd, Sm, Tb, Dy, and Er), Ni, Fe—Al, ferrite ($Fe_3O_4$, $(FeCo)_3O_4$, etc.), and the like may be formed on the layer of Co—Fe—B alloy. For example, the magnetization free layer 55*f* includes $Co_{40}Fe_{40}B_{20}$/$Fe_{80}Ga_{20}$. The thickness of the $Co_{40}Fe_{40}B_{20}$ is, for example, 2 nm. The thickness of the $Fe_{80}Ga_{20}$ is, for example, 4 nm. λs is, for example, greater than 100 ppm.

The capping layer 55*c* protects the layers provided under the capping layer 55*c*. The capping layer 55*c* includes, for example, multiple metal layers. The capping layer 55*c* includes, for example, a two-layer structure of a Ta layer and a Ru layer (Ta/Ru). The thickness of the Ta layer is, for example, 1 nm; and the thickness of the Ru layer is, for example, 5 nm. Other metal layers may be provided instead of the Ta layer and/or the Ru layer as the capping layer 55*c*. The configuration of the capping layer 55*c* is arbitrary. The capping layer 55*c* may include, for example, a nonmagnetic material. Other materials may be used as the capping layer 55*c* if the layers provided under the capping layer 55*c* can be protected.

Figure 34:
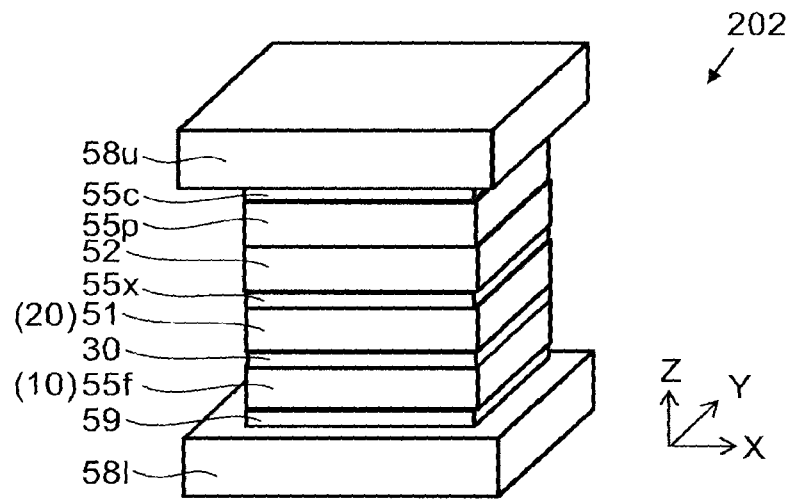
FIG. 34 is a schematic perspective view illustrating another sensing element used in the embodiment.

FIG. 34 is a schematic perspective view illustrating another sensing element used in the embodiment.

As shown in FIG. 34, the sensing element 202 used in the pressure sensor according to the embodiment includes the lower electrode 58*l*, the foundation layer 59, the magnetization free layer 55*f*, the spacer layer 30, the first magnetization fixed layer 51, the magnetic coupling layer 55*x*, the second magnetization fixed layer 52, the pinning layer 55*p*, the capping layer 55*c*, and the upper electrode 58*u* arranged in order.

In the example, the magnetization free layer 55*f* corresponds to the first magnetic layer 10; and the first magnetization fixed layer 51 corresponds to the second magnetic layer 20. The sensing element 202 is a top spin-valve type element.

The foundation layer 59 includes, for example, Ta/Ru. The thickness of the Ta layer is, for example, 3 nm. The thickness of the Ru layer is, for example, 2 nm.

The magnetization free layer 55*f* includes, for example, $Fe_{80}Ga_{20}$/$Co_{40}Fe_{40}B_{20}$. The thickness of the $Fe_{80}Ga_{20}$ layer is, for example, 4 nm. The thickness of the $Co_{40}Fe_{40}B_{20}$ layer is, for example, 2 nm.

The spacer layer 30 includes, for example, a MgO layer having a thickness of 1.5 nm. The first magnetization fixed layer 51 includes, for example, $Co_{40}Fe_{40}B_{20}$/$Fe_{50}Co_{50}$. The thickness of the $Co_{40}Fe_{40}B_{20}$ layer is, for example, 2 nm. The thickness of the $Fe_{50}Co_{50}$ layer is, for example, 1 nm. The magnetic coupling layer 55*x* includes, for example, a Ru layer having a thickness of 0.9 nm. The second magnetization fixed layer 52 includes, for example, a $Co_{75}Fe_{25}$ layer having a thickness of 2.5 nm. The pinning layer 55*p* includes, for example, an IrMn layer having a thickness of 7 nm.

The capping layer 55*c* includes Ta/Ru. The thickness of the Ta layer is, for example, 1 nm. The thickness of the Ru layer is, for example, 5 nm.

For example, the materials described in regard to the sensing element 201 may be used respectively in the layers included in the sensing element 202.

Figure 35:
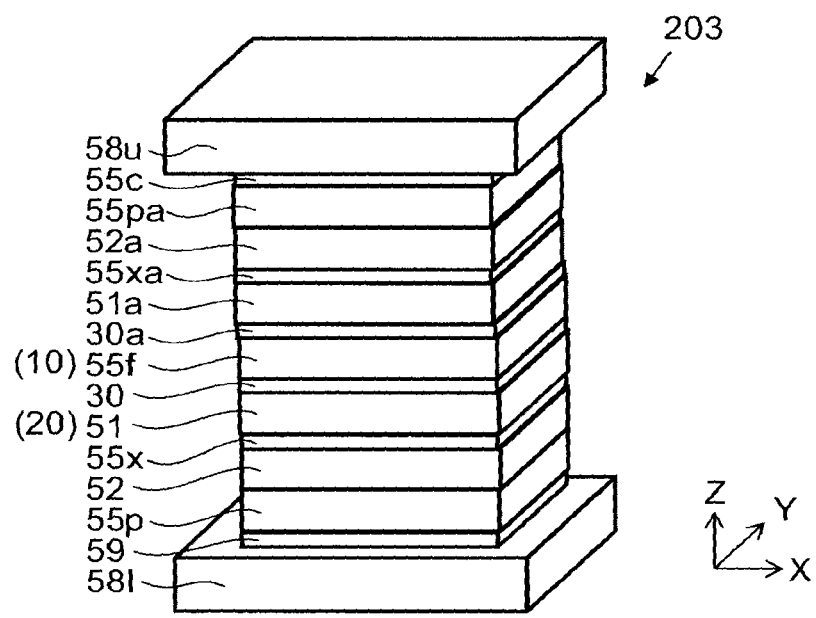
FIG. 35 is a schematic perspective view illustrating another sensing element used in the embodiment.

FIG. 35 is a schematic perspective view illustrating another sensing element used in the embodiment.

As shown in FIG. 35, the sensing element 203 used in the pressure sensor according to the embodiment includes the lower electrode 58*l*, the foundation layer 59, the pinning layer 55*p*, the second magnetization fixed layer 52, the magnetic coupling layer 55*x*, the first magnetization fixed layer 51, the spacer layer 30, the magnetization free layer 55*f*, a spacer layer 30*a*, a first magnetization fixed layer 51*a*, a magnetic coupling layer 55*xa*, a second magnetization fixed layer 52*a*, a pinning layer 55*pa*, the capping layer 55*c*, and the upper electrode 58*u* arranged in order.

The magnetization free layer 55*f* corresponds to the first magnetic layer 10; and the first magnetization fixed layer 51 corresponds to the second magnetic layer 20. In the sensing elements 201 and 202 described above, the magnetization fixed layer is disposed at one surface of the magnetization free layer 55*f*. In the sensing element 203, the magnetization free layer 55*f* is disposed between two magnetization fixed layers. The sensing element 203 is a dual spin-valve type element.

The foundation layer 59 includes, for example, Ta/Ru. The thickness of the Ta layer is, for example, 3 nm. The thickness of the Ru layer is, for example, 2 nm. The pinning layer 55*p* includes, for example, an IrMn layer having a thickness of 7 nm. The second magnetization fixed layer 52 includes, for example, a $Co_{75}Fe_{25}$ layer having a thickness of 2.5 nm. The magnetic coupling layer 55*x* includes, for example, a Ru layer having a thickness of 0.9 nm. The first magnetization fixed layer 51 includes, for example, a $Co_{40}Fe_{40}B_{20}$ layer having a thickness of 3 nm. The spacer layer 30 includes, for example, a MgO layer having a thickness of 1.5 nm.

The magnetization free layer 55*f* includes, for example, $Co_{40}Fe_{40}B_{20}$/$Fe_{80}Ga_{20}$/$Co_{40}Fe_{40}B_{20}$. The thickness of the $Fe_{80}Ga_{20}$ layer is, for example, 4 nm. The thicknesses of the two $Co_{40}Fe_{40}B_{20}$ layers are, for example, 2 nm.

The spacer layer 30*a* includes, for example, a MgO layer having a thickness of 1.5 nm. The first magnetization fixed layer 51*a* includes, for example, $Co_{40}Fe_{40}B_{20}$/$Fe_{50}Co_{50}$.

The thickness of the $Co_{40}Fe_{40}B_{20}$ layer is, for example, 2 nm. The thickness of the $Fe_{50}Co_{50}$ layer is, for example, 1 nm. The magnetic coupling layer 55xa includes, for example, a Ru layer having a thickness of 0.9 nm. The second magnetization fixed layer 52a includes, for example, a $Co_{75}Fe_{25}$ layer having a thickness of 2.5 nm. The pinning layer 55pa includes, for example, an IrMn layer having a thickness of 7 nm.

The capping layer 55c includes Ta/Ru. The thickness of the Ta layer is, for example, 1 nm. The thickness of the Ru layer is, for example, 5 nm.

For example, the materials described in regard to the sensing element 201 may be used in the layers included in the sensing element 203.

Figure 36:
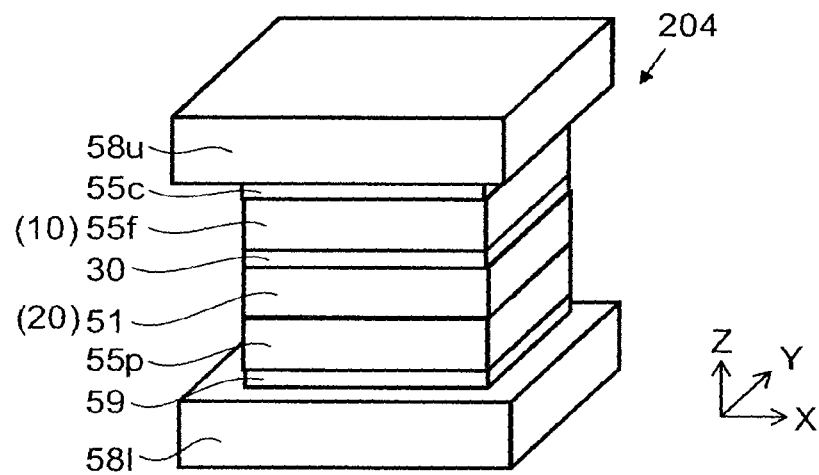
FIG. 36 is a schematic perspective view illustrating another sensing element used in the embodiment.

FIG. 36 is a schematic perspective view illustrating another sensing element used in the embodiment.

As shown in FIG. 36, the sensing element 204 used in the pressure sensor according to the embodiment includes the lower electrode 58l, the foundation layer 59, the pinning layer 55p, the first magnetization fixed layer 51, the spacer layer 30, the magnetization free layer 55f, the capping layer 55c, and the upper electrode 58u arranged in order.

The magnetization free layer 55f corresponds to the first magnetic layer 10; and the first magnetization fixed layer 51 corresponds to the second magnetic layer 20. In the sensing elements 201 and 202 described above, a structure that uses the second magnetization fixed layer 52, the magnetic coupling layer 55x, and the first magnetization fixed layer 51 is used. In the sensing element 204, a single pinned structure that uses a single magnetization fixed layer is used.

The foundation layer includes, for example, Ta/Ru. The thickness of the Ta layer is, for example, 3 nm. The thickness of the Ru layer is, for example, 2 nm. The pinning layer 55p includes, for example, an IrMn layer having a thickness of 7 nm. The first magnetization fixed layer 51 includes, for example, a $Co_{40}Fe_{40}B_{20}$ layer having a thickness of 3 nm. The spacer layer 30 includes, for example, a MgO layer having a thickness of 1.5 nm.

The magnetization free layer 55f includes, for example, $Co_{40}Fe_{40}B_{20}/Fe_{80}Ga_{20}$. The thickness of the $Fe_{80}Ga_{20}$ layer is, for example, 4 nm. The thickness of the $Co_{40}Fe_{40}B_{20}$ layer is, for example, 2 nm.

The capping layer 55c includes Ta/Ru. The thickness of the Ta layer is, for example, 1 nm. The thickness of the Ru layer is, for example, 5 nm.

For example, the materials described in regard to the sensing element 201 may be used in the layers included in the sensing element 204.

Figure 37:
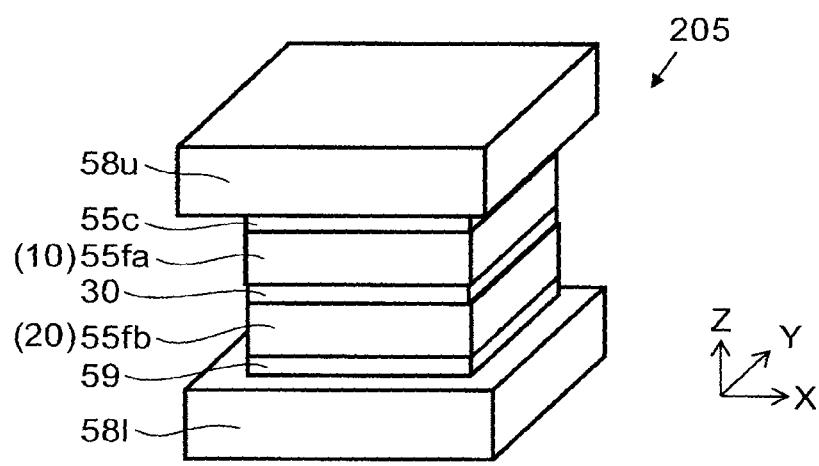
FIG. 37 is a schematic perspective view illustrating another sensing element used in the embodiment.

FIG. 37 is a schematic perspective view illustrating another sensing element used in the embodiment.

As shown in FIG. 37, the sensing element 205 used in the pressure sensor according to the embodiment includes the lower electrode 58l, the foundation layer 59, a second magnetization free layer 55fb, the spacer layer 30, a first magnetization free layer 55fa, the capping layer 55c, and the upper electrode 58u arranged in order.

The second magnetization free layer 55fb corresponds to the second magnetic layer 20; and the first magnetization free layer 55fa corresponds to the first magnetic layer 10. In the sensing elements 201 to 204 described above, the reference layer used in the second magnetic layer 20 is a magnetization fixed layer. In the sensing element 205, the reference layer used in the second magnetic layer 20 is a magnetization free layer.

The foundation layer 59 includes, for example, Ta/Ru. The thickness of the Ta layer is, for example, 3 nm. The thickness of the Ru layer is, for example, 2 nm.

The second magnetization free layer 55fb includes, for example, a $Co_{40}Fe_{40}B_{20}$ layer having a thickness of 4 nm. The spacer layer 30 includes, for example, a MgO layer having a thickness of 1.5 nm.

The first magnetization free layer 55fa includes, for example, $Co_{40}Fe_{40}B_{20}$. The thickness of the $Co_{40}Fe_{40}B_{20}$ layer is, for example, 4 nm.

The capping layer 55c includes Ta/Ru. The thickness of the Ta layer is, for example, 1 nm. The thickness of the Ru layer is, for example, 5 nm.

For example, the materials described in regard to the sensing element 201 may be used in the layers included in the sensing element 205.

As in the sensing element 205, the relative angle between the magnetization of the second magnetization free layer and the magnetization of the first magnetization free layer changes due to the strain even in the case where the stacked structure of the second magnetization free layer 55fb, the spacer layer 30, and the first magnetization free layer 55fa is used. Thereby, it is possible to function as a strain sensor. In such a case, the value of the magnetostriction of the second magnetization free layer 55fb and the value of the magnetostriction of the first magnetization free layer 55fa are designed to be different from each other. Thereby, the relative angle between the magnetization of the second magnetization free layer and the magnetization of the first magnetization free layer changes due to the strain.

Figure 38:
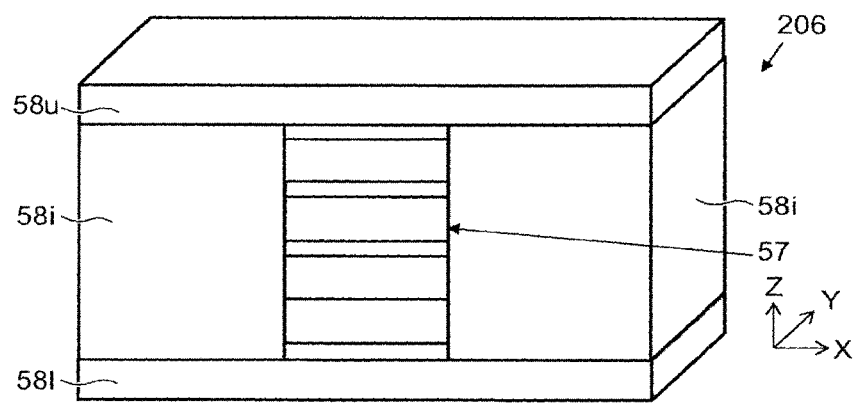
FIG. 38 is a schematic perspective view illustrating another sensing element used in the embodiment.

FIG. 38 is a schematic perspective view illustrating another sensing element used in the embodiment.

As illustrated in FIG. 38, an insulating layer 58i is provided in the sensing element 206. Namely, two insulating layers 58i (insulating portions) that are separated from each other are provided between the lower electrode 58l and the upper electrode 58u; and a stacked body 57 is disposed between the two insulating layers 58i. The stacked body 57 is disposed between the lower electrode 58l and the upper electrode 58u. In the case of the sensing element 201, the stacked body 57 includes the foundation layer 59, the pinning layer 55p, the second magnetization fixed layer 52, the magnetic coupling layer 55x, the first magnetization fixed layer 51, the spacer layer 30, the magnetization free layer 55f, and the capping layer 55c. In other words, the insulating layers 58i are provided to oppose the side walls of the stacked body 57.

The insulating layers 58i may include, for example, aluminum oxide (e.g., $Al_2O_3$), silicon oxide (e.g., $SiO_2$), etc. Leak current around the stacked body 57 can be suppressed by the insulating layers 58i.

The insulating layers 58i recited above are applicable also to any of the sensing elements 201 to 205.

Figure 39:
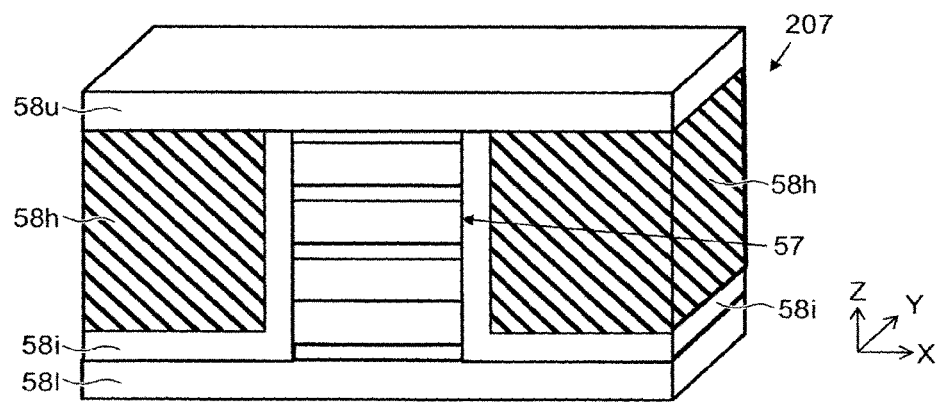
FIG. 39 is a schematic perspective view illustrating another sensing element used in the embodiment.

FIG. 39 is a schematic perspective view illustrating another sensing element used in the embodiment.

As illustrated in FIG. 39, a hard bias layer 58h is further provided in the sensing element 207. Namely, two hard bias layers 58h (hard bias portions) that are separated from each other are provided between the lower electrode 58l and the upper electrode 58u; and the stacked body 57 is disposed between the two hard bias layers 58h. The insulating layers 58i are disposed between the hard bias layers 58h and the stacked body 57. Also, in the example, the insulating layers 58i extend between the hard bias layers 58h and the lower electrode 58l.

The hard bias layers 58h cause at least one selected from the magnetization of the first magnetic layer 10 and the magnetization of the second magnetic layer 20 to be in the desired direction by the magnetization of the hard bias layers 58h. By the hard bias layers 58h, at least one selected from the magnetization of the first magnetic layer 10 and the magnetization of the second magnetic layer can be set to be in the desired direction in the state in which the pressure is not applied to the film part 70d.

The hard bias layer 58h includes, for example, a hard ferromagnetic material having a relatively high magnetic anisotropy such as CoPt, CoCrPt, FePt, etc. The hard bias layer 58h may include a structure in which a layer of a soft magnetic material such as FeCo, Fe, etc., is stacked with an antiferromagnetic layer. In such a case, the magnetization is along a prescribed direction due to exchange coupling. The thickness of the hard bias layer 58h (the length along the direction from the lower electrode 58l toward the upper electrode 58u) is, for example, not less than 5 nm and not more than 50 nm.

The hard bias layer 58h and the insulating layer 58i recited above are applicable also to any of the sensing elements 201 to 205.

The sensing elements 201 to 207 recited above can be used as the sensing element 50 according to the embodiment.

In the embodiment, the sensing element functions sufficiently as the pressure sensor even in the case where the sensing element is small. For example, the surface area (the surface area when projected onto the X-Y plane) of the sensing element 50 can be 1/100 of the surface area of the film part 70d or less. For example, in the case where the widths of the film part 70d (the first length L1 and the second length L2) are about 100 µm, the length of the sensing element 50 in the first direction when projected onto the X-Y plane can be 10 µm or less. For example, in the case of a circle, the diameter can be about 10 µm or less. For example, in the case where the width of the film part 70d is about 500 µm, the length of the sensing element 50 in the first direction when projected onto the X-Y plane can be 50 µm or less. For example, in the case of a circle, the diameter can be about 50 µm or less. For example, the length of the sensing element 50 in the first direction when projected onto the X-Y plane is not less than 0.1 µm and not more than 50 µm. By using a small sensing element 50, the degrees of freedom of the number of the sensing elements 50 to be provided increase.

The planar configuration of the sensing element 50 may be a square, a rectangle, a flattened circle (including an ellipse), or a circle. The planar configuration of the sensing element 50 is arbitrary.

An example of a method for manufacturing a pressure sensor according to the embodiment will now be described. An example of a method for manufacturing the pressure sensor 110 is described below.

FIG. 40A to FIG. 40E are schematic cross-sectional views in order of the processes, illustrating the method for manufacturing the pressure sensor according to the embodiment.

Figure 40A:
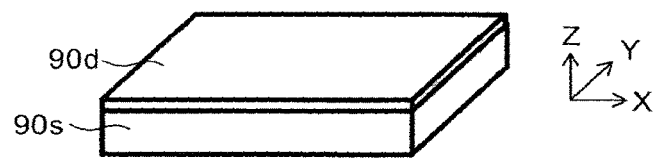
FIG. 40A to FIG. 40E are schematic cross-sectional views in order of the processes, illustrating the method for manufacturing the pressure sensor according to the embodiment.

As shown in FIG. 40A, a thin film 90d is formed on a substrate 90s (e.g., a Si substrate). The substrate 90s is used to form the support unit 70s. The thin film 90d is used to form the film part 70d.

For example, a thin film 90d of $SiO_x$/Si is formed on the Si substrate by sputtering. A metal layer such as a $SiO_x$ single layer, a SiN single layer, Al, etc., may be used as the thin film 90d. Or, a flexible plastic material such as polyimide, a paraxylene polymer, etc., may be used as the thin film 90d. SOI (Silicon On Insulator) substrates may be used as the substrate 90s and the thin film 90d. In the SOI, for example, a stacked film of $SiO_2$/Si is formed on the Si substrate by bonding the substrates.

Figure 40B:
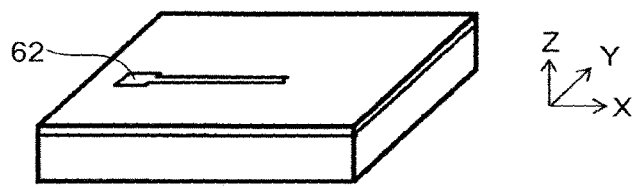

The second interconnect 62 is formed as shown in FIG. 40B. In this process, a conductive film that is used to form the second interconnect 62 is formed; and the conductive film is patterned by photolithography and etching. Lift-off is applicable in the case where an insulating film is filled around the second interconnect 62. In the lift-off, for example, the insulating film is formed on the entire surface after etching the pattern of the second interconnect 62 and prior to peeling the resist; and the resist is removed subsequently.

Figure 40C:
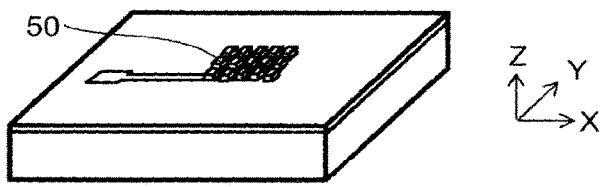

The sensing element 50 is formed as shown in FIG. 40C. In this process, a stacked film that is used to form the sensing element 50 is formed; and the stacked film is patterned by photolithography and etching. Lift-off is applicable in the case where the side wall of the stacked body 57 of the sensing element 50 is buried in the insulating layer 58i. In the lift-off, for example, the insulating layer 58i is formed on the entire surface after patterning the stacked body 57 and prior to peeling the resist; and the resist is removed subsequently.

Figure 40D:
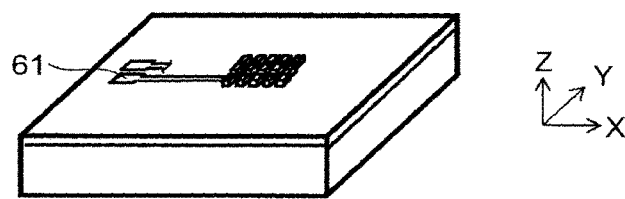

The first interconnect 61 is formed as shown in FIG. 40D. In this process, a conductive film that is used to form the first interconnect 61 is formed; and the conductive film is patterned by photolithography and etching. Lift-off is applicable in the case where an insulating film is filled around the first interconnect 61. In the lift-off, the insulating film is formed on the entire surface after patterning the first interconnect 61 and prior to peeling the resist; and the resist is removed subsequently.

Figure 40E:
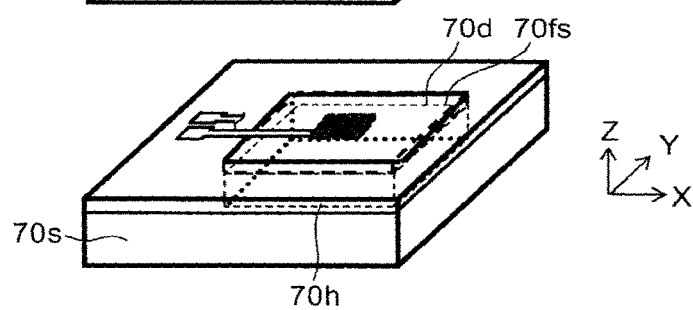

As shown in FIG. 40E, the hollow portion 70h is made by performing etching from the back surface of the substrate 90s. Thereby, the film part 70d and the support unit 70s are formed. For example, in the case where the stacked film of $SiO_x$/Si is used as the thin film 90d used to form the film part 70d, deep patterning of the substrate 90s is performed from the back surface (the lower surface) of the thin film 90d toward the front surface (the upper surface) of the thin film 90d. Thereby, the hollow portion 70h is made. For example, a double-sided aligner exposure apparatus may be used to make the hollow portion 70h. Thereby, the hole pattern of the resist can be patterned in the back surface to match the position of the sensing element 50 of the front surface.

A Bosch process using, for example, RIE may be used to etch the Si substrate. In the Bosch process, for example, an etching process using $SF_6$ gas and a deposition process using $C_4F_8$ gas are repeated. Thereby, selective etching of the substrate 90s in the depth direction (the Z-axis direction) is performed while suppressing the etching of the side wall of the substrate 90s. For example, a $SiO_x$ layer is used as the end point of the etching. In other words, the selectivity of the etching is used to stop the etching by using the $SiO_x$ layer which is different from the Si. The $SiO_x$ layer that functions as the etching stopper layer may be used as a portion of the film part 70d. After the etching, the $SiO_x$ layer may be removed by processing such as, for example, anhydrous hydrogen fluoride, alcohol, etc.

Thus, the pressure sensor 110 according to the embodiment is formed. The other pressure sensors according to the embodiment also can be manufactured by similar methods.

Fourth Embodiment

Figure 41A:
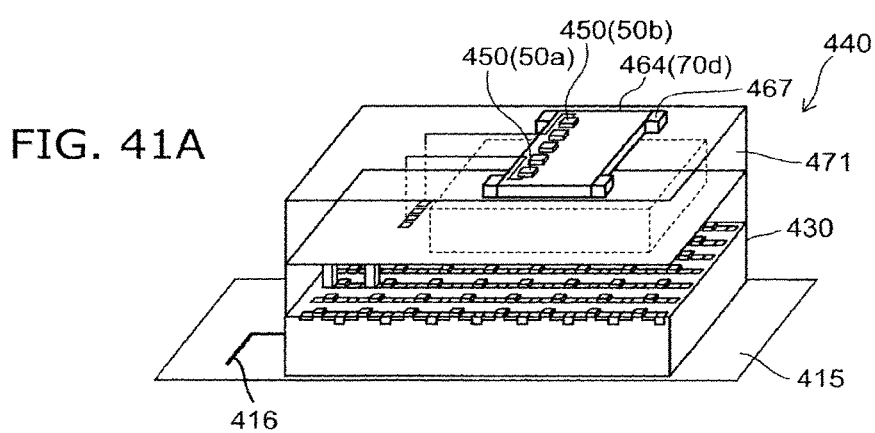
FIG. 41A to FIG. 41C are schematic views illustrating the configuration of a pressure sensor 440 according to a fourth embodiment.
Figure 41B:
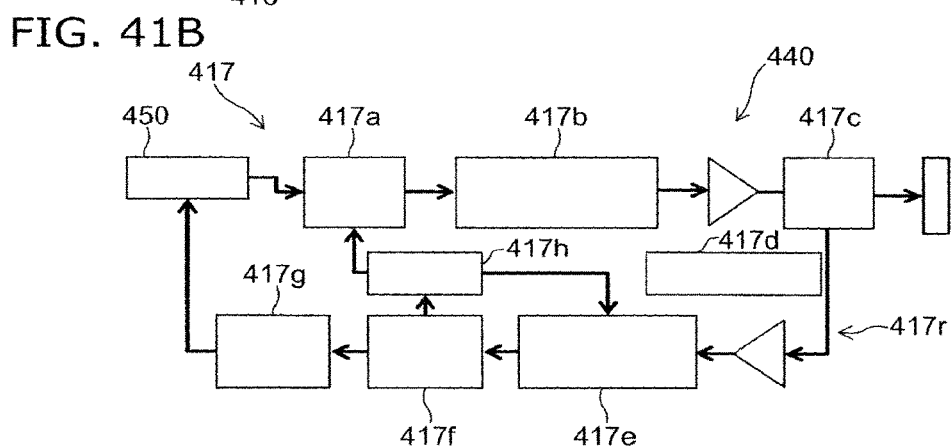
Figure 41C:
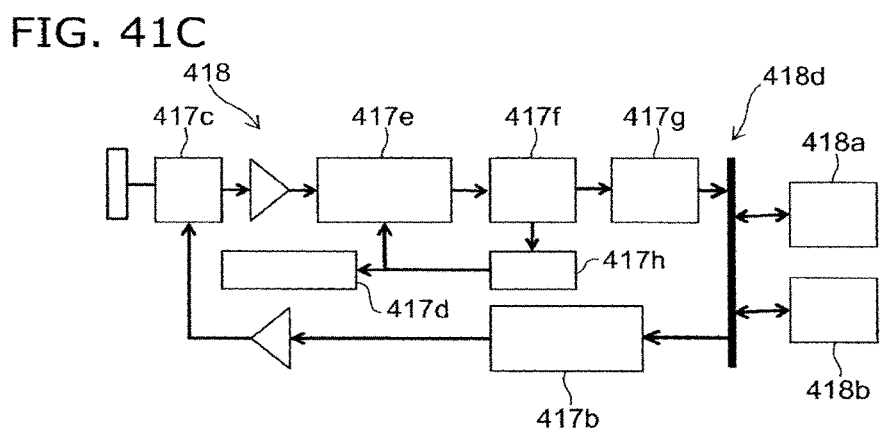

FIG. 41A to FIG. 41C are schematic views illustrating the configuration of a pressure sensor 440 according to a fourth embodiment.

FIG. 41A is a schematic perspective view; and FIG. 41B and FIG. 41C are block diagrams illustrating the configuration of the pressure sensor 440.

As shown in FIG. 41A and FIG. 41B, a base unit 471, a sensing element 450, a semiconductor circuit unit 430, an antenna 415, an electrical interconnect 416, a transmitting circuit 417, and a receiving circuit 417r are provided in the pressure sensor 440.

The antenna 415 is electrically connected to the semiconductor circuit unit 430 via the electrical interconnect 416.

The transmitting circuit 417 performs a wireless transmission of data based on an electrical signal flowing in the sensing element 450 (50a). At least a portion of the transmitting circuit 417 may be provided in the semiconductor circuit unit 430.

The receiving circuit 417r receives a control signal from an electronic device 418d. At least a portion of the receiving circuit 417r may be provided in the semiconductor circuit unit 430. By providing the receiving circuit 417r, the operation of the pressure sensor 440 can be controlled by, for example, operating the electronic device 418d.

Also, as shown in FIG. 41B, for example, a Manchester encoding unit 417b and an AD converter 417a that is connected to the sensing element 450 (50a) may be provided in the transmitting circuit 417. Further, a switching unit 417c may be provided to switch between transmitting and receiving. In such a case, a timing controller 417d may be provided; and the switching of the switching unit 417c may be controlled by the timing controller 417d. A data correcting unit 417e, a synchronizing unit 417f, a determining unit 417g, and a voltage-controlled oscillator 417h (VCO) may be further provided.

As shown in FIG. 41C, a receiving unit 418 is provided in the electronic device 418d used in combination with the pressure sensor 440. Electronic devices such as, for example, portable terminals, etc., may be used as the electronic device 418d.

In such a case, the electronic device 418d that includes the receiving unit 418 can be used in combination with the pressure sensor 440 that includes the transmitting circuit 417.

The Manchester encoding unit 417b, the switching unit 417c, the timing controller 417d, the data correcting unit 417e, the synchronizing unit 417f, the determining unit 417g, the voltage-controlled oscillator 417h, a memory unit 418a, and a central processing unit (CPU) 418b may be provided in the electronic device 418d.

In the example, the pressure sensor 440 further includes a fixing unit 467. The fixing unit 467 fixes a film part 464 (70d) to the base unit 471. The thickness dimension of the fixing unit 467 may be thicker than that of the film part 464 such that the fixing unit 467 does not deflect even when the external pressure is applied.

For example, the fixing unit 467 may be provided at uniform spacing at the circumferential edge of the film part 464.

Or, the fixing unit 467 may be provided continuously around the entire periphery of the film part 464 (70d).

The fixing unit 467 may be formed from, for example, the same material as the base unit 471. In such a case, the fixing unit 467 may be formed from, for example, silicon, etc.

It is also possible to form the fixing unit 467 from, for example, the same material as the film part 464 (70d).

Fifth Embodiment

A method for manufacturing a pressure sensor 441 will now be described.

FIG. 42A, FIG. 42B, FIG. 43A, FIG. 43B, FIG. 44A, FIG. 44B, FIG. 45A, FIG. 45B, FIG. 46A, FIG. 46B, FIG. 47A, FIG. 47B, FIG. 48A, FIG. 48B, FIG. 49A, FIG. 49B, FIG. 50A, FIG. 50B, FIG. 51A, FIG. 51B, FIG. 52A, FIG. 52B, FIG. 53A, and FIG. 53B are schematic views illustrating the method for manufacturing the pressure sensor 441 according to the fifth embodiment.

FIG. 42A to FIG. 53A are schematic plan views; and FIG. 42B to FIG. 53B are schematic cross-sectional views.

Arrows X, Y, and Z illustrate mutually orthogonal directions in the drawings.

Figure 42A:
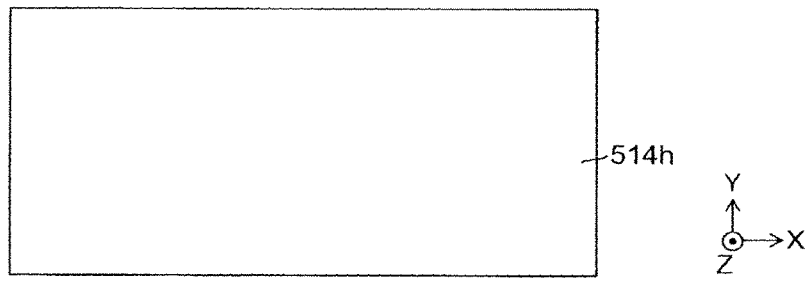
FIG. 42A, FIG. 42B, FIG. 43A, FIG. 43B, FIG. 44A, FIG. 44B, FIG. 45A, FIG. 45B, FIG. 46A, FIG. 46B, FIG. 47A, FIG. 47B, FIG. 48A, FIG. 48B, FIG. 49A, FIG. 49B, FIG. 50A, FIG. 50B, FIG. 51A, FIG. 51B, FIG. 52A, FIG. 52B, FIG. 53A, and FIG. 53B are schematic views illustrating the method for manufacturing the pressure sensor 441 according to the fifth embodiment.
Figure 42B:
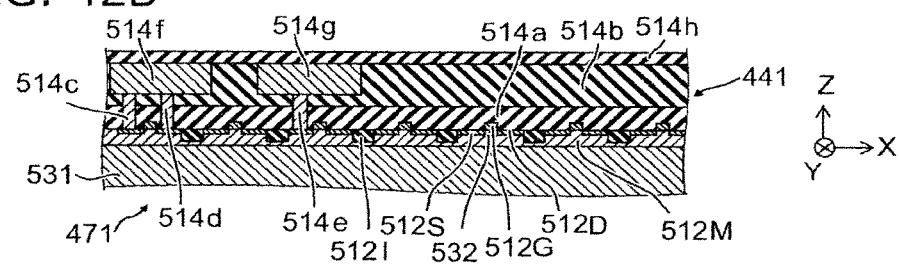

First, as shown in FIG. 42A and FIG. 42B, a semiconductor layer 512M is formed at the front surface portion of a semiconductor substrate 531. Continuing, an element-isolation insulation layer 512I is formed on the upper surface of the semiconductor layer 512M. Then, a gate 512G is formed on the semiconductor layer 512M with a not-shown insulating layer interposed. Continuing, a transistor 532 is formed by forming a source 512S and a drain 512D on two sides of the gate 512G. Then, an inter-layer insulating film 514a is formed on the transistor 532; and an inter-layer insulating film 514b is formed on the inter-layer insulating film 514a.

Continuing, trenches and holes are made in a portion of the inter-layer insulating films 514a and 514b in the region where the non-hollow portion is to be formed. Then, connecting pillars 514c to 514e are formed by filling a conductive material into the holes. In such a case, for example, the connecting pillar 514c is electrically connected to the source 512S of one transistor 532; and the connecting pillar 514d is electrically connected to the drain 512D of the one transistor 532. Also, for example, the connecting pillar 514e is electrically connected to the source 512S of one other transistor 532. Continuing, interconnect units 514f and 514g are formed by filling a conductive material into the trenches. The interconnect unit 514f is electrically connected to the connecting pillar 514c and the connecting pillar 514d. The interconnect unit 514g is electrically connected to the connecting pillar 514e. Continuing, an inter-layer insulating film 514h is formed on the inter-layer insulating film 514b.

Figure 43A:
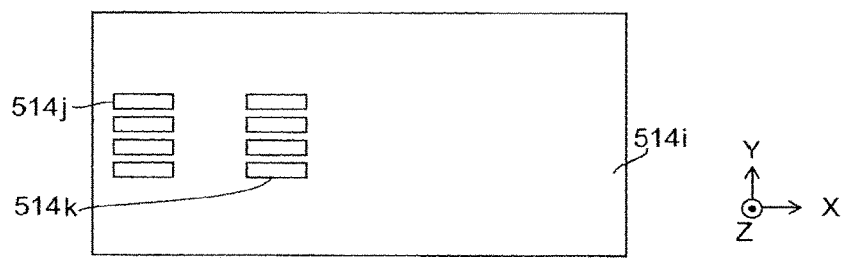
Figure 43B:
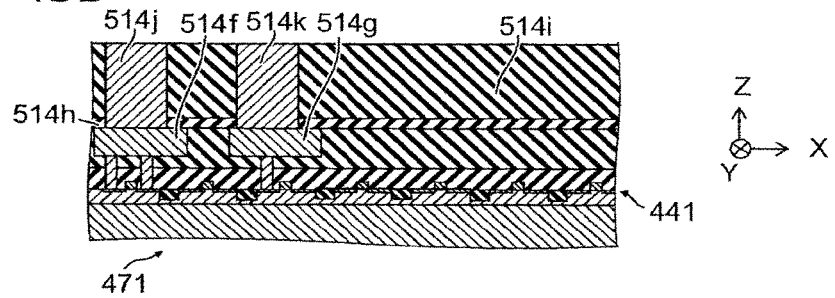

Then, as shown in FIG. 43A and FIG. 43B, an inter-layer insulating film 514i that is made of silicon oxide ($SiO_2$) is formed on the inter-layer insulating film 514h by, for example, CVD (Chemical Vapor Deposition). Continuing, holes are made at prescribed positions of the inter-layer insulating film 514i; a conductive material (e.g., a metal material) is filled; and the upper surface is planarized by CMP (Chemical Mechanical Polishing). Thereby, a connecting pillar 514j that is connected to the interconnect unit 514f and a connecting pillar 514k that is connected to the interconnect unit 514g are formed.

Figure 44A:
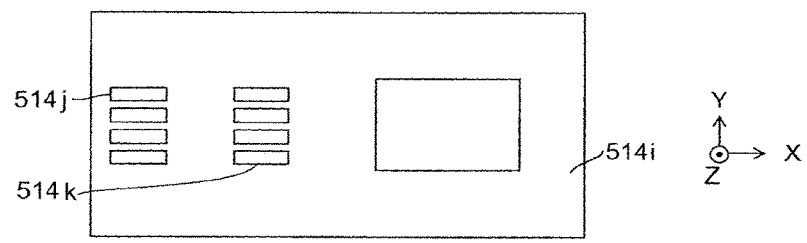
Figure 44B:
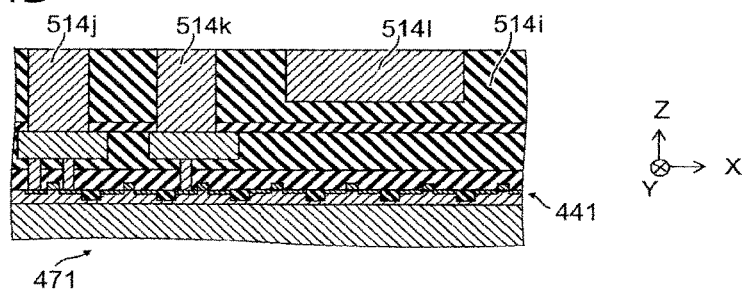

Continuing as shown in FIG. 44A and FIG. 44B, a recess is made in the region of the inter-layer insulating film 514i where a hollow portion 570 is to be made; and a sacrificial layer 514l is filled into the recess. The sacrificial layer 514l may be formed of, for example, a material that can be formed at a low temperature. The material that can be formed at the low temperature is, for example, silicon-germanium (SiGe), etc.

Figure 45A:
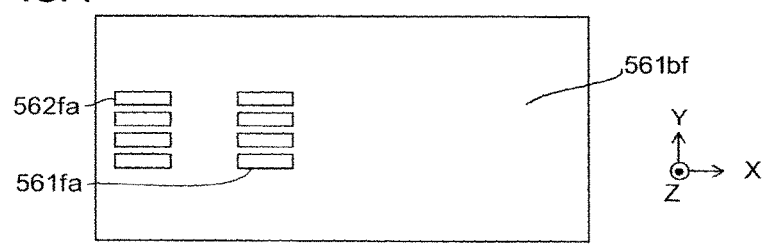
Figure 45B:
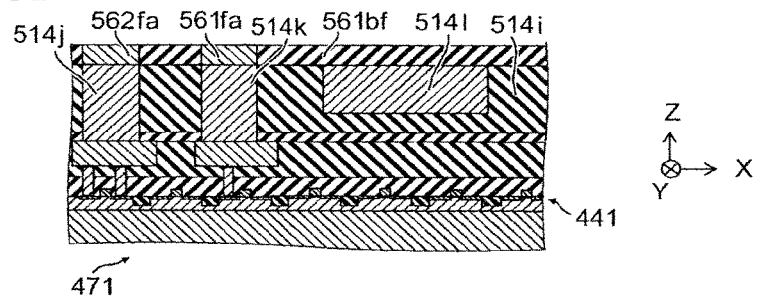

Then, as shown in FIG. 45A and FIG. 45B, an insulating film 561bf that is used to form a film part 564 (70d) is formed on the inter-layer insulating film 514i and the sacrificial layer 514l. The insulating film 561bf may be formed of, for example, silicon oxide ($SiO_2$), etc. A connecting pillar 561fa and a connecting pillar 562fa are formed by providing multiple holes in the insulating film 561bf and by filling a conductive material (e.g., a metal material) into the multiple holes. The connecting pillar 561fa is electrically connected to the connecting pillar 514k; and the connecting pillar 562fa is electrically connected to the connecting pillar 514j.

Figure 46A:
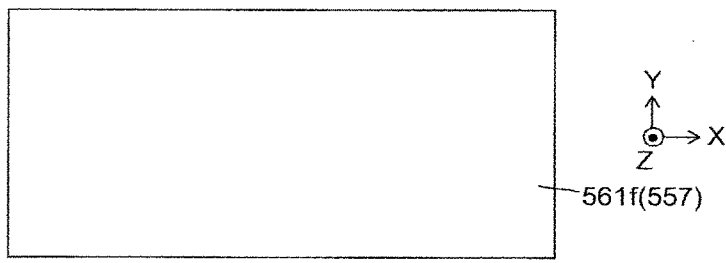
Figure 46B:
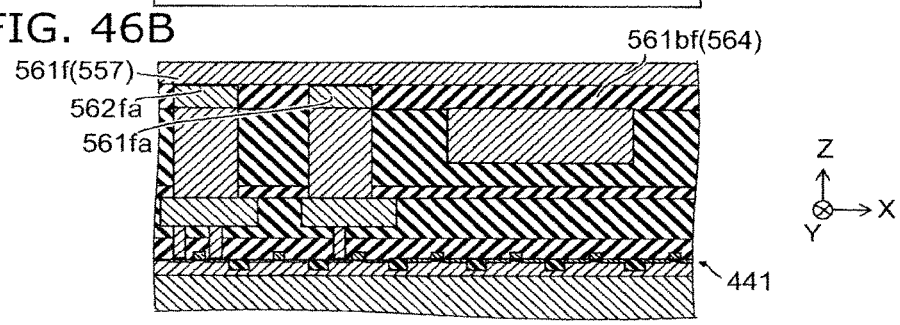

Continuing as shown in FIG. 46A and FIG. 46B, a conductive layer 561f that is used to form an interconnect 557 is formed on the insulating film 561bf, the connecting pillar 561fa, and the connecting pillar 562fa.

Figure 47A:
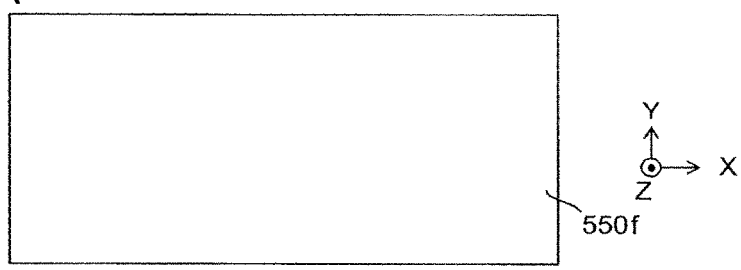
Figure 47B:
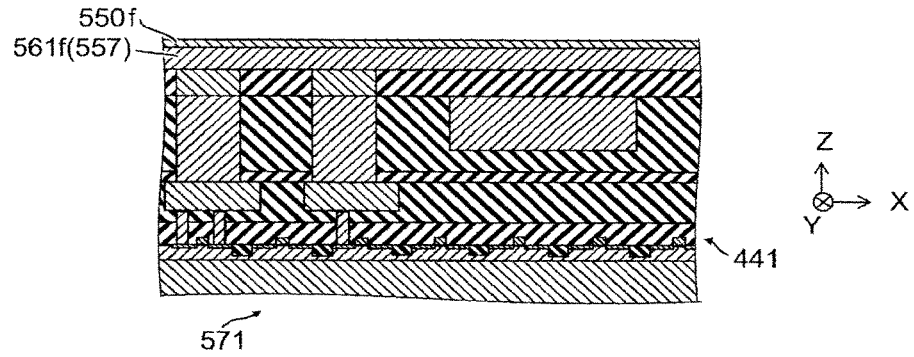

Then, as shown in FIG. 47A and FIG. 47B, a stacked film 550f that is used to form the sensing element 50 is formed on the conductive layer 561f.

Figure 48A:
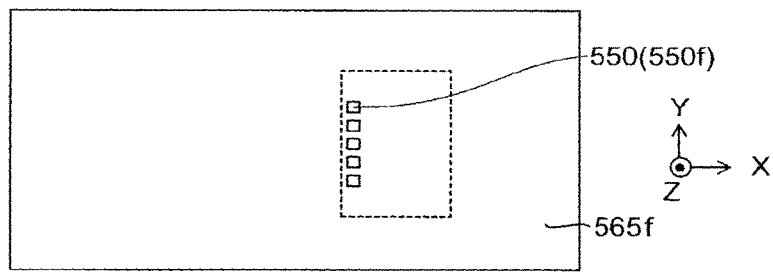
Figure 48B:
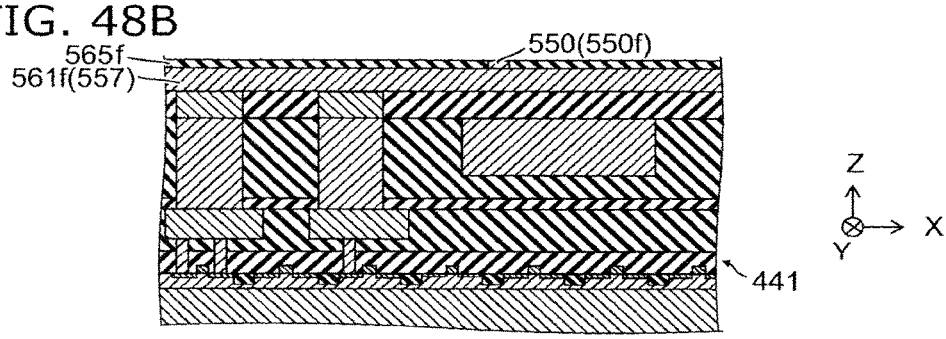

Continuing as shown in FIG. 48A and FIG. 48B, the stacked film 550f is patterned into a prescribed configuration; and an insulating film 565f that is used to form an insulating layer 565 is formed on the stacked film 550f. The insulating film 565f can be formed by, for example, silicon oxide ($SiO_2$), etc.

Figure 49A:
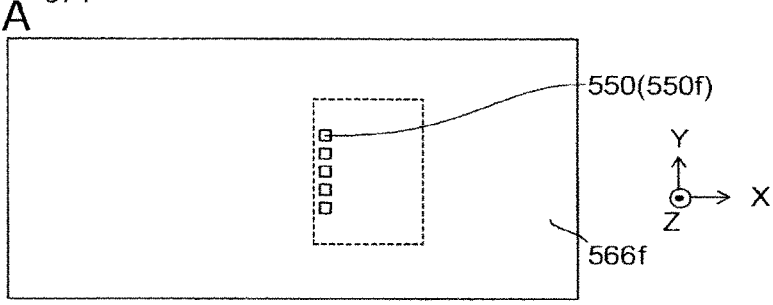
Figure 49B:
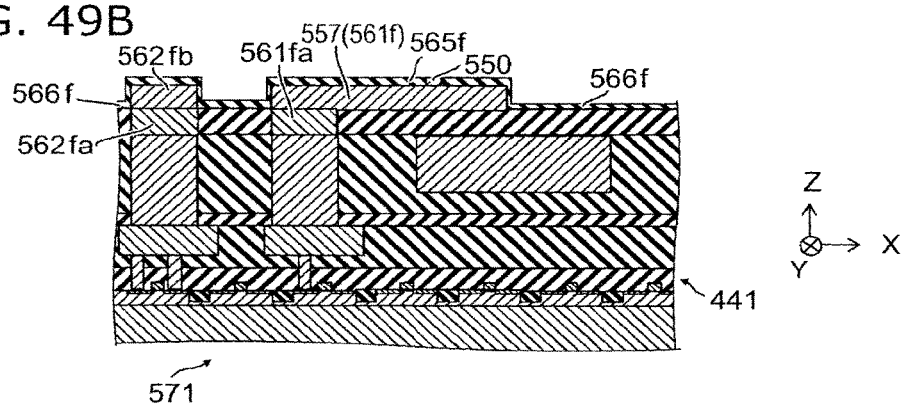

Then, as shown in FIG. 49A and FIG. 49B, a portion of the insulating film 565f is removed; and the conductive layer 561f is patterned into a prescribed configuration. Thereby, the interconnect 557 is formed. At this time, a portion of the conductive layer 561f becomes a connecting pillar 562fb that is electrically connected to the connecting pillar 562fa. Further, an insulating film 566f that is used to form an insulating layer 566 is formed on the connecting pillar 562fb.

Figure 50A:
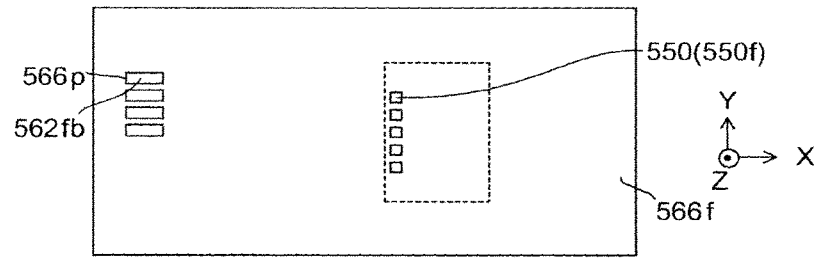
Figure 50B:
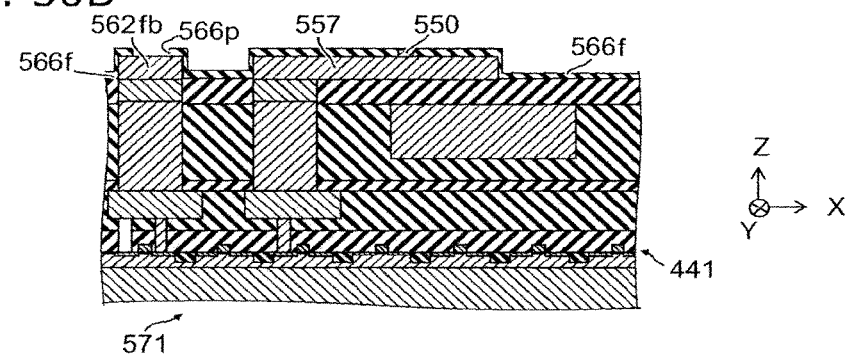

Continuing as shown in FIG. 50A and FIG. 50B, an opening 566p is made in the insulating film 566f. Thereby, the connecting pillar 562fb is exposed.

Figure 51A:
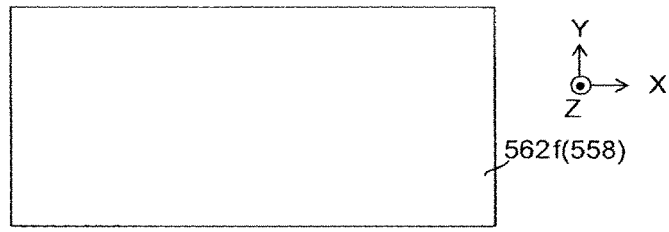
Figure 51B:
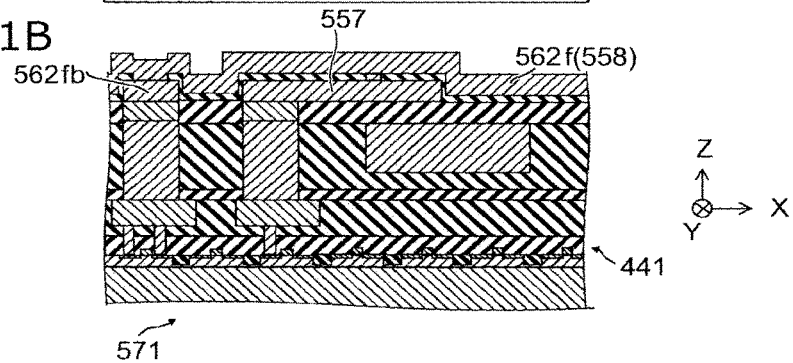

Then, as shown in FIG. 51A and FIG. 51B, a conductive layer 562f that is used to form an interconnect 558 is formed on the upper surface. A portion of the conductive layer 562f is electrically connected to the connecting pillar 562fb.

Figure 52A:
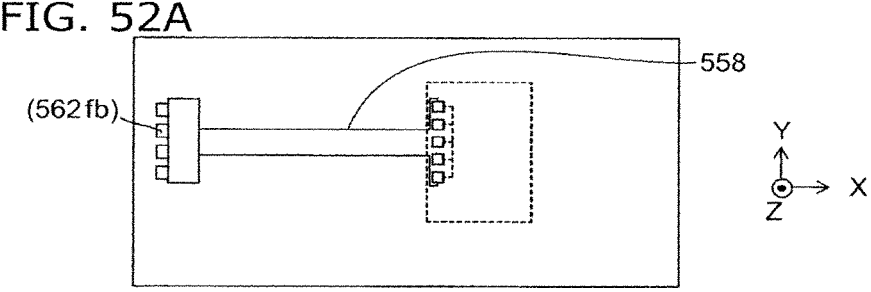
Figure 52B:
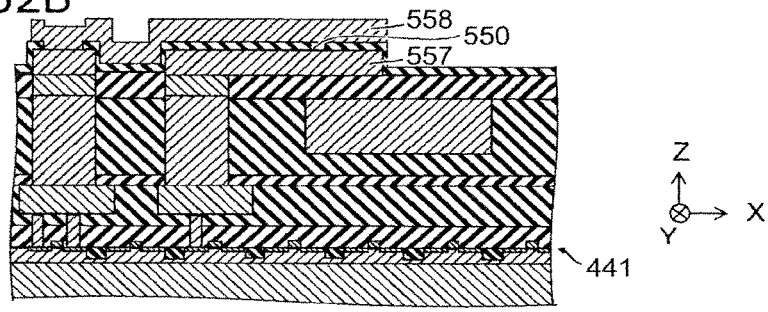

Continuing as shown in FIG. 52A and FIG. 52B, the conductive layer 562f is patterned into a prescribed configuration. Thereby, the interconnect 558 is formed. The interconnect 558 is electrically connected to the connecting pillar 562fb.

Figure 53A:
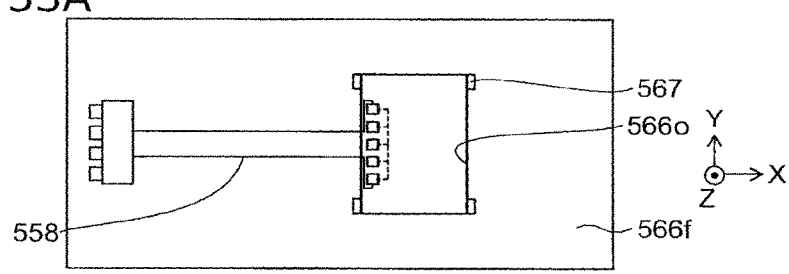
Figure 53B:
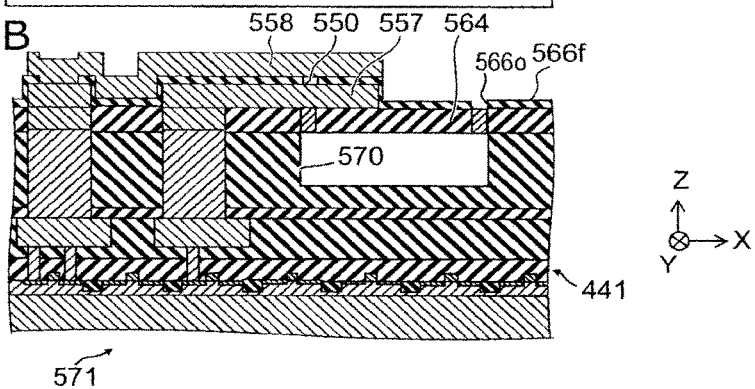

Then, as shown in FIG. 53A and FIG. 53B, an opening 566o having a prescribed configuration is made in the insulating film 566f. The insulating film 561bf is patterned via the opening 566o; and the sacrificial layer 514l is removed via the opening 566o. Thereby, the hollow portion 570 is made. The removal of the sacrificial layer 514l may be performed by, for example, wet etching.

To form a fixing unit 567 to have a ring configuration, for example, the space between the film part 564 and the edge of the non-hollow portion above the hollow portion 570 may be filled with an insulating film.

Thus, the pressure sensor 441 is formed.

Figure 54:
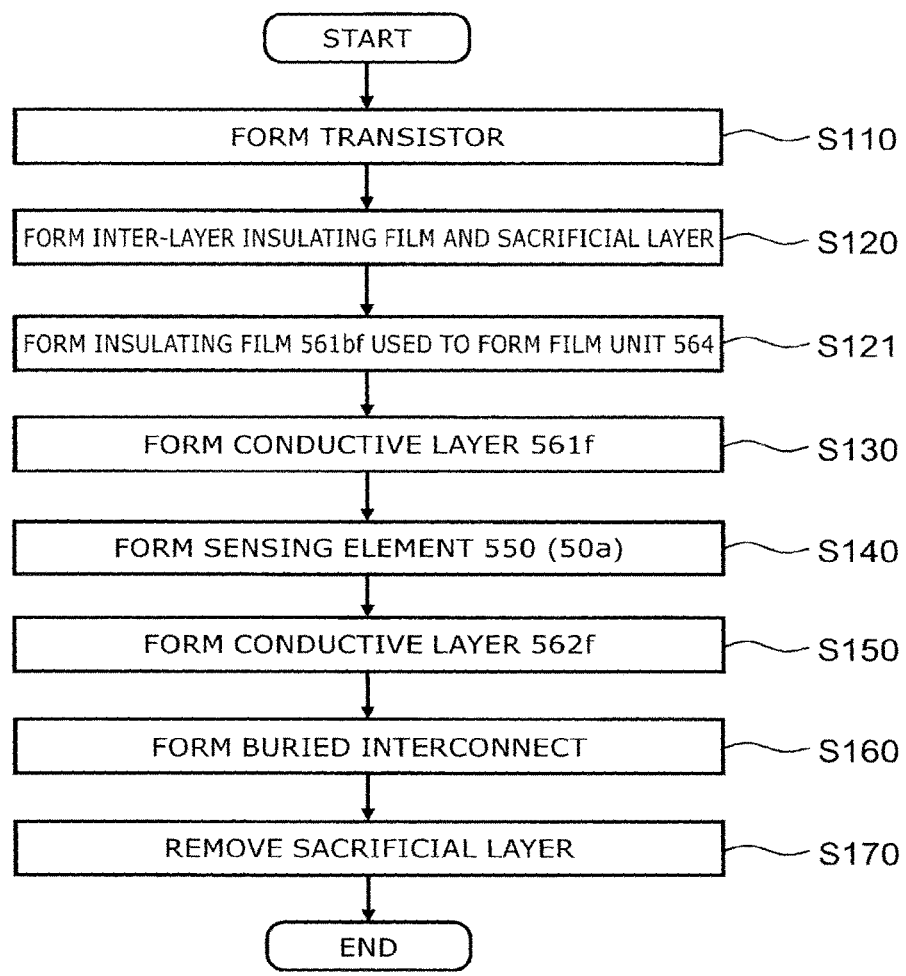
FIG. 54 is a flowchart illustrating the method for manufacturing the pressure sensor 441 according to the fifth embodiment.

FIG. 54 is a flowchart illustrating the method for manufacturing the pressure sensor 441 according to the fifth embodiment.

Namely, FIG. 54 is a flowchart of the method for manufacturing the pressure sensor 441 illustrated in FIG. 42A to FIG. 53B.

First, as shown in FIG. 54, the transistor 532 is formed on the semiconductor substrate 531 (step S110).

For example, the transistor 532 is formed as illustrated in FIG. 42A and FIG. 42B.

Then, an inter-layer insulating layer is formed on the semiconductor substrate 531; and the sacrificial layer 514l is formed on the transistor 532 (step S120).

For example, the inter-layer insulating layers and the sacrificial layer 514l are formed as illustrated in FIG. 43A to FIG. 44B. For example, the inter-layer insulating film 514i is included in the inter-layer insulating layers.

Then, the insulating film 561bf that is used to form the film part 564 is formed on the inter-layer insulating layers (e.g., the inter-layer insulating film 514i) and the sacrificial layer 514l (step S121).

In some cases, the conductive layer 561f recited below also is used as the film part 564 (70d). In such a case, step S121 is omitted.

Then, the conductive layer 561f that is used to form the interconnect 557 is formed (step S130).

For example, the conductive layer 561f is formed as illustrated in FIG. 46A and FIG. 46B.

Then, the sensing element 550 that includes the first magnetic layer 10 is formed above the sacrificial layer 514l and on the conductive layer 561f (step S140).

For example, the sensing element 550 is formed as illustrated in FIG. 47A to FIG. 48B.

Then, the conductive layer 562f that is used to form the interconnect 558 is formed on the sensing element 550 (50a) (step S150).

For example, the conductive layer 562f is formed as illustrated in FIG. 51A to FIG. 52B.

Continuing, buried interconnects are formed (step S160).

For example, an interconnect that electrically connects the conductive layer 561f to the semiconductor substrate 531 and an interconnect that electrically connects the conductive layer 562f to the semiconductor substrate 531 are formed inside the inter-layer insulating layers. For example, the buried interconnects are formed as illustrated in FIG. 42A, FIG. 42B, FIG. 43A, FIG. 43B, FIG. 45A, FIG. 45B, FIG. 49A, and FIG. 49B.

Step S160 may be implemented, for example, once or multiple times in any process between step S110 to step S150 and after step S150.

Then, the sacrificial layer 514l is removed (step S170).

For example, the sacrificial layer 514l is removed as illustrated in FIG. 53A and FIG. 53B.

Thus, the pressure sensor is formed.

The content of the processes may be similar to that illustrated in FIG. 42A to FIG. 53B; and a detailed description is therefore omitted.

In each of the embodiments recited above, the magnetization direction of the magnetization free layer 55f (the first magnetic layer 10) in the state (e.g., the initial state) in which the external pressure is not applied is, for example, different from the first direction and different from the second direction. In each of the embodiments, when the external pressure is applied, the direction of the anisotropic strain applied to the magnetization free layer is along the first direction or the second direction. Therefore, by setting the magnetization direction of the magnetization free layer 55f in the state in which the external pressure is not applied to be as described above, a change of the output with respect to both a positive pressure and a negative pressure can be obtained.

In each of the embodiments recited above, the surface area of the film part 70d is, for example, not less than 2500 $\mu m^2$ and not more than 640000 $\mu m^2$. In the case where the surface area of the film part 70d is too small, it is difficult to obtain a sufficiently large strain occurring due to the external pressure. By setting the surface area of the film part 70d to be 2500 $\mu m^2$ or more, a strain that is sufficiently large can be obtained. In the case where the surface area of the film part is too large, the strength of the film part becomes insufficient; and it is difficult to provide a high-reliability pressure sensor. By setting the surface area of the film part 70d to be not more than 640000 $\mu m^2$, high reliability is obtained. In the case where each of the embodiments recited above is applied to a microphone, the frequency characteristics in the audible range degrade when the surface area of the film part is too large. It is favorable for the surface area of the film part 70d to be not more than 640000 µm², and more favorable to be not more than 360000 µm². Thereby, for example, good frequency characteristics in the audible range are obtained. From the reasons recited above, it is favorable to set the surface area of the film part 70d to be not less than 2500 µm² and not more than 640000 µm².

In each of the embodiments recited above, the second length of the film part 70d is, for example, not less than 20 µm and not more than 800 µm. In the case where the second length of the film part 70d is too short, it is difficult to obtain a strain occurring due to the external pressure that is sufficiently large. By setting the second length of the film part 70d to be 20 µm or more, a strain that is sufficiently large can be obtained. In the case where the second length of the film part 70d is too large, the strength of the film part becomes insufficient; and it is difficult to provide a highly-reliable pressure sensor. By setting the second length of the film part 70d to be 800 µm or less, a highly-reliable pressure sensor is obtained. In the case where each of the embodiments recited above is applied to a microphone, the frequency characteristics in the audible range degrade in the case where the second length of the film part 70d is too large. It is favorable for the second length of the film part 70d to be 800 µm or less, and more favorable to be 600 µm or less. Thereby, for example, good frequency characteristics in the audible range are obtained. From the reasons recited above, it is favorable for the second length of the film part 70d to be not less than 20 µm and not more than 800 µm.

Sixth Embodiment

Figure 55:
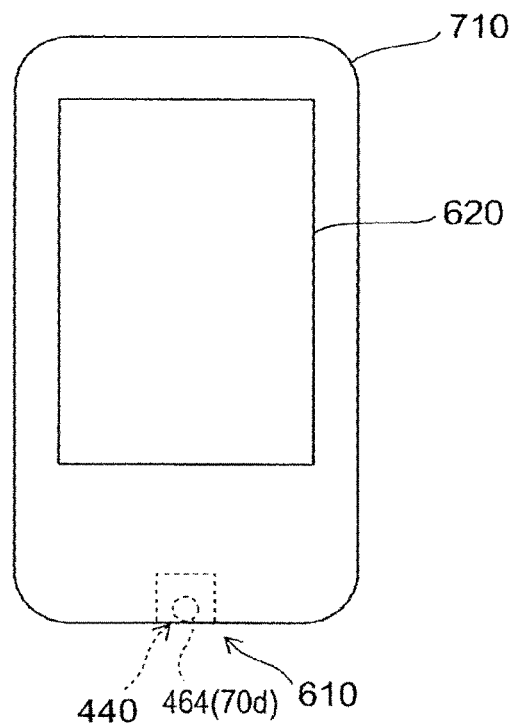
FIG. 55 is a schematic view illustrating a microphone 610 according to a sixth embodiment.

FIG. 55 is a schematic view illustrating a microphone 610 according to a sixth embodiment.

As shown in FIG. 55, the microphone 610 includes any pressure sensor (e.g., the pressure sensor 440) according to the embodiments described above or a pressure sensor according to a modification of these pressure sensors. The microphone 610 that includes the pressure sensor 440 will now be described as an example.

The microphone 610 is embedded in the end portion of a personal digital assistant 710. The film part 464 (70d) of the pressure sensor 440 provided in the microphone 610 may be substantially parallel to, for example, the front surface of the personal digital assistant 710 where a display unit 620 is provided. The disposition of the film part 464 (70d) is not limited to that illustrated and may be modified appropriately.

Because the microphone 610 includes the pressure sensor 440, etc., high sensitivity with respect to frequencies in the wide band is possible.

Although the case where the microphone 610 is embedded in the personal digital assistant 710 is illustrated, this is not limited thereto. The microphone 610 also may be embedded in, for example, an IC recorder, a pin microphone, etc.

Seventh Embodiment

The embodiment relates to an acoustic microphone using the pressure sensors of the embodiments recited above.

Figure 56:
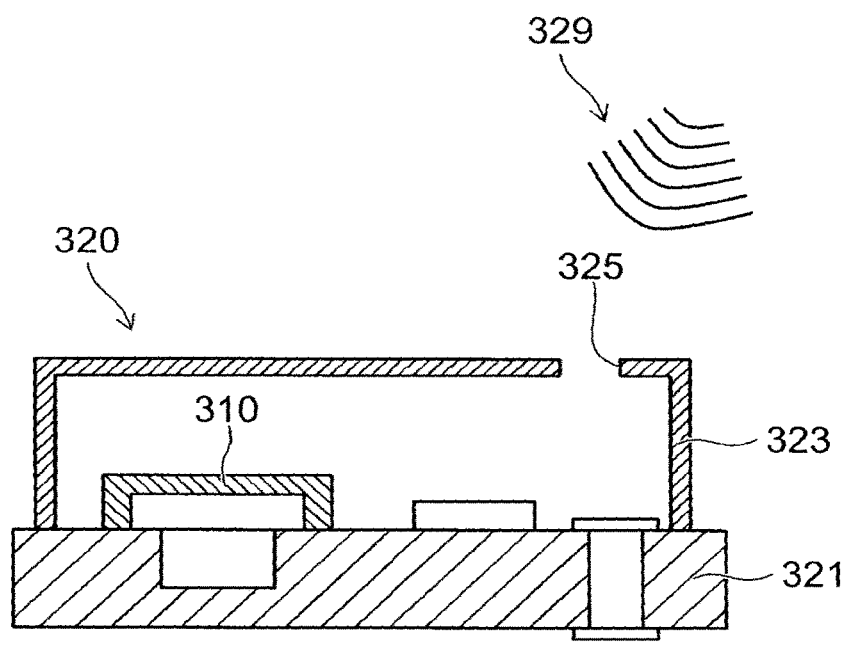
FIG. 56 is a schematic cross-sectional view illustrating the acoustic microphone according to the seventh embodiment.

FIG. 56 is a schematic cross-sectional view illustrating the acoustic microphone according to the seventh embodiment.

According to the embodiment, an acoustic microphone 320 includes a printed circuit board 321, a cover 323, and a pressure sensor 310. The printed circuit board 321 includes, for example, a circuit such as an amplifier, etc. An acoustic hole 325 is provided in the cover 323. Sound 329 passes through the acoustic hole 325 to enter the interior of the cover 323.

Any of the pressure sensors described in regard to the embodiments recited above or a pressure sensor according to a modification of these pressure sensors may be used as the pressure sensor 310.

The acoustic microphone 320 responds to sound pressure. A highly-sensitive acoustic microphone 320 is obtained by using a highly-sensitive pressure sensor 310. For example, the pressure sensor 310 is mounted on the printed circuit board 321; and electrical signal lines are provided. The cover 323 is provided on the printed circuit board 321 to cover the pressure sensor 310.

According to the embodiment, a highly-sensitive acoustic microphone can be provided.

Eighth Embodiment

The embodiment relates to a blood pressure sensor using the pressure sensors of the embodiments recited above.

Figure 57A:
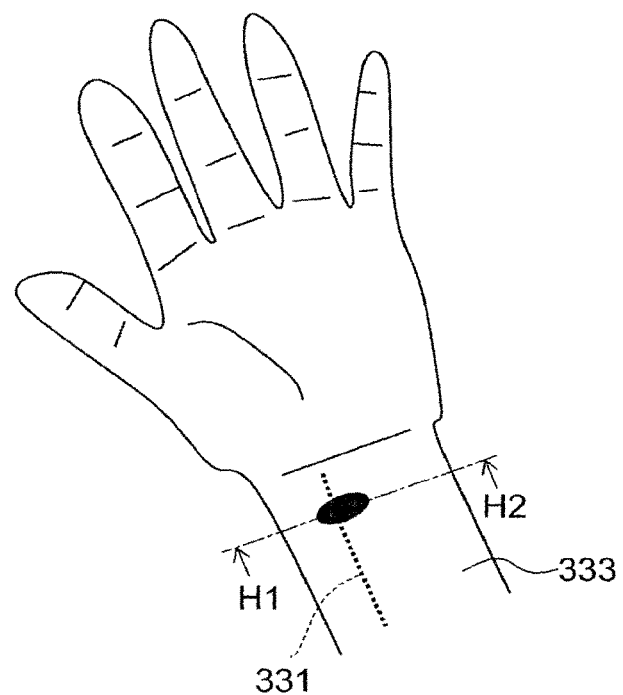
FIG. 57A and FIG. 57B are schematic views illustrating the blood pressure sensor according to the eighth embodiment.
Figure 57B:
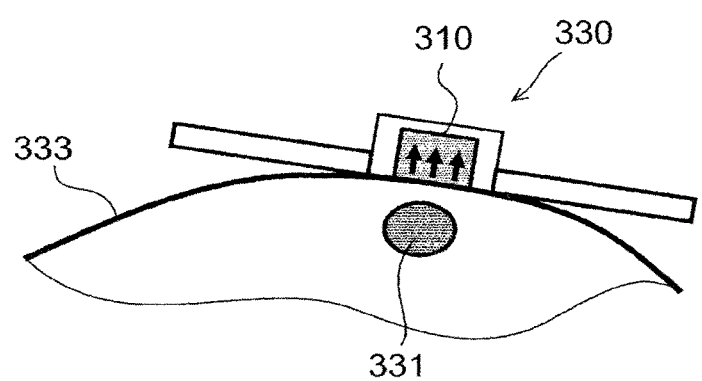

FIG. 57A and FIG. 57B are schematic views illustrating the blood pressure sensor according to the eighth embodiment.

FIG. 57A is a schematic plan view illustrating skin on the arterial vessel of a human. FIG. 57B is a cross-sectional view along line H1-H2 of FIG. 57A.

In the embodiment, a blood pressure sensor 330 includes the pressure sensor 310. The pressure sensor 310 includes any of the pressure sensors described in regard to the embodiments recited above or a pressure sensor according to a modification of these pressure sensors.

Thereby, highly-sensitive pressure sensing by a small pressure sensor is possible. The blood pressure sensor 330 can perform a continuous blood pressure measurement by the pressure sensor 310 being pressed onto skin 333 on an arterial vessel 331.

According to the embodiment, a highly-sensitive blood pressure sensor can be provided.

Ninth Embodiment

The embodiment relates to a touch panel using the pressure sensors of the embodiments recited above.

Figure 58:
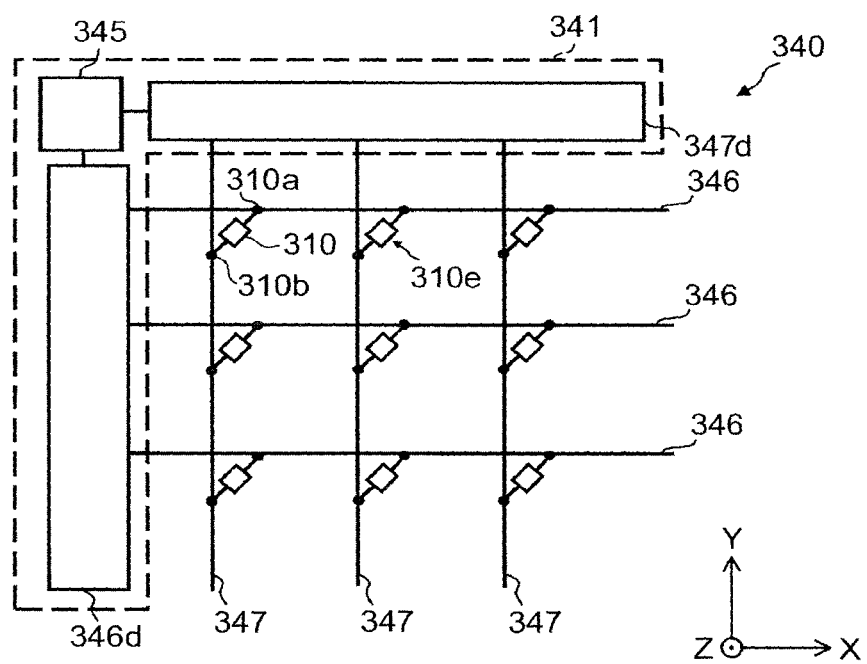
FIG. 58 is a schematic view illustrating the touch panel according to the ninth embodiment.

FIG. 58 is a schematic view illustrating the touch panel according to the ninth embodiment.

In the embodiment, the pressure sensor 310 may be used in a touch panel 340. The pressure sensor 310 includes any of the pressure sensors described in regard to the embodiments recited above or a pressure sensor according to a modification of these pressure sensors. The pressure sensor 310 is provided in the interior of the display and/or outside the display of the touch panel 340.

For example, the touch panel 340 includes multiple first interconnects 346, multiple second interconnects 347, multiple pressure sensors 310, and a controller 341.

In the example, the multiple first interconnects 346 are arranged along the Y-axis direction. Each of the multiple first interconnects 346 extends along the X-axis direction. The multiple second interconnects 347 are arranged along the X-axis direction. Each of the multiple second interconnects 347 extends along the Y-axis direction.

The multiple pressure sensors 310 are provided respectively at the intersections between the multiple first interconnects 346 and the multiple second interconnects 347. One pressure sensor 310 is used as one sensing component 310e for sensing. Herein, the intersections include the regions around the positions where the first interconnects 346 and the second interconnects 347 intersect.

Multiple one ends 310a of the multiple pressure sensors 310 are connected to the multiple first interconnects 346. Multiple other ends 310b of the multiple pressure sensors 310 are connected to the multiple second interconnects 347.

The controller 341 is connected to the multiple first interconnects 346 and the multiple second interconnects 347.

For example, the controller 341 includes a first interconnect circuit 346d that is connected to the multiple first interconnects 346, a second interconnect circuit 347d that is connected to the multiple second interconnects 347, and a control circuit 345 that is connected to the first interconnect circuit 346d and the second interconnect circuit 347d.

The pressure sensor 310 can be miniature and can provide highly-sensitive pressure sensing. Therefore, it is possible to realize a high definition touch panel.

Other than the applications recited above, the pressure sensors according to the embodiments recited above are applicable to various pressure sensor devices such as atmospheric pressure sensors, air pressure sensors of tires, etc.

The embodiments include the following features.

Feature 1
A pressure sensor, comprising:
a film part supported by a support unit, the film part being flexible; and
a sensing unit,
a first length of a film surface of the film part in a first direction in the film surface being longer than a second length of the film surface in a second direction perpendicular to the first direction in the film surface,
the film surface having a central portion, and a peripheral portion provided around the central portion,
the sensing unit including a sensing element provided on the central portion, the sensing element including a first magnetic layer, a second magnetic layer provided between the first magnetic layer and the film part, and a spacer layer provided between the first magnetic layer and the second magnetic layer.

Feature 2
The sensor according to feature 1, wherein the film surface includes:
a first side along the first direction;
a second side along the first direction to be separated from the first side;
a third side along the second direction to be connected to one end of the first side and one end of the second side; and
a fourth side along the second direction to be separated from the third side and connected to the other end of the first side and the other end of the second side.

Feature 3
The sensor according to feature 1, wherein a configuration of the film surface is a flattened circle having the first direction as a major axis and the second direction as a minor axis.

Feature 4
The sensor according to any of features 1 to 3, wherein
a third length of the central portion in the first direction is not more than 0.3 times the first length,
a fourth length of the central portion in the second direction is not more than 0.3 times the second length, and
a distance between a centroid of the central portion and a centroid of the film surface is not more than 1/10 of the second length.

Feature 5
The sensor according to feature 4, wherein
L2/L1 is not less than 0.8 but less than 1,
L3 is not less than 0.8 times and not more than 1.2 times L1×{−0.8×(L2/L1)+0.8}, and
L4 is not less than 0.8 times and not more than 1.2 times L2×{−2.5×(L2/L1)+2.5},
where the first length is L1, the second length is L2, the third length is L3, and the fourth length is L4.

Feature 6
The sensor according to feature 4, wherein
L2/L1 is less than 0.8,
L3 is not less than 0.8 times and not more than 1.2 times L1×{−0.8×(L2/L1)+0.8}, and
L4 is not less than 0.8 times and not more than 1.2 times L2×{0.375×(L2/L1)+0.2},
where the first length is L1, the second length is L2, the third length is L3, and the fourth length is L4.

Feature 7
The sensor according to any of features 1 to 6, wherein the ratio of the second length to the first length is not less than 0.1 and not more than 0.8.

Feature 8
The sensor according to any of features 1 to 6, wherein the ratio of the second length to the first length is not less than 0.25 and not more than 0.64.

Feature 9
The sensor according to any of features 1 to 6, wherein the ratio of the second length to the first length is not more than 0.25.

Feature 10
The sensor according to any of features 1 to 9, wherein the sensing unit includes a plurality of the sensing elements.

Feature 11
The sensor according to any of features 1 to 10, wherein at least two of the multiple sensing elements are connected electrically in series.

Feature 12
A pressure sensor, comprising:
a film part supported by a support unit, the film part being flexible; and
a sensing unit,
the film surface of the film part having a central portion, and a peripheral portion provided around the central portion,
the sensing unit including a sensing element provided on the peripheral portion, the sensing element including a first magnetic layer, a second magnetic layer provided between the first magnetic layer and the film part,
a spacer layer provided between the first magnetic layer and the second magnetic layer,
the film part including:
a first side along a first direction;
a second side along the first direction to be separated from the first side;
a third side along a second direction to be connected to one end of the first side and one end of the second side; and
a fourth side along the second direction to be separated from the third side and connected to the other end of the first side and the other end of the second side,
the peripheral portion has a first element disposition region provided along the first side, and
positions in the first direction of at least two of the multiple sensing elements disposed in the first element disposition region are different from each other.

Feature 13

The sensor according to feature 12, wherein the at least two of the multiple sensing elements are connected electrically in series.

According to the embodiments, a pressure sensor, an acoustic microphone, a blood pressure sensor, and a touch panel that have high sensitivity can be provided.

Hereinabove, embodiments of the invention are described with reference to specific examples. However, the invention is not limited to these specific examples. For example, one skilled in the art may similarly practice the invention by appropriately selecting specific configurations of components included in the pressure sensor, the acoustic microphone, the blood pressure sensor, and the touch panel such as the support unit, the film part, the sensing element, the first magnetic layer, the second magnetic layer, the spacer layer, etc., from known art; and such practice is within the scope of the invention to the extent that similar effects are obtained.

Various other variations and modifications can be conceived by those skilled in the art within the spirit of the invention, and it is understood that such variations and modifications are also encompassed within the scope of the invention.

Moreover, all pressure sensors, acoustic microphones, blood pressure sensors, and touch panels practicable by an appropriate design modification by one skilled in the art based on the pressure sensors, acoustic microphones, blood pressure sensors, and touch panels described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a film part supported by a support unit, the film part being flexible, the film part having a film surface; and
a sensing unit fixed to the film surface,
the sensing unit including a first sensing group, and a second sensing group,
the first sensing group including a plurality of first sensing elements, and the second sensing group including a plurality of second sensing elements,
the first sensing elements being arranged along a first direction,
the second sensing elements being arranged along the first direction, the second sensing elements being apart from the first sensing elements along a second direction crossing the first direction,
a distance in the first direction between two of the first sensing elements being shorter than a distance in the second direction between one of the first sensing elements and one of the second sensing elements, the two of the first sensing elements being closest among the first sensing elements,
a distance in the first direction between two of the second sensing elements being shorter than the distance in the second direction between one of the first sensing elements and one of the second sensing elements, the two of the second sensing elements being closest among the second sensing elements,
the first sensing elements being connected in series with each other, and the second sensing elements being connected in series with each other, each of the first sensing elements and the including a first magnetic layer, a second magnetic layer provided between the first magnetic layer and the film part, and a spacer layer provided between the first magnetic layer and the second magnetic layer,
a first end of the first sensing group being connected with a first node of a bridge circuit,
a second end of the first sensing group being connected with a second node of the bridge circuit,
a third end of the second sensing group being connected with a third node of the bridge circuit,
a fourth end of the second sensing group being connected with a fourth node of the bridge circuit,
the sensing unit further including a third sensing group and a fourth sensing group,
the third sensing group including a plurality of third sensing elements, and the fourth sensing group including a plurality of fourth sensing elements,
the third sensing elements being arranged along the second direction,
the fourth sensing elements being arranged along the second direction,
a distance in the second direction between two of the third sensing elements being shorter than a distance in the first direction between one of the third sensing elements and one of the fourth sensing elements, the two of the third sensing elements being closest among the third sensing elements,
a distance in the second direction between two of the fourth sensing elements being shorter than the distance in the first direction between one of the third sensing elements and one of the fourth sensing elements, the two of the fourth sensing elements being closest among the fourth sensing elements,
the third sensing elements being connected in series with each other, and the fourth sensing elements being connected in series with each other, each of the third sensing elements and the fourth sensing elements including the first magnetic layer, the second magnetic layer, and the spacer layer,
a fifth end of the third sensing group being connected with the second node,
a sixth end of the third sensing group being connected with the third node,
a seventh end of the fourth sensing group being connected with the first node, and
an eighth end of the fourth sensing group being connected with the fourth node.

2. The sensor according to claim 1, wherein
a direction of a magnetization of the first magnetic layer in a state in which an external pressure is not applied to the sensor crosses the first direction and crosses the second direction.

3. The sensor according to claim 1, wherein a direction of a magnetization of the first magnetic layer is changeable, and a direction of a magnetization of the second magnetic layer is fixed.

4. An acoustic microphone including the sensor according to claim 1.

5. A blood pressure sensor including the sensor according to claim 1.

6. A touch panel including the sensor according to claim 1.

7. The sensor according to claim 1, wherein the second direction is perpendicular to the first direction.

* * * * *